(12) United States Patent
Falco et al.

(10) Patent No.: US 7,022,895 B2
(45) Date of Patent: Apr. 4, 2006

(54) PLANT AMINO ACID BIOSYNTHETIC ENZYMES

(75) Inventors: Saverio Carl Falco, Arden, DE (US); Stephen M. Allen, Wilmington, DE (US); J. Antoni Rafalski, Wilmington, DE (US); William D. Hitz, Wilmington, DE (US); Anthony John Kinney, Wilmington, DE (US); Lynn Marie Abell, Wilmington, DE (US); Catherine J. Thorpe, Hampshire (GB)

(73) Assignee: E.I. du Pont de Nemours and Company, Wilmington, DE (US)

( * ) Notice: Subject to any disclaimer, the term of this patent is extended or adjusted under 35 U.S.C. 154(b) by 153 days.

(21) Appl. No.: 10/734,698

(22) Filed: Dec. 12, 2003

(65) Prior Publication Data

US 2004/0209341 A1 Oct. 21, 2004

Related U.S. Application Data

(62) Division of application No. 09/424,978, filed as application No. PCT/US98/11692 on Jun. 5, 1998, now Pat. No. 6,664,445.

(60) Provisional application No. 60/049,443, filed on Jun. 12, 1997, provisional application No. 60/048,771, filed on Jun. 6, 1997.

(51) Int. Cl.
- *A01H 1/00* (2006.01)
- *C07H 21/04* (2006.01)
- *C07K 14/415* (2006.01)
- *C12N 5/14* (2006.01)
- *C12N 9/00* (2006.01)

(52) U.S. Cl. .................. 800/295; 435/6; 435/69.1; 435/468; 435/419; 435/252.3; 435/320.1; 435/183; 530/370; 536/23.6; 800/278

(58) Field of Classification Search .............. 435/6, 435/69.1, 468, 419, 252.3, 320.1, 183; 530/370; 536/23.6; 800/278, 296
See application file for complete search history.

(56) References Cited

U.S. PATENT DOCUMENTS 5,451,516 A 9/1995 Matthews et al. .......... 435/190
5,545,545 A 8/1996 Gengenbach et al. ..... 435/172.3

FOREIGN PATENT DOCUMENTS

| EP | 0485970 A2 | 11/1991 |
| WO | WO 96/01905 | 1/1996 |
| WO | WO 96/38574 | 12/1996 |
| WO | WO 97/07665 | 3/1997 |

OTHER PUBLICATIONS

Bork, P. Genome Research, vol. 10, 2000, p. 398-400.*
Lazar et al. Molecular and Cellular Biology, Mar. 1988, vol. 8, No. 3, p. 1247-1252.*
Burgess et al. The Journal of Cell Biology, 1990, vol. 111, p. 2129-2138.*
Broun et al. Science, Nov. 13, 1998, vol. 282, p. 131-133.*
Van Breusegem et al. Plant Physiology. vol. 105, p. 1463-1464, 1994.*
Goodenough, U. Genatics, 2nd edition, Holt, Rinehart and Winston, Pub., p. 322-328, 1978.*
Schroeder et al. Plant Mol. Biol. 33:211-222, 1997; Database UniProt 03, Acc. No. Q96551.*
Hein, J. J. (1990) Meth. Enz. 183:626-645.
Bieleski et al. (1996) Anal. Biochem. 17:278-293.
Farkas et al. (1965) J. Biol. Chem. 240:4717-4722.
Cremer et al. (1988) J. Gen. Microbiol. 134:3221-3229.
Giovanelli et al. (1984) Plant Physiol. 76:285-292.
Curien et al. (1996) FEBS Lett. 390:85-90.
Tomova et al. (1968) Biochemistry (USSR) 33:200-208.
Dougall (1970) Phytochemistry 9:959-964.
Mudd (1960) Biochim. Biophys. Acta 38:354-355.
Boerjan et al. (1994) Plant Cell 6:1401-1414.
Feng, et al, EMBL Sequence Data Library, XP002078204, May 10, 1997.

(Continued)

*Primary Examiner*—Phuong T. Bui

(57) ABSTRACT

This invention relates to an isolated nucleic acid fragment encoding a plant enzyme that catalyze steps in the biosynthesis of lysine, threonine, methionine, cysteine and isoleucine from aspartate, the enzyme a member selected from the group consisting of: dihydrodipicolinate reductase, diaminopimelate epimerase, threonine synthase, threonine deaminase and S-adenosylmethionine synthetase. The invention also relates to the construction of a chimeric gene encoding all or a portion of the enzyme, in sense or antisense orientation, wherein expression of the chimeric gene results in production of altered levels of the enzyme in a transformed host cell.

10 Claims, 18 Drawing Sheets

OTHER PUBLICATIONS

Saito, et al, "Modulation of Cystein Biosynthesis in Chloroplasts of Transgenic Tobacco Overexpressing Cysteine Synthase [O-Acetylserine(thiol)-lyase]", *Plant Physiology*, 106, 1996, 887-895.

Youssefian, et al. "Tobacco Plants Transformed with the O-acetylserine (thiol) lyaseGene of Wheat are Resistant to Toxic Levels of Hydrogen Sulphide Gas", *The Plant Journal* (*1993*), 4, No. 5, 759-769.

Curien, et al, "Characterization of an Arabidopsis Thaliana cDNA Encoding an S-adenosylmethionine Sensitive Threonine Synthase", *EMBL Sequence Data Library*, XP002078253, Jul. 26, 1996.

Espartero, et al, "Differential Accumulation of S-adenosylmethionine Synthetase Transcrpits in Response to Salt Stress", *EMBL Sequence Data Library*, XP002078254, Nov. 23, 1993.

Schwartz, et al, *EMBL Sequence Data Libary*, XP002078255, Jun. 8, 1996.

\* cited by examiner

FIG.2

```
              1                                                          60
SEQ ID NO:4   ............................................................
SEQ ID NO:2   ..........................................KIGRRNAA........
SEQ ID NO:5   MANQDLIPVVVNGAAGKMGREVIKAVAQAPDLQLVGAVDHNPSLQGQDIGEVVGIAPLEV 61                                                         120
SEQ ID NO:4   ......KVLCSTQMPPSQSTI.....KVVIIGATKEIGRTAIAAVSKARGMELAGAID.
SEQ ID NO:2   PVLNDLTMVLGSIAQSRATGVVVDFESEPSAVYDNVKQAAAFGLSSVVYPKIELETVTEL
SEQ ID NO:5   PVLADLQSVLVLATQEKIQGVMDFTHPSGVYDNVRSAIAYGVRPVVGTTGLSEQQIQDL 121                                                        180
SEQ ID NO:4   ......S.QCI...GLDAGEI.................................SGMGRTLEIPV.
SEQ ID NO:2   SAFCEKAS.GCLVAPTLSIGSVLLQQAAIQASFHYSNVEIVESRPNP.SDLPSQDAIQIA
SEQ ID NO:5   GDFAEKASTGCLIAPNFAIGVLLMQQAAVQACQYFDHVEIIELHRNQKADAPSGTAIKTA 181                                                        240
SEQ ID NO:4   ..LNDLTMV......LGSIAQTRA..................TGVV....VDFSEPSTVYD
SEQ ID NO:2   NNISDLGQIYNR...EDMDSSSPARGQLLGEDGVRVHSMVLPGLVSSTSINFSGPGEMYT
SEQ ID NO:5   QMLAEMGKTFNPPAVEEKETIAGAKGGL.GPGQIPIHSIRLPGLIAHQEVLFGSPGQLYT 241                              276
SEQ ID NO:4   NVKQA.............................
SEQ ID NO:2   LRHDVANVQCLMPGLILAIRKVVRFKNLIYGLEKFL
SEQ ID NO:5   IRHDTTDRACYMPGVLLGIRKVVELKGLVYGLEKLL
```

Fig. 3A

```
                        1                                                           60
SEQ ID NO: 7    L...........................................................
SEQ ID NO: 9    VS..........................................................
SEQ ID NO:11    MAITATISVPLTSPSRRTLTSVNSLSPLSTRSTLPTPQRTFKYPNSRLVVSSMSTETAVK
SEQ ID NO:13    ............................................................
SEQ ID NO:14    ............................................................

61                                                          120
SEQ ID NO: 7    ............................................................
SEQ ID NO: 9    ....................................................GADGV
SEQ ID NO:11    TSSASFLNRKESGFLHFAKYHGLGNDFVLIDNRDSSEPKISAEKAVQLCDRNFGVGADGV
SEQ ID NO:13    ...............ALHFVKYQGLGNDFIMVDNRDSAVPKVTPEEAAKLCDRNFGXGADGV
SEQ ID NO:14    ...............MALSFSKYHGLGNDFILVDNRQSTEPCLTPDQAQQLCDRHFGIGADGV 121                                                         180
SEQ ID NO: 7    ...................PEMCGNGVRCFARFIAEIENLQGTNRFTIHTGAGKIV
SEQ ID NO: 9    IFVMPGVNGADYTMRIFNSDGSEPEMCGNGVRCFARFIAELENLQGTHSFKIHTGAGLII
SEQ ID NO:11    IFVLPGISGTDYTMRIFNSDGSEPEMCGNGVRCFARFIAELENLQGTHSFKIHTGAGLII
SEQ ID NO:13    IFVLPGVNGADYTMRIFNSDGSEPEMCGNGVRCFAKFVSQLENLHGRHSFTIHTGAGLII
SEQ ID NO:14    IFALPGQGGTDYTMRIFNSDGSEPEMCGNGIRCLAKFLADLEGVEEK.TYRIHTLAGVIT 181                                                         240
SEQ ID NO: 7    PEIQSDGQVKVDMGEPILSGLDIPTKLLATKNKAVVQAELAVEGLTWHVTCVSMGNPHCV
SEQ ID NO: 9    PEIQNDGKVKVDMGQPILAC........................................
SEQ ID NO:11    PEVLEDGNVRVDMGEPVLKALDVPTKLPANKDNAVVKSQLVVDGVIWHVTCVSMGNPHCV
SEQ ID NO:13    ............................................................
SEQ ID NO:14    PQLLADGQVKVDMGEPQLLAELIPTTLAPAGEK.VVDLPLAVAGQTWAVTCVSMGNPHCL
```

Fig. 3B

```
                  241                                                         300
SEQ ID NO: 7      TFGANELKVLQVDDLKLSEIGPKFEHHEMFPARTNTEFVQVLSRSHLKMRVWERGAGATL
SEQ ID NO: 9      ............................................................
SEQ ID NO:11      TFSREGSQNLLVDELKLAEIGPKFEHHEVFPARTNTEFVQVLSNSHLKMRVWERGAGATL
SEQ ID NO:13      ............................................................
SEQ ID NO:14      TFVDD.....VDSLNLTEIGPLFEHHPQFSQRTNTEFIQVLGSDRLKMRVWERGAGITL 301                                              359
SEQ ID NO: 7      ACGTGACACAVVVAAVLEGRAERKCVVDLPGGPLEIEWREDDNHVYMTGPAEVVFYGSVVH
SEQ ID NO: 9      ............................................................
SEQ ID NO:11      ACGTGACACATVVAAVLEGRAGRNCTVDLPGGPLQIEWREEDNHVYMTGSADVVYYGSLPL
SEQ ID NO:13      ............................................................
SEQ ID NO:14      ACGTGACACATVVAAVLTGRGDRRCTVELPGGNLEIEWSAQDNRLYMTGPAQRVFSGQAEI
```

Fig. 4A

```
                1                                                            60
SEQ ID NO:24    ................................................................
SEQ ID NO:26    ASSSLFQSLPFSLQTSK.PYAPPKPAAHFVVRA......QSPLTQNNNSSSKHRRPAD
SEQ ID NO:27    LSSCLFNASVSSLNPKQDPIRRHRSTSLLRHRPVVISCTADGNNIKAPIETAVKPPHRTE 61                                                          120
SEQ ID NO:20    ................................................................
SEQ ID NO:22    ................................................................
SEQ ID NO:24    ...........................................MENGAATNGASEKSHSPS
SEQ ID NO:26    ENIRDEARRINAPHDHHLFSAKYVPFNADSSSSSSTESYSLDEIVYRSQSGGLLDVQHDM
SEQ ID NO:27    DNIRDEARR.NRSNAVNPFSAKYVPFNA...APGSTESYSLDEIVYRSRSGGLLDVEHDM 121                                                         180
SEQ ID NO:16    ................................................................
SEQ ID NO:18    ................................................................
SEQ ID NO:20    QTYLSTRGDDYGLSFETVV.............................................
SEQ ID NO:22    ................................................................
SEQ ID NO:24    DALKRFDGEYWRNLFDSRVGKTTWPYGSGVWSKKEWVLPEIHDDDIVSAFEGNSNLFWAE
SEQ ID NO:26    ................................................................
SEQ ID NO:27    EALKRFDGAYWRDLFDSRVGKSTWPYGSGVWSKKEWVLPEIDDDDIVSAFEGNSNLFWAE 181                                                         240
SEQ ID NO:16    ...........................................VGCASTGDTSA
SEQ ID NO:18    ................................................................
SEQ ID NO:20    LKGLAADGGLFLPEEVPAATEWQSWKDLPYTELAVKV............................
SEQ ID NO:22    ................................................................
SEQ ID NO:24    RFGKQFLGMNDLWVKHCGISHTGSFKDLGMTVLVSQVNRLRKVMNRPVVGVGCASTGDTSA
SEQ ID NO:26    ................................................................
SEQ ID NO:27    RFGKQFLGMNDLWVKHCGISHTGSFKDLGMTVLVSQVNRLRKMKRPVVGVGCASTGDTSA
```

Fig. 4B

```
              241                                                          300
SEQ ID NO:16  ALSAYCAAAGIPAIVFLPADRISLQQLIQPIANGATVLSLDTDFDGCMRLIREVTAELPI
SEQ ID NO:18  .LSLYISPAEVPTE........DLRALVER..............................
SEQ ID NO:20  ............................................................
SEQ ID NO:22  ALSAYCASAAIPSIVFLPANKISLAQLVQPIANGAFVLSIDTDFDGCMQLIREVTAELPI
SEQ ID NO:24  ......................LIQPIANGATVLSLDTDFDGCMRLIREVTAELPI
SEQ ID NO:26  ............................................................
SEQ ID NO:27  ALSAYCASAGIPSIVFLPANKISMAQLVQPIANGAFVLSIDTDFDGCMKLIREITAELPI 301                                                          360
SEQ ID NO:16  YLANSLNPL.RLEGQKTAAIEILQQFNWQVPDWVIVPGGNLGNIYAFYKGFEMCRVLGLV
SEQ ID NO:18  ............................................................
SEQ ID NO:20  ..............SYSTFRSKEVVPLVKLEDNLHLLELFHGPNYSF..............
SEQ ID NO:22  YLANSLNSL.KLEGQKTAAIEILQQFDWQVPDWVIVPGSNLGNIYAFYKGFKMFQELGLV
SEQ ID NO:24  YLANSLNSL.XLEGQKTAAIRDIATXNWQVPGLGHIPRRQSXTFYAFLQGF..........
SEQ ID NO:26  ............................................................
SEQ ID NO:27  YLANSLNSL.RLEGQKTAAIEILQQFDWQVPDWVIVPGGNLGNIYAFYKGFKMCQELGLV 361                                                          420
SEQ ID NO:16  DRVPRLVCAQAANANPLYRYYKSGWTEFEPQTAETTFASAIQIGDPVSVDRAVVALKATD
SEQ ID NO:18  ............................................................
SEQ ID NO:20  ............................................................
SEQ ID NO:22  DKIPRLVCAQAANADPLYLYFKSGWKEFKPVKSSTTFASAIQIGDPVSIDRAVHALKSCD
SEQ ID NO:24  ..................KDCALQFLGNLXEYF...........................
SEQ ID NO:26  ............................................................
SEQ ID NO:27  DRIPRMVCAQAANANPLYLHYKSGWKDFKPMTASTTFASAIQIGDPVSIDRAVYALKKCN
```

Fig. 4C

```
                 421                                                           480
SEQ ID NO:16     GIVEEATEEELMDATALADRTGMFACPHTGVALAALFKLQGQRIIGPNDRTVVVSTAHGL
SEQ ID NO:18     ............................................................
SEQ ID NO:20     ..........DAMVQADSTGMFICPHTGVALAAALIKLRNRGVIGAGERVVVVSTAHGL
SEQ ID NO:22     ..........DAMVQADSTGMFICPHTGVALTALFKLRNSGVIKATDRTVVVSTAHGL
SEQ ID NO:24     GIVEEATEEELMDAMAQADSTGMFICPHTGVALTALFKLRNQGVIAPTDRTVVVSTAHGL
SEQ ID NO:26     ............................................................
SEQ ID NO:27     GIVEEATEEELMDAMAQADSTGMFICPHTGVALTALFKLRNQGVIAPTDRTVVVSTAHGL 481                                                           537
SEQ ID NO:16     KFTQSKIDYHDKNIKDMVCQYANPPISVKADFGSVMDVLQKN........LNGKI....
SEQ ID NO:18     ...................MACKYSNPPVSVKADFGAVMDVLKKR........LKGKL....
SEQ ID NO:20     KFAQSKIDYHSGLIPGMG.RYANPLVSVKADFGSVMDVLKDSCTTSPPTLTSLDVAK
SEQ ID NO:22     KFTQSKIDYHSKDIKDMACRYANPPMQVKADFGSVMDVLKTY........LQSKA..H
SEQ ID NO:24     ............................................................
SEQ ID NO:26     ............................................................
SEQ ID NO:27     KFTQSKIDYHSNAIPDMACRFSNPPVDVKADFGAVMDVLKSY........LGSNTLTS
```

Fig. 5A

```
SEQ ID NO:29        1  ......................................................
SEQ ID NO:31           ......................................................
SEQ ID NO:33           ......................................................
SEQ ID NO:34           MASHDYLKKILTARVYDVAFETELEPARNLSARLRNPVYLKREDNQPVFSFKLRGAYNKM  60

SEQ ID NO:29       61  ......................................................
SEQ ID NO:31           ......................................................
SEQ ID NO:33           ..................................................TVVLEGD
SEQ ID NO:34           AHIPADALARGVITASAGNHAQGVAFSAARMGVKAVIVVPVTTPQVKVDAVRAHGGPGVE  120

SEQ ID NO:29      121  SYDEAQSYAK.....LRCQQE.GRTFVPPFDHPDVITGQGTIGMEIVRQLQGPLHAIFVP
SEQ ID NO:31           ......................................................
SEQ ID NO:33           ......................................................
SEQ ID NO:34           VIQAGESYSDAYAHALKVQEERGLTFVHPFDDPYVIAGQGTIAMEILRQHQGPIHAIFVP  180

SEQ ID NO:29      181  VGGGGLIAGIAAYVKRVRPEVKIIGVEPSDANAMALSLCHGKRVMLEHVGGFADGVAVKA
SEQ ID NO:31           ......................................................
SEQ ID NO:33           ......................................................
SEQ ID NO:34           IGGGGLAAGVAAYVKAVRPEIKVIGVQAEDSCAMAQSLQAGKRVELAEVGLFADGTAVKL  240

SEQ ID NO:29      241  VGEETFRLCRELVDGIVMVSRDAICASIKDMFEEKRSILEPAGALALAGAEAYCKYYNLK
SEQ ID NO:31           ......................................................
SEQ ID NO:33           ......................................................
SEQ ID NO:34           VGEETFRLCKEYLDGVVTVDTDALCAAIKDVFQDTRSVLEPSGALAVAGAKLYAEREGIE  300
```

Fig. 5B

```
              301                                                         360
SEQ ID NO:29  GETVVAITSGANMNFDRLRLVTELADVGRKREAVLATFLPERQGSFKKFTELVGRMNITE
SEQ ID NO:31  ..NIVAITSGANMNFDKLRVVTELANVGRKQEAVLATVMAEEPGSFKQFCELVGQMNITE
SEQ ID NO:33  ............................................................
SEQ ID NO:34  NQTLVAVTSGANMNFDRMRFVAERAEVGEAREAVFAVTIPEERGSFKRFCSLVGDRNVTE 361                                                         420
SEQ ID NO:29  FKYRYDSNAKDALVLYSVGIYTDNELGAMMDRMESAKLRTVNLTDNDLAKDHLRYFIGGR
SEQ ID NO:31  FKYRYNSNEK.AVVLYSVGVHTISELRAMQERMESSQLKTYNLTESDLVKDHLRYLMGGR
SEQ ID NO:33  ............................................................
SEQ ID NO:34  FNYRI.ADAQSAHIFVGVQIRRGESADIAANFESHGFKTADLTHDELSKEHIRYMVGGR 421                                                         480
SEQ ID NO:29  SEIK.DELVYRFIFPERPGALMKFLDTFSPRWNISLFHYRAQGEAGANVLVGIQVPPAEF
SEQ ID NO:31  SNVQ.NEVFVVSPXPRKTGALMKFLDXFSPRWDISL........................
SEQ ID NO:33  .........RPGALMKFLDPFSPRWNISLFHYRGEGETGANVLVGIQVPKSEM
SEQ ID NO:34  SPLALDERLFREFPERPGALMKFLSSMAPDWNISLFHYRNQGADYSSILVGLQVPQADH 481          512
SEQ ID NO:29  DEFKSHANNLGYEYMSEHNNEIYRLLLRDPKV
SEQ ID NO:31  ................................
SEQ ID NO:33  DEFHDRANKLGYDYKVVNNDDFQLLMH.....
SEQ ID NO:34  AEFERFLAALGYPYVEESANPAYRLFLS....
```

Fig. 6A

```
SEQ ID NO:36    126  GCAGATCAAAGAAGATGGCAGCTCTCTGACACCTTCCTCTCTTCACCTCGGAGTCTCTGTGAACG  185
                     ||||||||  |||||||||||||||||||||||  ||||| |||  ||| ||||||||||||||
SEQ ID NO:37    774  GCAGATAGGAGAAGATGGCCGCGGCACTTGATACCTTCCTCTTTACCTCGGAGTCTCTGTGAACG  833

SEQ ID NO:36    186  AGGGACACCCTGACAAGCTCTGCGACCAGTCTCAGATGCCGTTCTTGACGCTTGCCTTG  245
                     ||||  ||||||||||||||||| |||||||||||||||  |||||||| ||||||||
SEQ ID NO:37    834  AGGGCCACCCTGACAAGCTCTGCCACCAGTCTCAGATGCTGTTCTTGATGCTTGCCTCG  893

SEQ ID NO:36    246  CTGAGGACCCTGACAGCAAGGTTGCTTGTGAGACCTGCACCAAGACCAACATGGTCATGG  305
                     |||||||||||||||||||||| |||||||||||||||||||||||| ||||||||||||
SEQ ID NO:37    894  CCGAGGACCCTGACAGCAAGGTCGCTTGTGAGACCTGCACCAAGACAAACATGGTCATGG  953

SEQ ID NO:36    306  TCTTTGGTGAGATCACCACCAAGGCCAATGTCGACTACGAGAAGATTGTCAGGGAGACCT  365
                     ||||||||||||||||||||||||||  ||||||| ||||||||||||||||||||||
SEQ ID NO:37    954  TCTTTGGTGAGATCACCACCAAGGCTAACGTTGACTATGAGAAGATTGTCAGGGAGACAT  1013

SEQ ID NO:36    366  GCCGCAACATTGGTTTTGTGTCAAACGATGTCGGGCTTGACGCTGACCACTGCAAGGTGC  425
                     |||| ||||||||||| ||||| ||||||||||| ||||||||||||||||||||||||
SEQ ID NO:37    1014 GCCGTAACATCGGTTTTGTGTCAGCTGATGTCGGTCTCGATGCTGACCACTGCAAGGTGC  1073

SEQ ID NO:36    426  TCGTGAACATTGAGCAGCAGTCCCCTGATATTGCTCAGGGTGTGCATGGCCACTTCACCA  485
                     | |||||||| ||||||||||||||| |||||||||||||||||| |||||||||||||
SEQ ID NO:37    1074 TTGTGAACATCGAGCAGCAGTCCCCTGACATTGCACAGGGTGTGCACGGGCACTTCACCA  1133

SEQ ID NO:36    486  AGCGCCCCGAGGAGATTGGAGCTGGTGACACATGTTCGGACCGATG  545
                     |||||||||||||||||| |||||||||||||||  ||| |||||
SEQ ID NO:37    1134 AGCGCCCTGAGGAGATTGGTGCTGGTGACACATGTTTGGATATGCAACTGATG  1193
```

Fig. 6B

```
SEQ ID NO:36    546  AGACCCCTGAGTTGATGCCCCTCAGCCATGTCCTTGCCACCAAGCTAGTGCTGCTCGTCTCA   605
                     ||||||||||||||||||||||||||||||||||||||||||||||||||||||||||||||
SEQ ID NO:37   1194  AGACCCCTGAGTTGATGCCCCTCAGCCATGTCCTTGCTACCAAGCTTGGCGCTCGTCTTA   1253

SEQ ID NO:36    606  CCGAGGTCCGCAAGAACGGAAACCTGCCCCTGGCTCAGGCCTGATGGAAGACCCAGGTGA    665
                     ||||||||||||||||||||||||||||||||||||||||||||||||||||||||||||
SEQ ID NO:37   1254  CGGAGGTTCGCAAGAATGGGACCTGCGCATGGCTCAGGCCTGACGGAAGACCCAAGTGA   1313

SEQ ID NO:36    666  CAGTCGAGTACCGCAATGAGGGTGGTGCCATGGTCTCCCATCCGTGTCCACACCGTCCTCA   725
                     ||||||||||||||||||||||||||||||||||||||||||||||||||||||||||||
SEQ ID NO:37   1314  CTGTTGAGTACCGCAATGAGAGCGGTGCCAGGGTCCCTGTCCCACACCGTCCTCA   1373

SEQ ID NO:36    726  TCTCCACCCAGCAGCACGAGAGACAGTGACCAATGATGAGATCGCTGCTGACCTGAAGGAGC   785
                     ||||||||||||||||||||||||||||||||||||||||||||||||||||||||||||
SEQ ID NO:37   1374  TCTCTACCCAGCATGATGAGACAGTCACCAACGATGAGATTGCTGCTGACCTGAAGGAGC   1433

SEQ ID NO:36    786  ATGTCATCATCAAGCCTATCATCCCTGAGCAGTAGTACCTTGACGAGAAGACCATCTTCCACCTTA   845
                     ||||||||||||||||||||||||||||||||||||||||||||||||||||||||||||
SEQ ID NO:37   1434  ATGTCATCATCAAGCCTGTCATTCCCGAGCAGTAGTACCTTGATGAGAAGACAATCTTCCATCTTA   1493

SEQ ID NO:36    846  ACCCATCCGGCGCTTTGTCGCTTCACGGCCGATGCTGGCCTCACTGGCCGCA    905
                     ||||||||||||||||||||||||||||||||||||||||||||||||||||
SEQ ID NO:37   1494  ACCCATCTGGTCGCTTCGTCGCTTCATGGCGGACCTCATGGTGCTGGTCTCACTGGCCGGA   1553

SEQ ID NO:36    906  AGATCATCATTGACACCTACGGTGGCTGGGAGCCCATGGCGGTGGCGTTTCTCCGGCA    965
                     ||||||||||||||||||||||||||||||||||||||||||||||||||||||||||
SEQ ID NO:37   1554  AGATCATCATTGACACTTATGGTGGCTGGGGAGCTCACGGTGGTGTGCCTTCTCTGCA   1613
```

Fig. 6C

```
SEQ ID NO:36   966 AGGACCCAACCAAGGTTGACCGCAGCGGAGCCTATGTCGCGAGGCAGGCTGCCAAGAGCA 1025
                   ||||||||||||||||||||||||||||||||||| ||||||||||||||||||||||||
SEQ ID NO:37  1614 AGGACCCAACCAAGGTTGACCGCAGTGGAGCATACGTCGCAAGGCAAGCTGCCAAGAGCA 1673

SEQ ID NO:36  1026 TCGTCGCCAGCGGGCCTTGCTCGCCGCCAGTCGTCCAGGTGTCTCCAGCCATCGGCGTGC 1085
                   |||||||||||||||| |||||||| ||||| ||||||| ||||| | ||||||||| |
SEQ ID NO:37  1674 TTGTTGCTAGTGGCCTTGCTCGCCGCTGCTTGTCATTGTCCAAGTATCATACGCCATCGGTGTCC 1733

SEQ ID NO:36  1086 CCGAGCCCTCTCTCCGTGTTTGTCGACAGAACTTCGATTTCAGGCCTGGCACCGGCGCGA 1145
                   |||||||||| ||||| ||| ||||| || ||||||||||||||| ||||||||||| |
SEQ ID NO:37  1734 CAGAGCCACTGTCCGTATTCGTCGACACATACGGCACTGGCAGGATCCCTGACAAGGAGA 1793

SEQ ID NO:36  1146 TCCTCAAGATTGTCAAGGAGAACTTCGATTTCAGGCCTGGCATGATTATCATCAACCTTG 1205
                   |||||||||||| ||||||||||||||||||||||||||||||||||||||||||||||
SEQ ID NO:37  1794 TCCTCAAGATTGTGAAGGAGAACTTCGACTTCAGGCCTGGCATGATCATCATCAACCTTG 1853

SEQ ID NO:36  1206 ACCTCAAGAAAGGCGGCAACGGCGCTACCTCAAGACGGCAGCCTACGGCCACTTCGGAA 1265
                   |||||||||||||||||||||||||||||||||||||||||||||||| || |||||||
SEQ ID NO:37  1854 ACCTCAAGAAAGGCGGCAACGACGCTACCTCAAGACGGCGCTTACGGTCACTTCGGAA 1913

SEQ ID NO:36  1266 GGGACGACCCTGACTTCACCTGGGAGGTGTGAAGCCACTCAAGTCGGAGAAACCTTCTG 1325
                   ||||||||| ||| ||||||| |||||||| |||||| ||| ||| ||||||||| |||
SEQ ID NO:37  1914 GGGACGACCCAGACTTCACCTGGGAGGTGGTGAAGCCCCTCAAGTGGGAGAAGCCTTCTG 1973

SEQ ID NO:36  1326 CCTAAGGCGGCCTTTT 1341
                   ||||| ||  |||||
SEQ ID NO:37  1974 CCTAAAAGCTCCCTTT 1989
```

Fig. 7A

```
SEQ ID NO:38   80  GAGACATTCCTATTTACCTCAGAGTCAGTGAACGAGGGACACCCTGACAAGCTCTGCGAC  139
                   ||||||||||| || |||||| ||||| |||||||||||||| ||||||||||||| ||
SEQ ID NO:40  123  GAAACTTTCTTATTCACCTCCGAGTCTCTGTGAACGAGGAGGGTCACCCAGACAAGCTCTGTGAT  182

SEQ ID NO:38  140  CAAATCTCCGATGCTGTCCTCGACGCTTGCCTTGAACAGGACCCAGACAGCAAGGTTGCC  199
                   |||||||| ||||| |||||| || |||||||||| |||| ||||| |||||||||||
SEQ ID NO:40  183  CAGATCTCTGATGCAGTTCTTGATGCTTGCCTTGAGCAGGATCCCGAGCAAGAAAGTTGCA  242

SEQ ID NO:38  200  TGCGAAACATGCACCAAGACCAACTTGGTCTCTTCGGAGAGATCACCACCAAGGCC  259
                   || |||| |||||||||||||||||||||||| |||||||||| |||||||||||
SEQ ID NO:40  243  TGTGAAACTTGCACCAAGACCAACTTGGTCTTTGGTGAGATCACAACCAAGGCT  302

SEQ ID NO:38  260  AACGTTGACTACGAGAAGATCGTGCGTGACACCTGCAGGAACATCGGCTTCGTCTCTCAAAC  319
                   | ||| |||||||| |||| |||||||||||||| ||||||||||||| |||||| |||
SEQ ID NO:40  303  ATTGTAGACTATGAGAAGATTGTGCGTGACACATGCCGTAATATTGGATTTGTTTCTGAT  362

SEQ ID NO:38  320  GATGTGGGACTTGATGCTGACAACTGCAAGGTCCTTGTAAACATTGAGCAGCAGAGCCCT  379
                   ||||| |||||||||||| |||||||||||||| || |||||||||||||||| | ||
SEQ ID NO:40  363  GATGTTGGTCTTGATGCTTGACAACTGCAAGGTCCTTGTTTACATTGAGCAGCAAAGTCCT  422

SEQ ID NO:38  380  GATATTGCCCAGGGTGTGCACGGCCACCTTACCAAAAGACCCGAGGAAATCGGTGCTGGA  439
                   |||| ||| ||||| ||||| || ||||| |||||| ||||| |||| ||||||||
SEQ ID NO:40  423  GATATTGCTCAAGGTGTCCACGGCCATCTGACCAAACGCCCCGAGGAGATTGGTGCTGGT  482

SEQ ID NO:38  440  GACCAGGGTCACATGTTTGGCTATGCCACGGACGAAACCCCAGAATTGATGCCATTGAGT  499
                   |||||||| |||||||||||||||| || |||||||| ||||||||||||||| |||
SEQ ID NO:40  483  GACCAGGGCCACATGTTTGGCTATGCAACAGATGAGAGACCCTGAATTAATGCCTCTCAGT  542
```

Fig. 7B

```
SEQ ID NO:38   500  CATGTTCTTGCAACTAAACTCGGTGCTCGTCTCTCACCGAGGTTCGCAAGAACGGAACCTGC  559
                    ||||| |||||||||||||||||||| |||||||| |||||||||||||||| |||||||
SEQ ID NO:40   543  CACGTGCTTGCAACTAAACTTGGTGCCCGTCTTACAGAAGTCCGCAAGAATGGCACCTGC   602

SEQ ID NO:38   560  CCATGGTTGAGGCCTGATGGGAAAACCCAAGTGACTGTTGAGTATTACAATGACAACGGT   619
                    |||||||||||||||||||| ||||||||||||||||||||||| |||||||||||||||
SEQ ID NO:40   603  GCCTGGTTGAGGCCTGATGGCAAGACCCAAGTGACTGTTGAGTATAGCAATGACAATGGT   662

SEQ ID NO:38   620  GCCATGGTTCCAGTTCGTGTCCACACTGTGCTTATCTCCACCAACATGATGAGACTGTG   679
                    |||||||||||||||||||||||||  |||||||||||||||||||||||||||||  |
SEQ ID NO:40   663  GCCATGGTTCCAATTAGGGTACACACTGTGTTCTTATCTCCACCAACACGATGAGACCGTT  722

SEQ ID NO:38   680  ACCAACGACGAAATTGCAGCTGACCTCAAGGAGCATGTGATCAAGCCGGTGATCCCGGAG  739
                    |||||| ||||||||||||||||  ||||||||||||||||| ||||||||||||||||
SEQ ID NO:40   723  ACCAATGATGAGATTGCCCGCGACCTTAAGGAGCATGTCATCAAACAACCAGTCATCCCAGAG  782

SEQ ID NO:38   740  AAGTACCTTGATGAGAAGACCATTTTCCACTTGAACCCCTCTGGCCGTTTTGTCATTGGA  799
                    ||||||||||||||||||| ||| || |||||| |||||||||| |||| ||| ||
SEQ ID NO:40   783  AAGTACCTTGATGAGAATACTATTTTCCACCTTAACCCATCCATCTGGCCGATTCGTCGTTATTGGT  842

SEQ ID NO:38   800  GGTCCTCACGGTGATGCTGGTCTCCACCGGCCGCAAGATCATCATCGATACTTACGGAGGA  859
                    ||| ||||||||||||||||||||||||||||||||||| ||| ||||| |||||||||
SEQ ID NO:40   843  GGACCTCATGGTGATGCTGGTCTCCACTGGTCGTCGTAAAATCATCATGACACTTATGGTGGT  902

SEQ ID NO:38   860  TGGGGTGCTCATGGTGGTGGTGCTTTCTCCGGAAGGATCCCACCAAGGTTGATAGGAGT   919
                    |||||||||||||||||||||||||||||||||| |||||||||||||||||| ||||||
SEQ ID NO:40   903  TGGGGTGCTCATGGTGGTGGTGCTTTCTCGGGGGCAAAGAGACCCAACCAAGGTGACAGGAGT   962
```

Fig. 7C

```
SEQ ID NO:38   920 GGTGCTTACATTGTGAGACAGGCTGCTAAGAGCATTGTGGCAAGTGGACTAGCCAGAAGG   979
                      ||||||||||||||||||||||||||||||||||||||||||||||||||||||||||
SEQ ID NO:40   963 GGTGCATACATTGTAAGGCAGGCTGCAAAGAGTATCGTAGCTAGTGGACTTGCTCGTAGA  1022

SEQ ID NO:38   980 TGCATTGTGCAAGTGTCTTATGCCATTGGTGTGCCCGAGCCTTTGTCTGTCTTTGTTGAC  1039
                      ||||||||||||||||||||||||||||||||||||||||||||||||||||||||||
SEQ ID NO:40  1023 TGCATCGTGCAGGTATCTTATGCCATCGGTGTGCCTGAGCCATTGTCTGTCTATTCGTTGAC  1082

SEQ ID NO:38  1040 ACCTATGGCACCGGGAAGATCCATGATAAGGAGATTCTCAACATTGTGAAGGAGAACTTT  1099
                      ||||||||||||||||||||||||||||||||||||||||||||||||||||||||||
SEQ ID NO:40  1083 ACCTATGGCACTGGGAAAGATCCCTGACAGGGAAAATTTTGAAGATCGTTAAGGAGAACTTT  1142

SEQ ID NO:38  1100 GATTTCAGGCCCCGGTATGATCTCCATCAACCTTGATCTCAAGAGGGGTGGGAATAACAGG  1159
                      ||||||||||||||||||||||||||||||||||||||||||||||||||||||||||
SEQ ID NO:40  1143 GACTTCAGACCTGGAATGATGTCCATTAACTTGGATTTGAAGAGGGGTGGCAATAGAAGA  1202

SEQ ID NO:38  1160 TTCTTGAAGACTGCTGCATATGGACACTTCGGCAGAGAGGACCCCTGACTTCACATGGGAA  1219
                      ||||||||||||||||||||||||||||||||||||||||||||||||||||||||||
SEQ ID NO:40  1203 TTCTTGAAAAACTGCTGCCTATGGTCACTTTGGACGTGATGACCCCGATTTCACATGGGAA  1262

SEQ ID NO:38  1220 GTGGTCAAGCCCCTCAAGTGGGAGAAGGCCATTCATTCCACTGCAATGTGCTG  1279
                      |||||||||||||||||||||||||||||||||||||||||||||||||||
SEQ ID NO:40  1263 GTTGTCAAGCCCCCTCAAAGTGGGAAAAAGCCCCAAGACTAATAAGTGCTTGCCTATGTTTTT  1322

SEQ ID NO:38  1280 GGAGTTTTTT  1289
                      |||  |||
SEQ ID NO:40  1323 GTTCTTTGTT  1332
```

Fig. 8A

```
SEQ ID NO:42    41 AGCAGCGCAAGGGCATCGCTAGCACTAAAGAAATGGCAGCCGAGACGTTCCTCTTCACGT 100
                   |||||||||||||||| ||| || |||||||||||||||||||||||||||||||||||
SEQ ID NO:43    23 AACTGCACGAGAGCATCTCTACCACCAAAGAAATGGCGGCCGAGACGTTCCTCTTCACGT  82

SEQ ID NO:42   101 CCGAGTCTGTGAACGAGGGCCATCCGACCAAGCTCTGTGACCAAGTCTCCGACGCCGTCT 160
                   |||||||||||||||||||||||||||||||||||||||||||||||||||||||||||
SEQ ID NO:43    83 CCGAGTCCGTGAACGAGGGCCATCCGACCAAGCTGTGCGACCAGTCTCTGACGCCGTCT  142

SEQ ID NO:42   161 TGGATGCCTGCTTGGCCCAGGATGCCGACAGCAAGGTCGCCTGCGAGACCGTCACCAAGA 220
                   |||| |||||||||||||||||||||||||||||||||| || ||||||| ||||||||
SEQ ID NO:43   143 TGGACGCCTGCTTGGCCCAGGATCCTGACAGCAAGGTTGCTTGCGAGACCTGCACCAAGA 202

SEQ ID NO:42   221 CCAACATGGTCATGGTCTTGGGCGAGATCACCACCAAGGCCACCGTGACTATGAGAAGA 280
                   ||||||||||||||||||||||||||||||||||||||||||||||||||||||||||
SEQ ID NO:43   203 CCAACATGGTCATGGTCTTCGGCGAGATCACCACCAAGGCCACCGTTGACTATGAGAAGA 262

SEQ ID NO:42   281 TCGTGCGCGTGACACCTGCCGCAACATCGGTTTCATCTCTGATGACGTTGGTCTCGACGCCG 340
                   || |||||||||| |||||||||||||||||||||||||||||||| ||||||||| |||
SEQ ID NO:43   263 TTGTGCGCGACACCTGCCGCAACATCGGCTTCATCTCTGACGACGTCGGTCTCGATGCCG 322

SEQ ID NO:42   341 ACCGTTGCAARGTGCTCGTCAACATGAGCAGTCCCCTGACATTGCCAGGGTGTTC 400
                   || ||||||||| ||||||||||||||||||||||||||||||||||||||||||||
SEQ ID NO:43   323 ACCATTGCAAGGTGCTCGTCAACATGAGCAGCAATCCCCTGACATTGCCAGGGTGTTC  382

SEQ ID NO:42   401 ATGGACACTTCACCAAGCGTCCCGAAGAAGTCGGCGCGGTGACCAGGGCATCATGTTCG 460
                   ||||||||||||||||||||| ||||||||||||||||||||||||||||||||||||
SEQ ID NO:43   383 ACGGACACTTCACCAAGCGTCCAGAGAAGAGGTCGGCGCGGTGACCAGGGCATCATGTTTG 442

SEQ ID NO:42   461 GCTATGCCACCGATGAGACCCCTGAGCTGATGCCCTCAAGCACGTGCTTGCCACCAAGC 520
                   |||| ||||||||||||||||||||||||||||||||||||||||||||||||||||||
SEQ ID NO:43   443 GCTACGCCACTGATGAGACCCCTGAGCTGATGCCCCTCACCCACATGCTTGCCACCAAGC 502
```

Fig. 8B

```
SEQ ID NO:42   521 TYGGAGCTCGCCTCACSGAGGTCCGCAAGAATGGCACCTGCGCCTGGGTCAGGCCTGACG 580
                      ||| ||||||||||| |||||||||||||||||||||||||||||||||||||||||
SEQ ID NO:42   503 TCGGAGCTCGCCTCACCGAGGTCCGCAAGAATGGCACCTGCGCCTGGCTCAGGCCTGATG 562

SEQ ID NO:42   581 GAAAGACCCAGGTCACAGTCGAGTACCTAAACGAGGATGGTGCCATGGTACCTGTTCGTG 640
                   |||||||||||||||| ||||||||||| ||||| | ||||||||||||| || |||||
SEQ ID NO:43   563 GAAAGACCCAGGTCACCATTGAGTACCTAAACGAGGGTGGTGCCATGGTGCCCGTTCGTG 622

SEQ ID NO:42   641 TGCACACCGTCCTCATCTCCACCCAGCACGACGAGACCGTCACCAACGACGAGATTGCTG 700
                   |||||||||||||||||||||||||||| ||||||||||||||||||||| |||| |||
SEQ ID NO:43   623 TGCACACCGTCCTCATCTCCACCCAGCATGATGAGACCGTCACCAACGATGAGATCGCTG 682

SEQ ID NO:42   701 CGGACCTCAAGGAGCATGTCATCAAGCCGGTGATCCCCGCAAAGTACCTCGATGAGAACA 760
                   |||||||||||||||||||||||||||||||||||| ||| |||||||||||||||||| 
SEQ ID NO:43   683 CAGACCTCAAGGAGCATGTCATCAAGCCGGTGATTCCCGGAAGTACCTCGATGAGAACA 742

SEQ ID NO:42   761 CCATCTTCCACCTGAACCCGTCTGGCCGCTTCGTCATCGGCGGGCCCCCACGGTGACGCCG 820
                   |||||||||||||||||||||||||| |||||||||||||||| |||| ||||| |||||
SEQ ID NO:43   743 CCATCTTCCACCTGAACCCGTCTGAACCCATCGGGCCGCTTTGTCATCGGCTGGCCCTCACGGCGATGCCG 802

SEQ ID NO:42   821 GTCTCACCGGCCGCAAGATCATCATCGACACCTATGGTGGCTGGGAGCCCACGGCGGCG 880
                   |||||||||||||||||||||||||||||||||||||||||||||||||||||||||||
SEQ ID NO:43   803 GTCTCACCGCCCCGCAAGATCATCATCGACACCTATGGTGGCTGGGAGCCCACGGCGGCG 862

SEQ ID NO:42   881 GTGCCTTCTCTGGCAAGGACCGACCGYAGTGGCGCCTACATTGCCAGGC 940
                   |||||||||||||||||||| |||| |||||||||||||||||||||||
SEQ ID NO:43   863 GTGCCTTCTCTGGCAAGGACCCCTACCAAGGTCGACCGCAGTGGCGCCTACATTGCCAGGC 922
```

Fig. 8C

```
SEQ ID NO:42   941 ARGCCGCCAAGAGAGCATCATCGCCAGCGGCCTCGCACGCGCCGCTGCATTGTGCAGATCTCAT 1000
                      |||||||||||||||||||||||||||  ||||||||||||||||||||||||||||||||
SEQ ID NO:43   923 AGGCTGCCAAGAGAGCATCATCGCCAGCGCCTCGCACGCGGCCGTGCATTGTGCAGATCTCAT 982

SEQ ID NO:42  1001 ACGCCATCGGTGTGCCTGAGCCTTTGTCTGTGTTCGTGACTCCTACGGCACCGGCAAGA 1060
                   |||||||||| ||||||||||||||||||||||||| ||||||||||||| ||||||||
SEQ ID NO:43   983 ATGCCATCGGTGTACCTGAGCCTTTGTCTGTGTTCGTCGTGACTCCTACGGCACTGGCAAGA 1042

SEQ ID NO:42  1061 TCCCCGACAGGGAGATCCTCAAGCTCGTGAAGGAGAACTTTGACTTCAGGCCCGGGATGA 1120
                   |||| ||||||||||||||||||||||||||||||||||||||||||||||| ||||||||
SEQ ID NO:43  1043 TCCCTGACAGGGAGATCCTCAAGCTCGTGAAGGAGAACTTTGACTTCAGACCCGGGATGA 1102

SEQ ID NO:42  1121 TCAGCATCAACCTGGACTTGAAGAAAGGTGGAAACAGGTTCATCAAGACCGCTGCTTACG 1180
                   |||| ||||||||||||||||||| || ||||||||||||||||||||| |||||||||||
SEQ ID NO:43  1103 TCACGATCAACCTCGACTTGAAGAAAGGTGGAAACAGGTTCATCAAGACAGCTGCTTACG 1162

SEQ ID NO:42  1181 GTCACTTTGGCCGTGATGATGCCGACTTCACCTGGGAGGTGGTGAAGCCCCCTCAAGTTCG 1240
                   |||||||||||||||||||| |||||||||||||||||||||||||||| ||||||||||
SEQ ID NO:43  1163 GTCACTTTGGCCGCGATGATGCTGACTTCACCTGGGAGGTGGTGAAGCCCCTCAAGTTCG 1222

SEQ ID NO:42  1241 ACAAGGCATCTCGCCTAAGAGACATGGCAT 1268
                   |||||||||| || || ||||| |||
SEQ ID NO:43  1223 ACAAGGCATCTGCTTAAGAAGAAGACAT 1250

SEQ ID NO:42  1271 TCTTGGTCTGCGCCTCTCAAGTTCGTCAAGACGGGATCATGTTGCTCCTGGAAGTGGG 1330
                   |||||||||||||| || |||||||||||||||||||||||| |||||| |||||||||
SEQ ID NO:43  1266 TCTTGGTCTGATGCCTCAAGTTCGGCAAGGCGGGATCCTTTGCTCCTCGAAGTAAG 1325

SEQ ID NO:42  1331 AAGAAGCATTAGACATTG 1348
                   ||||||||||| |||| |
SEQ ID NO:43  1326 AAGAAGCATTCAACATCG 1343
```

PLANT AMINO ACID BIOSYNTHETIC ENZYMES

This application is a divisional of U.S. application Ser. No. 09/424,978, filed Dec. 2, 1999, now granted as U.S. Pat. No. 6,664,445, which is a National Stage Application of PCT/US98/11692, filed Jun. 5, 1998, which claims the benefit of U.S. Provisional Application No. 60/048,771, filed Jun. 6, 1997, and U.S. Provisional Application No. 60/049,443, filed Jun. 12, 1997.

FIELD OF THE INVENTION

This invention is in the field of plant molecular biology. More specifically, this invention pertains to nucleic acid fragments encoding enzymes involved in amino acid biosynthesis in plants and seeds.

BACKGROUND OF THE INVENTION

Many vertebrates, including man, lack the ability to manufacture a number of amino acids and therefore require these amino acids preformed in the diet. These are called essential amino acids. Human food and animal feed, derived from many grains, are deficient in essential amino acids, such as lysine, the sulfur amino acids methionine and cysteine, threonine and tryptophan. For example, in corn (*Zea mays* L.) lysine is the most limiting amino acid for the dietary requirements of many animals. Soybean (*Glycine max* L.) meal is used as an additive to corn-based animal feeds primarily as a lysine supplement. Thus, an increase in the lysine content of either corn or soybean would reduce or eliminate the need to supplement mixed grain feeds with lysine produced via fermentation of microbes. Furthermore, in corn the sulfur amino acids are the third most limiting amino acids, after lysine and tryptophan, for the dietary requirements of many animals. The use of soybean meal, which is rich in lysine and tryptophan, to supplement corn in animal feed is limited by the low sulfur amino acid content of the legume. Thus, an increase in the sulfur amino acid content of either corn or soybean would improve the nutritional quality of the mixtures and reduce the need for further supplementation through addition of more expensive methionine.

Lysine, threonine, methionine, cysteine and isoleucine are amino acids derived from aspartate. Regulation of the biosynthesis of each member of this family is interconnected (see FIG. 1). One approach to increasing the nutritional quality of human foods and animal feed is to increase the production and accumulation of specific free amino acids via genetic engineering of this biosynthetic pathway. Alteration of the activity of enzymes in this pathway could lead to altered levels of lysine, threonine, methionine, cysteine and isoleucine. However, few of the genes encoding enzymes that regulate this pathway in plants, especially corn, soybeans and wheat, are available.

The organization of the pathway leading to biosynthesis of lysine, threonine, methionine, cysteine and isoleucine indicates that over-expression or reduction of expression of genes encoding, inter alia, threonine synthase, dihydrodipicolinate reductase, diaminopimelate epimerase, threonine deaminase and S-adenosylmethionine synthetase in corn, soybean, wheat and other crop plants could be used to alter levels of these amino acids in human food and animal feed. Accordingly, availability of nucleic acid sequences encoding all or a portion of these enzymes would facilitate development of nutritionally improved crop plants.

SUMMARY OF THE INVENTION

The instant invention relates to isolated nucleic acid fragments encoding plant enzymes involved in amino acid biosynthesis. Specifically, this invention concerns isolated nucleic acid fragments encoding the following plant enzymes that catalyze steps in the biosynthesis of lysine, threonine, methionine, cysteine and isoleucine from aspartate: dihydrodipicolinate reductase, diaminopimelate epimerase, threonine synthase, threonine deaminase and S-adenosylmethionine synthetase. In addition, this invention relates to nucleic acid fragments that are complementary to nucleic acid fragments encoding the listed plant biosynthetic enzymes.

In another embodiment, the instant invention relates to chimeric genes encoding the amino acid biosynthetic acid enzymes listed above or to chimeric genes that comprise nucleic acid fragments that are complementary to the nucleic acid fragments encoding the enzymes, operably linked to suitable regulatory sequences, wherein expression of the chimeric genes results in production of levels of the encoded enzymes in transformed host cells that are altered (i.e., increased or decreased) from the levels produced in untransformed host cells.

In a further embodiment, the instant invention concerns a transformed host cell comprising in its genome a chimeric gene encoding a plant amino acid biosynthetic enzyme operably linked to suitable regulatory sequences, the enzyme selected from the group consisting of: dihydrodipicolinate reductase, diaminopimelate epimerase, threonine synthase, threonine deaminase and S-adenosylmethionine synthetase. Expression of the chimeric gene results in production of altered levels of the biosynthetic enzyme in the transformed host cell. The transformed host cells can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of a plant biosynthetic enzyme in a transformed host cell comprising: a) transforming a host cell with a chimeric gene comprising a nucleic acid fragment encoding a plant biosynthetic enzyme selected from the group consisting of dihydrodipicolinate reductase, diaminopimelate epimerase, threonine synthase, threonine deaminase and S-adenosylmethionine synthetase, operably linked to suitable regulatory sequences; and b) growing the transformed host cell under conditions that are suitable for expression of the chimeric gene wherein expression of the chimeric gene results in production of altered levels of the biosynthetic enzyme in the transformed host cell.

An additional embodiment of the instant invention concerns a method for obtaining a nucleic acid fragment encoding all or substantially all of an amino acid sequence encoding a plant dihydrodipicolinate reductase, diaminopimelate epimerase, threonine synthase, threonine deaminase and S-adenosylmethionine synthetase.

A further embodiment of the instant invention is a method for evaluating at least one compound for its ability to inhibit the activity of a plant biosynthetic enzyme selected from the group consisting of dihydrodipicolinate reductase, diaminopimelate epimerase, threonine synthase, threonine deaminase and S-adenosylmethionine synthetase, the method comprising the steps of: (a) transforming a host cell with a chimeric gene comprising a nucleic acid fragment encoding a plant biosynthetic enzyme selected from the group consisting of dihydrodipicolinate reductase, diaminopimelate epimerase, threonine synthase, threonine deaminase and S-denosylmethionine synthetase, operably linked to suitable regulatory sequences; (b) growing the transformed host cell under conditions that are suitable for expression of the chimeric gene wherein expression of the chimeric gene results in production of the biosynthetic enzyme in the transformed host cell; (c) optionally purifying the biosynthetic enzyme expressed by the transformed host cell; (d) treating the biosynthetic enzyme with a compound to be tested; and (e) comparing the activity of the biosynthetic enzyme that has been treated with a test compound to the activity of an untreated biosynthetic enzyme, thereby selecting compounds with potential for inhibitory activity.

BRIEF DESCRIPTION OF THE DRAWINGS AND SEQUENCE DESCRIPTIONS

The invention can be more fully understood from the following detailed description and the accompanying drawings and sequence descriptions which form a part of this application.

FIG. 1 depicts the biosynthetic pathway for the aspartate family of amino acids. The following abbreviations are used: AK=aspartokinase; ASADH=aspartic semialdehyde dehydrogenase; DHDPS=dihydrodipicolinate synthase; DHDPR=dihydrodipicolinate reductase; DAPEP=diaminopimelate epimerase; DAPDC=diaminopimelate decarboxylase; HDH=homoserine dehydrogenase; HK=homoserine kinase; TS=threonine synthase; TD=threonine deaminase; CγS=cystathionine γ-synthase; CβL=cystathionine β-lyase; MS=methionine synthase; CS=cysteine synthase; and SAMS=S-adenosylmethionine synthase.

FIG. 2 shows a multiple alignment of the amino acid sequence fragments reported herein encoding dihydrodipicolinate reductase (SEQ ID NOs:2 and 4) and the *Synechocystis* sp. dihydrodipicolinate reductase sequence set forth in DDBJ Accession No. D90899 (SEQ ID NO:5).

FIGS. 3A and 3B show a multiple alignment of the amino acid sequence fragments reported herein encoding diaminopimelate epimerase (SEQ ID NOs:7, 9, 11, and 13) and the *Synechocystis* sp. diaminopimelate epimerase sequence set forth in DDBJ Accession No. D90917 (SEQ ID NO:14).

FIGS. 4A, 4B and 4C show a multiple alignment of the amino acid sequence fragments reported herein encoding threonine synthase (SEQ ID NOs:16, 18, 20, 22, 24, and 26) and the *Arabidopsis thaliana* threonine synthase sequence set forth in GenBank Accession No. L41666 (SEQ ID NO:27).

FIGS. 5A and 5B show a multiple alignment of the amino acid sequence fragments reported herein encoding threonine deaminase (SEQ ID NOs:29, 31, and 33) to the *Brukholderia capacia* threonine synthase set forth in GenBank Accession No. U40630 (SEQ ID NO:34).

FIGS. 6A, 6B and 6C show the nucleotide sequence alignment of the S-adenosylmethionine synthetase reported herein for corn (SEQ ID NO:35) with the *Oryza sativa* S-adenosylmethionine synthetase nucleotide sequence set forth in EMBL Accession No. Z26867 (SEQ ID NO:37).

FIGS. 7A, 7B and 7C show the nucleotide sequence alignment of the S-adenosylmethionine synthetase reported here for soybean (SEQ ID NO:38) with the *Lycopersicon esculentum* S-adenosyl-methionine synthetase nucleotide sequence set forth in EMBL Accession No. Z24741 (SEQ ID NO:40).

FIGS. 8A, 8B and 8C show the nucleotide sequence alignment of the S-adenosylmethionine synthetase reported here for wheat (SEQ ID NO:41) with the *Hordeum vulgare* S-adenosylmethionine synthetase nucleotide sequence set forth in DDBJ Accession No. D63835 (SEQ ID NO:43).

Figure 1:
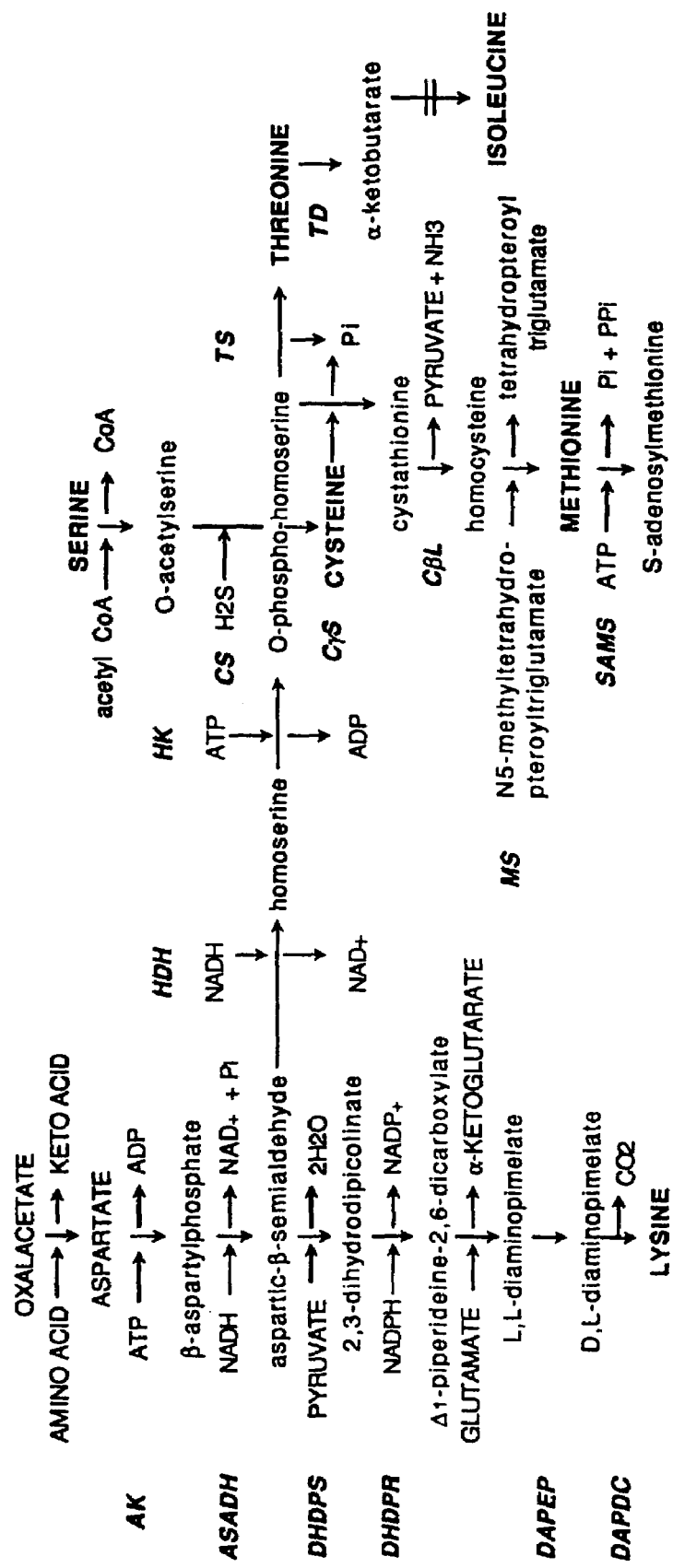

Amino acid sequence alignments were performed using the Clustal method of alignment (Higgins, D. G. and Sharp, P. M. (1989) *CABIOS* 5:151–153), from the Megalign program of the LASARGENE bioinformatics computing suite (DNASTAR Inc., Madison, Wis.). Nucleotide sequence alignments were a result of the BLASTN search performed with each individual S-adenosylmethionine sequence.

The following sequence descriptions and sequence listings attached hereto comply with the rules governing nucleotide and/or amino acid sequence disclosures in patent applications as set forth in 37 C.F.R. §1.821–1.825.

SEQ ID NO:1 is the nucleotide sequence comprising the entire cDNA insert in clone csi1n.pk0042.a3 encoding a corn dihydrodipicolinate reductase.

SEQ ID NO:2 is the deduced amino acid sequence of a portion of a corn dihydrodipicolinate reductase derived from the nucleotide sequence of SEQ ID NO:1.

SEQ ID NO:3 is the nucleotide sequence comprising a portion of the cDNA insert in clone rls2.pk0017.d3 encoding a rice dihydrodipicolinate reductase.

SEQ ID NO:4 is the deduced amino acid sequence of a portion of a rice dihydrodipicolinate reductase derived from the nucleotide sequence of SEQ ID NO:3.

SEQ ID NO:5 is the amino acid sequence of the entire *Synechocystis* sp. dihydrodipicolinate reductase DDBJ Accession No. D90899.

SEQ ID NO:6 is the nucleotide sequence comprising the entire cDNA insert in clone chp2.pk0008.h4 encoding a corn diaminopimelate epimerase.

SEQ ID NO:7 is the deduced amino acid sequence of a portion of a corn diaminopimelate epimerase derived from the nucleotide sequence of SEQ ID NO:6.

SEQ ID NO:8 is the nucleotide sequence comprising a portion of the cDNA insert in clone rls48.pk0036.h10 encoding a rice diaminopimelate epimerase.

SEQ ID NO:9 is the deduced amino acid sequence of a portion of a rice diaminopimelate epimerase derived from the nucleotide sequence of SEQ ID NO:8.

SEQ ID NO:10 is the nucleotide sequence comprising a contig formed of portions of sfl1.pk0031.h3, and sgs1c.pk002.k12, and the entire cDNA insert from clones se2.pk0005.f1, and ses8w.pk0010.h11 encoding a soybean diaminopimelate epimerase.

SEQ ID NO:11 is the deduced amino acid sequence of a soybean diaminopimelate epimerase derived from the nucleotide sequence of SEQ ID NO:10.

SEQ ID NO:12 is the nucleotide sequence comprising a portion of the cDNA insert in clone wlm24.pk0030.g4 encoding a wheat diaminopimelate epimerase.

SEQ ID NO:13 is the deduced amino acid sequence of a portion of a wheat diaminopimelate epimerase derived from the nucleotide sequence of SEQ ID NO:12.

SEQ ID NO:14 is the nucleotide sequence comprising the entire *Synechocystis* sp. diaminopimelate epimerase DDBJ Accession No. D90917.

SEQ ID NO:15 is the nucleotide sequence comprising the entire cDNA insert in clone cc2.pk0031.c9 encoding a corn threonine synthase.

SEQ ID NO:16 is the deduced amino acid sequence of a portion of a corn threonine synthase derived from the nucleotide sequence set forth in SEQ ID NO:15.

SEQ ID NO:17 is the nucleotide sequence comprising part of the cDNA insert in clone cs1.pk0058.g5 encoding a corn threonine synthase.

SEQ ID NO:18 is the deduced amino acid sequence of a portion of a corn threonine synthase derived from the nucleotide sequence of SEQ ID NO:17.

SEQ ID NO:19 is the nucleotide sequence comprising part of the cDNA insert in clone rls72.pk0018.e7 encoding a rice threonine synthase.

SEQ ID NO:20 is deduced amino acid sequence of a portion of a rice threonine synthase derived from the nucleotide sequence set forth in SEQ ID NO:19.

SEQ ID NO:21 is the nucleotide sequence comprising part of the cDNA insert in clone se1.06a03 encoding a soybean threonine synthase.

SEQ ID NO:22 is the deduced amino acid sequence of a portion of a soybean threonine synthase derived from the nucleotide sequence set forth in SEQ ID NO:21.

SEQ ID NO:23 is the nucleotide sequence comprising the entire cDNA insert in clone sr1.pk0003.f6 encoding a soybean threonine synthase.

SEQ ID NO:24 is the deduced amino acid sequence of a portion of a soybean threonine synthase derived from the nucleotide sequence set forth in SEQ ID NO:23.

SEQ ID NO:25 is the nucleotide sequence comprising part of the cDNA insert in clone wr1.pk0085.h2 encoding a wheat threonine synthase.

SEQ ID NO:26 is the deduced amino acid sequence of a portion of a wheat threonine synthase derived from the nucleotide sequence set forth in SEQ ID NO:25.

SEQ ID NO:27 is the entire amino acid sequence of an *Arabidopsis thaliana* threonine synthase found in GenBank Accession No. L41666.

SEQ ID NO:28 is the nucleotide sequence comprising the entire cDNA insert in clone cen1.pk0064.f4 encoding a corn threonine deaminase.

SEQ ID NO:29 is the deduced amino acid sequence of a portion of a corn threonine deaminase derived from the nucleotide sequence set forth in SEQ ID NO:28.

SEQ ID NO:30 is the nucleotide sequence comprising a portion of the cDNA insert in clone sfl1.pk0055.h7 encoding a soybean threonine deaninase.

SEQ ID NO:31 is the deduced amino acid sequence of a portion of a soybean threonine deaminase derived from the nucleotide sequence set forth in SEQ ID NO:30.

SEQ ID NO:32 is the nucleotide sequence comprising the entire cDNA insert in clone sre.pk0044.f3 encoding a soybean threonine deaminase.

SEQ ID NO:33 is the deduced amino acid sequence of a portion of a soybean threonine deaminase derived from the nucleotide sequence set forth in SEQ ID NO:32.

SEQ ID NO:34 is the entire amino acid sequence of a *Burkholderia capacia* threonine deaminase found in GenBank Accession No. U49630.

SEQ ID NO:35 is the nucleotide sequence comprising the entire cDNA insert in clone cc3.mn0002.d2 encoding the entire corn S-adenosylmethionine synthetase.

SEQ ID NO:36 is the deduced amino acid sequence of a corn S-adenosylmethionine synthetase derived from the nucleotide sequence set forth in SEQ ID NO:35. SEQ ID NO:37 is the entire nucleotide sequence of a *Oryza sativa* S-adenosyl-methionine synthetase found in EMBL Accession No. Z26867.

SEQ ID NO:38 is the nucleotide sequence of the entire cDNA insert in clone s2.12b06 encoding the entire soybean S-adenosyl-methionine synthetase.

SEQ ID NO:39 is the deduced amino acid sequence of the entire soybean S-adenosyl-methionine synthetase derived from the nucleotide sequence set forth in SEQ ID NO:38.

SEQ ID NO:40 is the entire nucleotide sequence of a *Lycopersicon esculentum* S-adenosyl-methionine synthetase found in EMBL Accession No. Z24741.

SEQ ID NO:41 is the nucleotide sequence comprising a contig formed of portions of the cDNA inserts in clones wre1.pk0002.c12, wle1n.pk0070.b8, wkm1c.pk0003.g4, wlk1.pk0028.d3, wre1n.pk170.d8, wr1.pk0086.d5, wr1.pk0103.h8, and wre1n.pk0082.b2 encoding a portion of a wheat S-adenosyl-methionine synthetase.

SEQ ID NO:42 is the deduced amino acid sequence of a wheat S-adenosyl-methionine synthetase derived from the nucleotide sequence set forth in SEQ ID NO:41.

SEQ ID NO:43 is the entire nucleotide sequence of a *Hordeum vulgare* S-adenosyl-methionine synthetase found in DDBJ Accession No. D63835.

The Sequence Descriptions contain the one letter code for nucleotide sequence characters and the three letter codes for amino acids as defined in conformity with the IUPAC-IYUB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. As used herein, "contig" refers to an assemblage of overlapping nucleic acid sequences to form one contiguous nucleotide sequence. For example, several DNA sequences can be compared and aligned to identify common or overlapping regions. The individual sequences can then be assembled into a single contiguous nucleotide sequence.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotides that do not substantially affect the functional properties of the resulting transcript vis-a-vis the ability to mediate alteration of gene expression by antisense or co-suppression technology or alteration of the functional properties of the resulting protein molecule. It is therefore understood that the invention encompasses more than the specific exemplary sequences.

For example, it is well known in the art that antisense suppression and co-suppression of gene expression may be accomplished using nucleic acid fragments representing less that the entire coding region of a gene, and by nucleic acid fragments that do not share 100% identity with the gene to be suppressed. Moreover, alterations in a gene which result in the production of a chemically equivalent amino acid at a given site, but do not effect the functional properties of the encoded protein, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products. Moreover, the skilled artisan recognizes that substantially similar sequences encompassed by this invention are also defined by their ability to hybridize, under stringent conditions (0.1×SSC, 0.1% SDS, 65° C.), with the sequences exemplified herein. Preferred substantially similar nucleic acid fragments of the instant invention are those nucleic acid fragments whose DNA sequences are 80% identical to the DNA sequence of the nucleic acid fragments reported herein. More preferred nucleic acid fragments are 90% identical to the identical to the DNA sequence of the nucleic acid fragments reported herein. Most preferred are nucleic acid fragments that are 95% identical to the DNA sequence of the nucleic acid fragments reported herein. The Clustal multiple alignment alogarithm (Higgins, D. G. and Sharp, P. M. (1989) *CABIOS* 5:151–153) was used here with a GAP PENALTY of 10 and a GAP LENGTH PENALTY of 10.

A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) J. Mol. Biol. 215:403–410). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in POR in order to obtain a particular nucleic acid fragment comprising the primers. Accordingly, a "substantial portion" of a nucleotide sequence comprises enough of the sequence to afford specific identification and/or isolation of a nucleic acid fragment comprising the sequence. The instant specification teaches partial or complete amino acid and nucleotide sequences encoding one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the amino acid biosynthetic enzymes as set forth in SEQ ID NOs:2, 4, 7, 9, 11, 13, 16, 18, 20, 22, 24, 26, 29, 31, and 33. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (1989) *Biochemistry of Plants* 15:1–82. It is further recognized that since in most cases the exact boundaries of regulatory sequences have not been completely defined, DNA fragments of different lengths may have identical promoter activity.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020).

"Altered levels" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels, J. J., (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.*100: 1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature (London)* 327:70–73; U.S. Pat. No. 4,945,050).

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Maniatis").

Nucleic acid fragments encoding at least a portion of several plant amino acid biosynthetic enzymes have been isolated and identified by comparison of random plant cDNA sequences to public databases containing nucleotide and protein sequences using the BLAST algorithms well known to those skilled in the art. Table 1 lists the amino acid biosynthetic enzymes that are described herein, and the designation of the cDNA clones that comprise the nucleic acid fragments encoding these enzymes.

TABLE 1

Amino Acid Biosynthetic Enzymes

| Enzyme | Clone | Plant |
|---|---|---|
| dihydrodipicolinate reductase | cs1.pk0083.b10 | corn |
|  | rls2.pk0017.d3 | rice |
| diaminopimelate epimerase | chp2.pk0008.h4 | corn |
|  | rls48.pk0036.h10 | rice |
|  | se2.pk0005.f1 | soybean |
|  | ses8w.pk0010.f11 | soybean |
|  | sfl1.pk0031.h3 | soybean |
|  | sgs1c.pk002.k12 | soybean |
|  | wlm24.pk0030.g4 | wheat |
| threonine synthase | cc2.pk0031.c9 | corn |
|  | cs1.pk0058.g5 | corn |
|  | rls72.pk0018.e7 | rice |
|  | se1.06a03 | soybean |
|  | sr1.pk0003.f6 | soybean |
|  | wr1.pk0085.h2 | wheat |
| threonine deaminase | cen1.pk0064.f4 | corn |
|  | sfl1.pk0055.h7 | soybean |
|  | sre.pk0044.f3 | soybean |
| s-adenosylmethionine synthase | cc3.mn0002.d2 | corn |
|  | se2.12b06 | soybean |
|  | wre1.pk0002.c12 | wheat |
|  | wle1n.pk0070.b8 | wheat |
|  | wkm1c.pk0003.g4 | wheat |
|  | wlk1.pk0028.d3 | wheat |
|  | wre1n.pk170.d8 | wheat |
|  | wr1.pk0086.d5 | wheat |
|  | wr1.pk0103.h8 | wheat |
|  | wre1n.pk0082.b2 | wheat |

The nucleic acid fragments of the instant invention may be used to isolate cDNAs and genes encoding homologous enzymes from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other amino acid biosynthetic enzymes, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al., (1988) *PNAS USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., (1989) *PNAS USA* 86:5673; Loh et al., (1989) *Science* 243:217). Products generated by the 3' and 5' RACE procedures can be combined to generate full-length cDNAs (Frohman, M. A. and Martin, G. R., (1989) *Techniques* 1:165).

Availability of the instant nucleotide and deduced amino acid sequences facilitates immunological screening cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner, R. A. (1984) *Adv. Immunol.* 36:1; Maniatis).

The nucleic acid fragments of the instant invention may be used to create transgenic plants in which the disclosed biosynthetic enzymes are present at higher or lower levels than normal or in cell types or developmental stages in which they are not normally found. This would have the effect of altering the level of free amino acids in those cells.

Overexpression of the biosynthetic enzymes of the instant invention may be accomplished by first constructing chimeric genes in which the coding region are operably linked to promoters capable of directing expression of a gene in the desired tissues at the desired stage of development. For reasons of convenience, the chimeric genes may comprise promoter sequences and translation leader sequences derived from the same genes. 3' Non-coding sequences encoding transcription termination signals may also be provided. The instant chimeric genes may also comprise one or more introns in order to facilitate gene expression.

Plasmid vectors comprising the instant chimeric genes can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., (1985) *EMBO J.* 4:2411–2418; De Almeida et al., (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant biosynthetic enzymes to different cellular compartments, or to facilitate their secretion from the cell. It is thus envisioned that the chimeric genes described above may be further supplemented by altering the coding sequences to encode enzymes with appropriate intracellular targeting sequences such as transit sequences (Keegstra, K. (1989) *Cell* 56:247–253), signal sequences or sequences encoding endoplasmic reticulum localization (Chrispeels, J. J., (1991) *Ann. Rev. Plant Phys. Plant Mol. Biol.* 42:21–53), or nuclear localization signals (Raikhel, N. (1992) *Plant Phys.*100: 1627–1632) added and/or with targeting sequences that are already present removed. While the references cited give examples of each of these, the list is not exhaustive and more targeting signals of utility may be discovered in the future.

It may also be desirable to reduce or eliminate expression of the genes encoding the instant biosynthetic enzymes in plants for some applications. In order to accomplish this, chimeric genes designed for co-suppression of the instant biosynthetic enzymes can be constructed by linking the genes or gene fragments encoding the enzymes to plant promoter sequences. Alternatively, chimeric genes designed to express antisense RNA for all or part of the instant nucleic acid fragments can be constructed by linking the genes or gene fragment in reverse orientation to plant promoter sequences. Either the co-suppression or antisense chimeric genes could be introduced into plants via transformation wherein expression of the corresponding endogenous genes are reduced or eliminated.

The instant amino acid biosynthetic enzymes (or portions of the enzymes) may be produced in heterologous host cells, particularly in the cells of microbial hosts, and can be used to prepare antibodies to the enzymes by methods well known to those skilled in the art. The antibodies are useful for detecting the enzymes in situ in cells or in vitro in cell extracts. Preferred heterologous host cells for production of the instant amino acid biosynthetic enzymes are microbial hosts. Microbial expression systems and expression vectors containing regulatory sequences that direct high level expression of foreign proteins are well known to those skilled in the art. Any of these could be used to construct chimeric genes for production of the instant amino acid biosynthetic enzymes. These chimeric genes could then be introduced into appropriate microorganisms via transformation to provide high level expression of the enzymes. An example of a vector for high level expression of the instant amino acid biosynthetic enzymes in a bacterial host is provided (Example 11).

Additionally, the instant plant amino acid biosynthetic enzymes can be used as a targets to facilitate design and/or identification of inhibitors of the enzymes that may be useful as herbicides. This is desirable because the enzymes described herein catalyze various steps in a pathway leading to production of several essential amino acids. Accordingly, inhibition of the activity of one or more of the enzymes described herein could lead to inhibition of amino acid biosynthesis sufficient to inhibit plant growth. Thus, the instant plant amino acid biosynthetic enzymes could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et at., (1987) *Genomics* 1:174–181) in order to construct a genetic map. In addition, the nucleic acid fragments of the instant invention may be used to probe Southern blots containing resriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein, D. et al., (1980) *Am. J. Hum. Genet.* 32:314–331).

The production and use of plant gene-derived probes for use in genetic mapping is described in R. Bernatzky, R. and Tanksley, S. D. (1986) *Plant Mol. Biol. Reporter* 4(1): 37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel, J. D., et al., In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask, B. J. (1991) *Trends Genet.* 7:149–154). Although current methods of FISH mapping favor use of large clones (several to several hundred KB; see Laan, M. et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian, H. H. (1989) *J. Lab. Clin. Med.* 114(2):95–96), polymorphism of PCR-amplified fragments (CAPS; Sheffield, V. C. et al. (1993) *Genomics* 16:325–332), allele-specific ligation (Landegren, U. et al. (1988) *Science* 241:1077–1080), nucleotide extension reactions (Sokolov, B. P. (1990) *Nucleic Acid Res.* 18:3671), Radiation Hybrid Mapping (Walter, M. A. et al. (1997) *Nature Genetics* 7:22–28) and Happy Mapping (Dear, P. H. and Cook, P. R. (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer, (1989) *Proc. Natl. Acad. Sci USA* 86:9402; Koes et al., (1995) *Proc. Natl. Acad. Sci USA* 92:8149; Bensen et al., (1995) *Plant Cell* 7:75). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding dihydrodipicolinate reductase, diaminopimelate epimerase, threonine synthase, threonine deaminase or S-adenosylmethionine synthetase. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding a dihydrodipicolinate reductase, diaminopimelate epimerase, threonine synthase, threonine deaminase or S-adenosylmethionine synthetase can be identified and obtained. This mutant plant can then be used to determine or confirm the natural function of the dihydro-dipicolinate reductase, diaminopimelate epimerase, threonine synthase, threonine deaminase and S-adenosylmethionine synthetase gene product.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various corn, rice, soybean and wheat tissues were prepared. The characteristics of the libraries are described below.

TABLE 2 cDNA Libraries from Corn and Soybean Tissues

| Library | Tissue | Clone |
|---|---|---|
| cc2 | Corn Callus, Partially Differentiated, 2 Weeks After Subculture | cc2.pk0031.c9 |
| cc3 | Corn Callus, Mature Somatic Embryo | cc3.mn0002.d2 |
| cen1 | Corn Endosperm 12 Days After Pollination | cen1.pk0064.f4 |
| chp2 | Corn Leaf, 11 Day Old Plant | chp2.pk0008.h4 |
| cs1 | Corn Leaf, Sheath 5 Week Old Plant | cs1.pk0058.g5 |
| csi1n | Corn Silk* | csi1n.pk0042.a3 |
| rls2 | Rice Leaf 15 Days After Germination, 2 Hours After Infection of Strain *Magaporthe grisea* 4360-R-67 (AVR2-YAMO); Susceptible | rls2.pk0017.d3 |
| rls48 | Rice Leaf 15 Days After Germination, 48 Hours After Infection of Strain *Magaporthe grisea* 4360-R-67 (AVR2-YAMO); Susceptible | rls48.pk0036.h10 |
| rls72 | Rice Leaf 15 Days After Germination, 72 Hours After Infection of Strain *Magaporthe grisea* 4360-R-67 (AVR2-YAMO); Susceptible | rls72.pk0018.e7 |
| s2 | Soybean Seed, 19 Days After Flowering | s2.12b06 |
| se1 | Soybean Embryo 7 Days After Flowering | se1.06a03 |
| se2 | Soybean Embryo 10 Days After Flowering | se2.pk0005.f1 |
| ses8w | Mature Soybean Embryo 8 Weeks After Subculture | ses8w.pk0010.h11 |
| sfl1 | Soybean Immature Flower | sfl1.pk0055.h7 sfl1.pk0031.h3 |
| sgs1c | Soybean Seeds 4 Hours After Germination | sgs1c.pk002.k12 |
| sr1 | Soybean Root From 10 Day Old Seedlings | sr1.pk0003.f6 |
| sre | Soybean Root Elongation 4–5 Days After Germination | sre.pk0044.f3 |
| wkm1c | Wheat Kernel Malted 55 Hours at 22 Degrees Celsius | wkm1c.pk0003.g4 |
| wle1n | Wheat Leaf From 7 Day Old Etiolated Seedling* | wle1n.pk0070.b8 |
| wlk1 | Wheat Seedlings 1 Hour After Treatment with Fungicide** | wlk1.pk0028.d3 |
| wlm24 | Wheat Seedlings 24 Hours After Inoculation With *Erysiphe graminis* f. sp *tritici* | wlm24.pk0030.g4 |
| wr1 | Wheat Root From 7 Day Old Seedling | wr1.pk0085.h2 wr1.pk0086.d5 wr1.pk0103.h8 |
| wre1 | Wheat Root From 7 Day Old Etiolated Seedling | wre1.pk0002.c12 |
| wre1n | Wheat Root From 7 Day Old Etiolated Seedling* | wre1n.pk0082.b2 wre1n.pk170.d8 |

*These libraries were normalized essentially as described in U.S. Pat. No. 5,482,845
**Application of 6-iodo-2-propoxy-3-propyl-4(3H)-quinazolinone; synthesis and methods of using this compound are described in USSN 08/545,827, incorporated herein by reference.

cDNA libraries were prepared in Uni-ZAP™ XR vectors according to the manufacturer's protocol (Stratagene Cloning Systems, La Jolla, Calif.). Conversion of the Uni-ZAP™ XR libraries into plasmid libraries was accomplished according to the protocol provided by Stratagene. Upon conversion, cDNA inserts were contained in the plasmid vector pBluescript cDNA inserts from randomly picked bacterial colonies containing recombinant pBluescript plasmids were amplified via polymerase chain reaction using primers specific for vector sequences flanking the inserted cDNA sequences, or plasmid DNA was prepared from cultured bacterial cells. Amplified insert DNAs or plasmid DNAs were sequenced in dye-primer sequencing reactions to generate partial cDNA sequences (expressed sequence tags or "ESTs"; see Adams, M. D. et al., (1991) *Science* 252:1651). The resulting ESTs were analyzed using a Perkin Elmer Model 377 fluorescent sequencer.

Example 2

Identification and Characterization of cDNA Clones

ESTs encoding plant amino acid biosynthetic enzymes were identified by conducting BLAST (Basic Local Alignment Search Tool; Altschul, S. F., et al., (1993) *J. Mol. Biol.* 215:403–410); searches for similarity to sequences contained in the BLAST "nr" database (comprising all non-redundant GenBank ODS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Polypeptides Homologous to Dihydrodipicolinate Reductase The BLASTX search using the nucleotide sequences from clones csi1n.pk0042.a3 and rls2.pk0017.d3 revealed similarity of the protein encoded by the cDNA to *Synechocystis* sp. dihydrodipicolinate reductase enzyme (DDBJ Accession No. D90899). BLAST pLog values were 12.60 and 11.68 for csi1n.pk0042.a3 and rls2.pk0017.d3, respectively.

The sequence of the entire cDNA insert in clone csi1n.pk0042.a3 was determined and is shown in SEQ ID NO:1; the deduced amino acid sequence of this cDNA is shown in SEQ ID NO:2. The amino acid sequence set forth in SEQ ID NO:2 was evaluated by BLASTP, yielding a pLog value of 36.72 versus the *Synechocystis* sp. dihydrodipicolinate reductase sequence. The sequence of a portion of the cDNA insert from clone rls2.pk0017.d3 is shown in SEQ ID NO:3; the deduced amino acid sequence of this cDNA is shown in SEQ ID NO:4. FIG. 2 presents an alignment of the amino acid sequences set forth in SEQ ID NO:2 and the *Synechocystis* sp. dihydrodipicolinate reductase sequence (SEQ ID NO:5). SEQ ID NO:2 is 40% identical to the *Synechocystis* sp. dihydrodipicolinate reductase sequence (SEQ ID NO:5). Sequence alignments were performed by the Clustal method of alignment (Higgins, D. G. and Sharp, P. M. (1989) *CABIOS* 5:151–153), using the Megalign program of the LASARGENE bioinformatics computing suite (DNASTAR Inc., Madison, Wis.). Sequence percent identity calculations were performed by the Jotun Hein method (Hein. J. J. (1990) *Meth. Enz.* 183:626–645) using the Megalign program of the LASARGENE bioinformatics computing suite (DNASTAR Inc., Madison, Wis.).

Sequence alignments and BLAST scores and probabilities indicate that the instant nucleic acid fragments encode a nearly entire corn dihydropicolinate reductase, and a portion of a rice dihydropicolinate reductase. These sequences represent the first plant sequences encoding dihydropicolinate reductase.

Example 4

Characterization of cDNA Clones Encoding Diaminopimelate Epimerase

The BLASTX search using the nucleotide sequences from clones chp2.pk0008.h4, rls48.pk0036.h10, wlm24.pk0030.g4, and the contig sequences assembled from clones se2.pk0005.fl, ses8w.pk0010.h11, sfl1.pk0031.h3, and sgs1c.pk002.k12 revealed similarity of the proteins encoded by the cDNAs to diaminopimelate epimerase from *Synechocystis* sp. (DDBJ Accession No. D90917). The BLAST results for each of these ESTs are shown in Table 3:

TABLE 3

BLAST Results for Clones Encoding Polypeptides Homologous to Diaminopimelate Epimerase

| Clone | BLAST pLog Score DDBJ Accession No. D90917 |
| --- | --- |
| chp2.pk0008.h4 | 59.16 |
| rls48.pk0036.h10 | 40.82 |
| The contig of: | 98.30 |
| se2.pk0005.fl | |
| ses8w.pk0010.h11 | |
| sfl1.pk0031.h3 | |
| sgs1c.pk002.k12 | |
| wlm24.pk0030.g4 | 23.46 |

The sequence of the entire cDNA insert in clone chp2.pk0008.h4 was determined and is shown in SEQ ID NO:6; the deduced amino acid sequence of this cDNA is shown in SEQ ID NO:7. The amino acid sequence set forth in SEQ ID NO:7 was evaluated by BLASTP, yielding a pLog value of 75.66 versus the *Synechocystis* sp. sequence. The sequence of a portion of the cDNA insert from clone rls48.pk0036.h10 is shown in SEQ ID NO:8; the deduced amino acid sequence of this cDNA is shown in SEQ ID NO:9. The nucleotide sequence of the contig assembled from clones se2.pk0005.fl, ses8w.pk0010.h11, sfl1.pk0031.h3, and sgs1c.pk002.k12 was determined and is shown in SEQ ID NO:10; the deduced amino acid sequence of this cDNA is shown in SEQ ID NO:11. The amino acid sequence set forth in SEQ ID NO:11 was evaluated by BLASTP, yielding a pLog value of 98.57 versus the *Synechocystis* sp. sequence. The sequence of a portion of the cDNA insert from clone wlm24.pk0030.g4 is shown in SEQ ID NO:12; the deduced amino acid sequence of this cDNA is shown in SEQ ID NO:13. FIGS. 3A and 3B present an alignment of the amino acid sequences set forth in SEQ ID NOs:7, 9, 11, and 13 and the *Synechocystis* sp. sequence (SEQ ID NO:14). The data in Table 4 represents a calculation of the percent identity of the amino acid sequences set forth in SEQ ID NOs: 7, 9, 11, and 13 and the *Synechocystis* sp. sequence.

TABLE 4

Percent Identity of Amino Acid Sequences Deduced From the Nucleotide Sequences of cDNA Clones Encoding Polypeptides Homologous to Diaminopimelate Epimerase

| Clone | SEQ ID NO. | Percent Identity to DDBJ Accession No. D90917 (SEQ ID NO: 16) |
|---|---|---|
| chp2.pk0008.h4 | 7 | 59 |
| rls48.pk0036.h10 | 9 | 74 |
| Contig of: se2.pk0005.fl ses8w.pk0010.h11 sfl1.pk0031.h3 sgs1c.pk002.k12 | 11 | 72 |
| wlm24.pk0030.g4 | 13 | 65 |

Sequence alignments were performed by the Clustal method of alignment (Higgins, D. G. and Sharp, P. M. (1989) CABIOS 5:151–153), using the Megalign program of the LASARGENE bioinformatics computing suite (DNASTAR Inc., Madison, Wis.). Sequence percent identity calculations were performed by the Jotun Hein method (Hein. J. J. (1990) Meth. Enz. 183:626–645) using the Megalign program of the LASARGENE bioinformatics computing suite (DNASTAR Inc., Madison, Wis.).

Sequence alignments and BLAST scores and probabilities indicate that the instant nucleic acid fragments encode a nearly entire corn diaminopimelate epimerase (chp2.pk0008.h4), a portion of a rice diaminopimelate epimerase (rls48.pk0036.h10), and an entire soybean diaminopimelate epimerase (se2.pk0005.fl, ses8w.pk0010.h11, sfl1.pk0031.h3, and sgs1c.pk002.k12), and a portion of a wheat diaminopimelate epimerase (wlm24.pk0030.g4). These sequences represent the first plant sequences encoding diaminopimelate epimerase enzyme.

Example 5

Characterization of cDNA Clones Encoding Threonine Synthase

The BLASTX search using the EST sequences from clones cc2.pk0031.c9, cs1.pk0058.g5, rls72.pk0018.e7, se1.06a03, sr1.pk0003.f6, and wr1.pk0085.h2 revealed similarity of the proteins encoded by the cDNAs to threonine synthase from *Arabidopsis thaliana* (GenBank Accession No. L41666). The BLAST results for each of these ESTs are shown in Table 5:

TABLE 5

BLAST Results for Clones Encoding Polypeptides Homologous to Threonine Synthase

| Clone | BLAST pLog Score L41666 |
|---|---|
| cc2.pk0031.c9 | 56.19 |
| cs1.pk0058.g5 | 8.00 |
| rls72.pk0018.e7 | 29.47 |
| se1.06a03 | 34.15 |
| sr1.pk0003.f6 | 21.13 |
| wr1.pk0085.h2 | 29.47 |

The sequence of the entire cDNA insert in clone cc2.pk0031.c9 was determined and is shown in SEQ ID NO:15; the deduced amino acid sequence of this cDNA is shown in SEQ ID NO:16. The amino acid sequence set forth in SEQ ID NO:16 was evaluated by BLASTP, yielding a pLog value of 166.11 versus the *Arabidopsis thaliana* sequence. BLASTN against dbest indicated identity of nucleotides 520 through 684 from cc2.pk0031.c9 with nucleotides 1 through 162 of a corn EST (GenBank Accession No. T18847). The sequence of a portion of the cDNA insert from clone cs1.pk0058.g5 is shown in SEQ ID NO:17; the deduced amino acid sequence of this cDNA is shown in SEQ ID NO:18. The sequence of a portion of the cDNA insert from clone rls72.pk0018.e7 is shown in SEQ ID NO:19; the deduced amino acid sequence of this cDNA is shown in SEQ ID NO:20. The sequence of a portion of the cDNA insert from clone se.106a03 is shown in SEQ ID NO:21; the deduced amino acid sequence of this cDNA is shown in SEQ ID NO:22. The sequence of the entire cDNA insert in clone sr1.pk0003.f6 was determined and is shown in SEQ ID NO:23; the deduced amino acid sequence of this cDNA is shown in SEQ ID NO:24. The amino acid sequence set forth in SEQ ID NO:24 was evaluated by BLASTP, yielding a pLog value of 275.06 versus the *Arabidopsis thaliana* sequence. The sequence of a portion of the cDNA insert from clone wr1.pk0085.h2 is shown in SEQ ID NO:25; the deduced amino acid sequence of this cDNA is shown in SEQ ID NO:26. FIGS. 4A, 4B and 4C present an alignment of the amino acid sequences set forth in SEQ ID NOs:16, 18, 20, 22, 24, and 26 and the *Arabidopsis thaliana* sequence. The data in Table 6 represents a calculation of the percent identity of the amino acid sequences set forth in SEQ ID NOs:16, 18, 20, 22, 24, and 26 and the *Arabidopsis thaliana* sequence (SEQ ID NO:27).

TABLE 6

Percent Identity of Amino Acid Sequences Deduced From the Nucleotide Sequences of cDNA Clones Encoding Polypeptides Homologous to Threonine Synthase

| Clone | SEQ ID NO. | Percent Identity to L41666 (SEQ ID NO: 29) |
|---|---|---|
| cc2.pk0031.c9 | 16 | 81.0 |
| cs1.pk0058.g5 | 18 | 81.0 |
| rls72.pk0018.e7 | 20 | 55.3 |
| se1.06a03 | 22 | 80.0 |
| sr1.pk0003.f6 | 24 | 84.4 |
| wr1.pk0085.h2 | 26 | 50.4 |

Sequence alignments were performed by the Clustal method of alignment (Higgins, D. G. and Sharp, P. M. (1989) *CABIOS* 5:151–153), using the Megalign program of the LASARGENE bioinformatics computing suite (DNASTAR Inc., Madison, Wis.). Sequence percent identity calculations were performed by the Jotun Hein method (Hein. J. J. (1990) *Meth. Enz.* 183:626–645) using the Megalign program of the LASARGENE bioinformatics computing suite (DNASTAR Inc., Madison, Wis.).

Sequence alignments and BLAST scores and probabilities indicate that the instant nucleic acid fragments encode portions of a corn threonine synthase (cc2.pk0031.c9 and cs1.pk0058.g5), a portion of a rice threonine synthase (rls72.pk0018.e7), portions of a soybean threonine synthase (se1.06a03 and sr1.pk0003.f6), and a portion of a wheat threonine synthase (wr1.pk0085.h2). These sequences represent the first corn, rice, soybean, and wheat sequences encoding threonine synthase.

Example 6

Characterization of cDNA Clones Encoding Threonine Deaminase

The BLASTX search using the EST sequence from clone cen1.pk0064.f4 revealed similarity of the protein encoded by the cDNA to threonine deaminase from *Brukholderia capacia* (GenBank Accession No. U40630; pLog=31.38). The BLASTX search using the EST sequences from clones sfl1.pk0055.h7 and sre.pk0044.f3 revealed similarity of the proteins encoded by the cDNAs to threonine deaminase from *Solanum tuberosum* and *Brukholderia capacia* (EMBL Accession No. X67846 and GenBank Accession No. U40630, respectively). BLAST pLog values were 36.55 and 31.79 for sfl1.pk0055.h7, and 19.47 and 14.51 for sre.pk0044.f3.

The sequence of the entire cDNA insert in clone cen1.pk0064.f4 was determined and is shown in SEQ ID NO:28; the deduced amino acid sequence of this cDNA is shown in SEQ ID NO:29. The amino acid sequence set forth in SEQ ID NO:29 was evaluated by BLASTP, yielding a pLog value of 134.85 versus the *Brukholderia capacia* sequence. The sequence of a portion of the cDNA insert from clone sfl1.pk0055.h7 is shown in SEQ ID NO:30; the deduced amino acid sequence of this cDNA is shown in SEQ ID NO:31. The sequence of the entire cDNA insert in clone sre.pk0044.f3 was determined and is shown in SEQ ID NO:32; the deduced amino acid sequence of this cDNA is shown in SEQ ID NO:33. The amino acid sequence set forth in SEQ ID NO:33 was evaluated by BLASTP, yielding pLog values of 19.24 versus the *Solanum tuberosum* sequence and 15.19 versus the *Brukholderia capacia* threonine deaminase sequence. FIGS. 5A and 5B present an alignment of the amino acid sequences set forth in SEQ ID NOs:29, 31, and 33 and the *Brukholderia capacia* (SEQ ID NO:34) sequence. The data in Table 7 represents a calculation of the percent identity of the amino acid sequences set forth in SEQ ID NOs:29, 31, and 33 and the *Brukholderia capacia* sequence.

TABLE 7

Percent Identity of Amino Acid Sequences Deduced From the Nucleotide Sequences of cDNA Clones Encoding Polypeptides Homologous to Threonine Deaminase

| Clone | SEQ ID NO. | Percent Identity to U40630 (SEQ ID NO: 36) |
|---|---|---|
| cen1.pk0064.f4 | 29 | 61.0 |
| sfl1.pk0055.h7 | 31 | 47.9 |
| sre.pk0044.f3 | 33 | 46.0 |

Sequence aligments were performed by the Clustal method of alignment (Higgins, D. G. and Sharp, P. M. (1989) *CABIOS* 5:151–153), using the Megalign program of the LASARGENE bioinformatics computing suite (DNASTAR Inc., Madison, Wis.). Sequence percent identity calculations were performed by the Jotun Hein method (Hein. J. J. (1990) *Meth. Enz.* 183:626–645) using the Megalign program of the LASARGENE bioinformatics computing suite (DNASTAR Inc., Madison, Wis.)

Sequence alignments and BLAST scores and probabilities indicate that the instant nucleic acid fragments encode a nearly entire corn threonine deaminase (cen1.pk0064.f4) and portions of a soybean threonine deaminase (sfl1.pk0055.h7 and sre.pk0044.f3). These sequences represent the first corn and soybean sequences encoding threonine deaminase.

Example 7

Characterization of cDNA Clones Encoding S-adenosylmethionine Synthetase

The BLASTX search using the nucleotide sequence from clone cc3.mn0002.d2 revealed similarity of the protein encoded by the cDNA to S-adenosylmethionine synthetase from *Oryza sativa* (EMBL Accession No. Z26867; pLog=99.03). The sequence of the entire cDNA insert in clone cc3.mn0002.d2 was determined and is shown in SEQ ID NO:35; the deduced amino acid sequence of this cDNA is shown in SEQ ID NO:36. The nucleotide sequence set forth in SEQ ID NO:35 was evaluated by BLASTN, yielding a pLog value larger than 200 versus the *Oryza sativa* sequence. FIGS. 6A, 6B and 6C present an alignment of the nucleotide sequences set forth in SEQ ID NO:35 and the *Oryza sativa* sequence (SEQ ID NO:37). The nucleotide sequence in SEQ ID NO:35 is 88% identical over 1216 nucleotides to the nucleotide sequence of the *Oryza sativa* S-adenosylmethionine synthetase.

The BLASTX search using the nucleotide sequence from clone s2.12b06 revealed similarity of the protein encoded by the cDNA to S-adenosylmethionine synthetase from *Lycopersicon esculentum* (EMBL Accession No. Z24741; pLog=62.62). The sequence of the entire cDNA insert in clone s2.12b06 was determined and is shown in SEQ ID NO:38; the deduced amino acid sequence of this cDNA is shown in SEQ ID NO:39. The nucleotide sequence set forth in SEQ ID NO:38 was evaluated by BLASTN, yielding a pLog value larger than 200 versus the *Lycopersicon esculentum* sequence. FIGS. 7A, 7B and 7C present an alignment of the nucleotide sequences set forth in SEQ ID NO:38 and the *Lycopersicon esculentum* sequence (SEQ ID NO:40). The nucleotide sequence set forth in SEQ ID NO:38 is 82% identical over 1210 nucleotides to the *Lycopersicon esculentum* sequence.

The BLASTX search using the nucleotide sequence from the contig assembled from clones wre1.pk0002.c12, wle1n.pk0070.b8, wkm1c.pk0003.g4, wlk1.pk0028.d3, wre1n.pk170.d8, wr1.pk0086.d5, wr1.pk0103.h8, and wre1n.pk0082.b2 revealed similarity of the protein encoded by the contig to S-adenosylmethionine synthetase from *Hordeum vulgare* (DDBJ Accession No. D63835) with a pLog value larger than 200. The nucleotide sequence of the contig assembled from clones wre1.pk0002.c12, wle1n.pk0070.b8, wkm1c.pk0003.g4, wlk1.pk0028.d3, wre1n.pk170.d8, wr1.pk0086.d5, wr1.pk0103.h8, and wre1n.pk0082.b2 is shown in SEQ ID NO:41; the deduced amino acid sequence of this cDNA is shown in SEQ ID NO:42. FIGS. 8A, 8B and 8C present an alignment of the nucleotide sequence set forth in SEQ ID NO:41 and the *Hordeum vulgare* sequence (SEQ ID NO:43). The SEQ ID NO:41 is 92% identical to the *Hordeum vulgare* sequence.

Sequence alignments and BLAST scores and probabilities indicate that the instant nucleic acid fragments encode entire or nearly entire corn, soybean, or wheat S-adenosyl-methionine synthetase. These sequences represent the first corn, soybean, or wheat sequences encoding S-adenosylmethionine synthetase.

Example 8

Expression of Chimeric Genes in Monocot Cells

A chimeric gene comprising a cDNA encoding an amino acid biosynthetic enzyme in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers and under appropriate experimental conditions. Cloning sites (NcoI or SmaI) can be incorporated into the oligonucleotides to provide proper orientation of the DNA fragment when inserted into the digested vector pML 103 as described below. The amplified DNA can then be digested with restriction enzymes NcoI and SmaI and fractionated on a 0.7% low melting point agarose gel in 40 mM Tris-acetate, pH 8.5, 1 mM EDTA. The appropriate band can be excised from the gel, melted at 68° C. and combined with a 4.9 kb NcoI-SmaI fragment of the plasmid pML103. Plasmid pML103 has been deposited under the terms of the Budapest Treaty at ATCC (American Type Culture Collection, 10801 University Boulevard, Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (*Epicurian Coli* XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding a plant amino acid biosynthetic enzyme, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al., (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al., (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al., (1990) *Bio/Technology* 8:833–839).

Example 9

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant amino acid biosynthetic enzymes in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed, and the isolated fragment is inserted into a pUC18 vector carrying the seed expression cassette.

Plant amino acid biosynthetic enzymes are known to be localized in the chloroplasts. Accordingly, for those enzymes (or polypeptides representing part of the instant amino acid biosynthetic enzymes) that lack a chloroplast targeting signal, the DNA fragment to be inserted into the expression vector can be synthesized by PCR with primers encoding a chloroplast targeting signal. For example, a chloroplast transit sequence equivalent to the cts of the small subunit of ribulose 1,5-bisphosphate carboxylase from soybean (Berry-Lowe et al. (1982) *J. Mol. Appl. Genet.* 1:483–498) may be used.

Soybean embroys may then be transformed with the expression vector comprising sequences encoding a plant amino acid biosynthetic enzyme. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Kline et al. (1987) *Nature* (London) 327.70, U.S. Pat. No. 4,945,050). A Du Pont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al.(1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the biosynthetic enzyme and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µl spermidine (0.1 M), and 50 µL $CaCl_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 10

Analysis of Amino Acid Content of the Seeds of Transformed Plants

To analyze for expression of the chimeric genes in seeds and for the consequences of expression on the amino acid content in the seeds, a seed meal can be prepared by any of a number of suitable methods known to those skilled in the art. The seed meal can be partially or completely defatted, via hexane extraction for example, if desired. Protein extracts can be prepared from the meal and analyzed for enzyme activity. Alternatively the presence of any of the expressed enzymes can be tested for immunologically by methods well-known to those skilled in the art. To measure free amino acid composition of the seeds, free amino acids can be extracted from the meal and analyzed by methods known to those skilled in the art (Bieleski et al. (1966) *Anal. Biochem.* 17:278–293). Amino acid composition can then be determined using any commercially available amino acid analyzer. To measure total amino acid composition of the seeds, meal containing both protein-bound and free amino acids can be acid hydrolyzed to release the protein-bound amino acids and the composition can then be determined using any commercially available amino acid analyzer. Seeds expressing the instant amino acid biosynthetic enzymes and with altered lysine, threonine, methionine, cysteine and/or isoleucine content as compared to the wild type seeds can thus be identified and propagated.

To measure free amino acid composition of the seeds, free amino acids can be extracted from 8–10 milligrams of the seed meal in 1.0 mL of methanol/chloroform/water mixed in ratio of 12 v/5 v/3 v (MCW) at room temperature. The mixture can be vortexed and then centrifuged in an eppendorf microcentrifuge for about 3 min; approximately 0.8 mL of supernatant is then decanted. To this supernatant, 0.2 mL of chloroform is added followed by 0.3 mL of water. The mixture is then vortexed and centrifuged in an eppendorf microcentrifuge for about 3 min. The upper aqueous phase, approximately 1.0 mL, can then be removed and dried down in a Savant Speed Vac Concentrator. The samples are then hydrolyzed in 6N hydrochloric acid, 0.4% β-mercaptoethanol under nitrogen for 24 h at 110–120° C. Ten percent of the sample can then be analyzed using a Beckman Model 6300 amino acid analyzer using post-column ninhydrin detection. Relative free amino acid levels in the seeds are then compared as ratios of lysine, threonine, methionine, cysteine and/or isoleucine to leucine, thus using leucine as an internal standard.

Example 11

Expression of Chimeric Genes in Microbial Cells

The cDNAs encoding the instant plant amino acid biosynthetic enzymes can be inserted into the T7 E. coli expression vector pET24d (Novagen). Plasmid DNA containing a cDNA may be appropriately digested to release a nucleic acid fragment encoding the enzyme. This fragment may then be purified on a 1% NuSieve GTG™ low melting agarose gel (FMC). Buffer and agarose contain 10 µg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 µL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pET24d is digested, dephosphorylated with alkaline phosphatase (NEB) and deproteinized with phenol/chloroform as described above. The prepared vector pET24d and fragment can then be ligated at 16° C. for 15 hours followed by transformation into DH5 electrocompetent cells (GIBCO BRL). Transformants can be selected on agar plates containing 2xYT media and 50 µg/mL kanamycin. Transformants containing gene encoding the enzyme are then screened for the correct orientation with respect to pET24d T7 promoter by restriction enzyme analysis.

Clones in the correct orientation with respect to the T7 promoter can be transformed into BL21(DE3) competent cells (Novagen) and selected on 2xYT agar plates containing 50 µg/ml kanamycin. A colony arising from this transformation construct can be grown overnight at 30° C. in 2xYT media with 50 µg/mL kanamycin. The culture is then diluted two fold with fresh media, allowed to re-grow for 1 h, and induced by adding isopropyl-thiogalactopyranoside to 1 mM final concentration. Cells are then harvested by centrifugation after 3 h and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

Example 12

Evaluating Compounds for Their Ability to Inhibit the Activity of a Plant Amino Acid Biosynthetic Enzyme The plant amino acid biosynthetic enzymes described herein may be produced using any number of methods known to those skilled in the art. Such methods include, but are not limited to, expression in bacteria as described in Example 6, or expression in eukaryotic cell culture, in planta, and using viral expression systems in suitably infected organisms or cell lines. The instant enzymes may be expressed separately as mature proteins, or may be co-expressed in E. coli or another suitable expression background. In addition, whether expressed separately or in combination, the instant enzymes may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzymes. Examples of such proteases include thrombin, enterokinase and factor Xa. However, any protease can be used which specifically cleaves the peptide connecting the fusion protein and the biosynthetic enzyme.

Purification of the instant enzymes, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the enzymes are expressed as fusion proteins, the purification protocol may include the use of an affinity resin which is specific for the fusion protein tag attached to the expressed enzyme or an affinity resin containing ligands which are specific for the enzyme. For example, an enzyme may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the biosynthetic enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the plant amino acid biosynthetic enzymes disclosed herein. Assays may be conducted under well known experimental conditions which permit optimal enzymatic activity. Examples of assays for many of these enzymes can be found in *Methods in Enzymology* Vol. V, (Colowick and Kaplan eds.) Academic Press, New York or *Methods in Enzymology* Vol. XVII, (Tabor and Tabor eds.) Academic Press, New York. Specific examples may be found in the following references, each of which is incorporated herein by reference: dihydrodipicolinate reductase may be assayed as described in Farkas et al. (1965) *J. Biol. Chem.* 240: 4717–4722, or Cremer et al. (1988) *J. Gen.*

*Microbiol.* 134:3221–3229; diaminopimelate epimerase may be assayed as described in Work (1962) in *Methods in Enzymology* Vol. V, (Colowick and Kaplan eds.) 858–864, Academic Press, New York; threonine synthase may be assayed as described in Giovanelli et al. (1984) *Plant Physiol* 76: 285–292 or Curien et al. (1996) *FEBS Lett.* 390: 85–90; threonine deaminase may be assayed as described in Tomova et al. (1968) *Biochemistry (USSR)* 33: 200–208 or Dougall (1970) *Phytochemistry* 9: 959–964; and S-adenosylmethionine synthetase may be assayed as described in Mudd (1960) *Biochim. Biophys.Acta* 38:354–355 or Boerjan et al. (1994) *Plant Cell* 6:1401–1414.

What is claimed is:

1. An isolated polynucleotide comprising:
   (a) a nucleotide sequence encoding a polypeptide having S-adenosylmethionine synthetase activity, wherein the nucleotide sequence encoding the polypeptide and the nucleotide sequence of SEQ ID NO:38 have at least 90% sequence identity based on BLASTN alignment, or
   (b) a full-length complement of the nucleotide sequence of (a).

2. The polynucleotide of claim 1, wherein the nucleotide sequence encoding the polypeptide and the nucleotide sequence of SEQ ID NO:38 have at least 95% sequence identity based on BLASTN alignment.

3. The polynucleotide of claim 1, wherein the nucleotide sequence encoding the polypeptide comprises the nucleotide sequence of SEQ ID NO:38.

4. A vector comprising the polynucleotide of claim 1.

5. A recombinant DNA construct comprising the polynucleotide of claim 1 operably linked to a regulatory sequence.

6. A method for transforming a cell comprising transforming a cell with the polynucleotide of claim 1.

7. A cell comprising the recombinant DNA construct of claim 5.

8. A method for producing a plant comprising transforming a plant cell with the polynucleotide of claim 1 and regenerating a plant from the transformed plant cell.

9. A plant comprising the recombinant DNA construct of claim 5.

10. A seed comprising the recombinant DNA construct of claim 5.

* * * * *

UNITED STATES PATENT AND TRADEMARK OFFICE
CERTIFICATE OF CORRECTION

PATENT NO. : 7,022,895 B2  
APPLICATION NO. : 10/734698  
DATED : April 4, 2006  
INVENTOR(S) : Saverio Carl Falco Page 1 of 1

It is certified that error appears in the above-identified patent and that said Letters Patent is hereby corrected as shown below:

Front page of patent, section (75) Inventors: please delete "Stephen M. Allen, Wilmington, DE (US); J. Antoni Rafalski, Wilmington, DE (US); William D. Hitz, Wilmington, DE (US); Anthony John Kinney, Wilmington, DE (US); Lynne Marie Abell, Wilmington, DE (US); Catherine J. Thorpe, Hampshire (GB)"

Signed and Sealed this

Twenty-fifth Day of July, 2006

JON W. DUDAS  
*Director of the United States Patent and Trademark Office*

SEQUENCE LISTING (1) GENERAL INFORMATION:

(iii) NUMBER OF SEQUENCES: 43

(2) INFORMATION FOR SEQ ID NO: 1:

(i) SEQUENCE CHARACTERISTICS:
      (A) LENGTH: 908 base pairs
      (B) TYPE: nucleic acid
      (C) STRANDEDNESS: single
      (D) TOPOLOGY: linear (ii) MOLECULE TYPE: cDNA (vii) IMMEDIATE SOURCE:
      (B) CLONE: csiln.pk0042.a3

(xi) SEQUENCE DESCRIPTION: SEQ ID NO: 1:

```
ACGCGGGACA GATAAGTGGC ATGGACGAGC CGCTGGAGAT CCCTGTGCTG AACGACCTCA      60

CCATGGTTCT GGGCTCCATA GCGCAGTCGA GAGCAACCGG CGTGGTGGTC GACTTCAGC      120

AGCCTTCAGC TGTTTACGAC AATGTCAAGC AGGCAGCGGC GTTTGGTCTG AGCAGCGTC      180

TCTACGTTCC GAAAATCGAG CTAGAGACAG TGACTGAACT GTCAGCGTTC TGCGAGAAG      240

CAAGCGGCTG CTTGGTTGCG CCAACGCTGT CGATTGGGTC CGTGCTCCTT CAGCAAGCG      300

CTATACAGGC CTCGTTCCAC TACAGCAACG TTGAGATTGT GGAATCGAGA CCAAACCCA      360

CGGATCTTCC ATCGCAAGAT GCAATCCAGA TTGCAAACAA CATATCAGAC CTTGGTCAG      420

TATACAACAG GGAAGATATG GATTCCAGCA GTCCAGCCAG AGGCCAGCTG CTCGGGGAA      480

ACGGAGTGCG CGTGCACAGC ATGGTTCTCC CTGGTCTCGT CTCCAGCACG TCGATCAAC      540

TCTCTGGCCC AGGAGAGATG TACACCTTAC GGCATGACGT TGCGAATGTT CAGTGCCTG      600

TGCCAGGACT GATCCTGGCG ATACGGAAGG TGGTGCGGTT CAAGAACTTG ATTTATGGG      660

TAGAGAAGTT CTTGTAGTGA ACAACAAACA ACCAATGCAA AACATCGACA GGCAACAGG      720

AAGGCAGATA TCATCTGACG TCGCAACAAC CAAAACGACA GAGATTTGGA AAATAAAGG      780

TGCACAGAAG ACGTCTGGGG TTTTGTGTGC ACCAGGCTGC GCAGAGAACG TCTGTCATT      840

TGTGTGCACC ACTACGGCAC TACCTGCTGA GCGCGATTTT TATAAAAAAG GCATGGGAG      900

GAGATCAT                                                              908
```

(2) INFORMATION FOR SEQ ID NO: 2:

(i) SEQUENCE CHARACTERISTICS:
      (A) LENGTH: 224 amino acids
      (B) TYPE: amino acid
      (C) STRANDEDNESS: not relevant
      (D) TOPOLOGY: linear (ii) MOLECULE TYPE: peptide (vii) IMMEDIATE SOURCE:
      (B) CLONE: csiln.pk0042.a3

(xi) SEQUENCE DESCRIPTION: SEQ ID NO: 2:

```
Ala Gly Gln Ile Ser Gly Met Asp Glu Pro Leu Glu Ile Pro Val Leu
 1               5                  10                  15

Asn Asp Leu Thr Met Val Leu Gly Ser Ile Ala Gln Ser Arg Ala Thr
            20                  25                  30

Gly Val Val Asp Phe Ser Glu Pro Ser Ala Val Tyr Asp Asn Val
        35                  40                  45

Lys Gln Ala Ala Phe Gly Leu Ser Ser Val Tyr Val Pro Lys
 50                  55                  60

Ile Glu Leu Glu Thr Val Thr Glu Leu Ser Ala Phe Cys Glu Lys Ala
 65                  70                  75                  80

Ser Gly Cys Leu Val Ala Pro Thr Leu Ser Ile Gly Ser Val Leu Leu
                85                  90                  95

Gln Gln Ala Ala Ile Gln Ala Ser Phe His Tyr Ser Asn Val Glu Ile
                100                 105                 110

Val Glu Ser Arg Pro Asn Pro Ser Asp Leu Pro Ser Gln Asp Ala Ile
            115                 120                 125

Gln Ile Ala Asn Asn Ile Ser Asp Leu Gly Gln Ile Tyr Asn Arg Glu
130                 135                 140

Asp Met Asp Ser Ser Ser Pro Ala Arg Gly Gln Leu Leu Gly Glu Asp
145                 150                 155                 160

Gly Val Arg Val His Ser Met Val Leu Pro Gly Leu Val Ser Ser Thr
                165                 170                 175

Ser Ile Asn Phe Ser Gly Pro Gly Glu Met Tyr Thr Leu Arg His Asp
                180                 185                 190

Val Ala Asn Val Gln Cys Leu Met Pro Gly Leu Ile Leu Ala Ile Arg
                195                 200                 205

Lys Val Val Arg Phe Lys Asn Leu Ile Tyr Gly Leu Glu Lys Phe Leu
            210                 215                 220
```

(2) INFORMATION FOR SEQ ID NO: 3:

(i) SEQUENCE CHARACTERISTICS:
        (A) LENGTH: 339 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: rls2.pk0017.d3

(xi) SEQUENCE DESCRIPTION: SEQ ID NO: 3:

```
AAGATTGGCA GGAGAAATGC AGCAAAGGTC CTCTGCTCAA CGCAGATGCC GCCATCTCAG      60

AGCACAATCA AGGTTGTTAT CATTGGGGCG ACAAAAGAGA TTGGAAGAAC GGCAATAGC      120

GCAGTAAGTA AAGCAAGGGG AATGGAGCTT GCAGGGGCCA TAGATTCTCA GTGTATAGG      180

CTAGATGCAG GAGAGATAAG TGGCATGGGA AGAACCCTGG AAATTCCGGT GCTCAATGA      240

CTCACAATGG TTCTGGGCTC AATTGCACAA ACCAGAGCAA CTGGAGTGGT GGTTGATTT      300

AGTGAACCTT CAACTGTTTA TGATAATGTC AAACAGGCA                            339
```

(2) INFORMATION FOR SEQ ID NO: 4:

(i) SEQUENCE CHARACTERISTICS:
        (A) LENGTH: 113 amino acids
        (B) TYPE: amino acid
        (C) STRANDEDNESS: not relevant
        (D) TOPOLOGY: linear (ii) MOLECULE TYPE: peptide (vii) IMMEDIATE SOURCE:
    (B) CLONE: rls2.pk0017.d3

(xi) SEQUENCE DESCRIPTION: SEQ ID NO: 4:

```
Lys Ile Gly Arg Arg Asn Ala Ala Lys Val Leu Cys Ser Thr Gln Met
1               5                   10                  15

Pro Pro Ser Gln Ser Thr Ile Lys Val Val Ile Ile Gly Ala Thr Lys
                20                  25                  30

Glu Ile Gly Arg Thr Ala Ile Ala Ala Val Ser Lys Ala Arg Gly Met
            35                  40                  45

Glu Leu Ala Gly Ala Ile Asp Ser Gln Cys Ile Gly Leu Asp Ala Gly
50                  55                  60

Glu Ile Ser Gly Met Gly Arg Thr Leu Glu Ile Pro Val Leu Asn Asp
65                  70                  75                  80

Leu Thr Met Val Leu Gly Ser Ile Ala Gln Thr Arg Ala Thr Gly Val
                85                  90                  95

Val Val Asp Phe Ser Glu Pro Ser Thr Val Tyr Asp Asn Val Lys Gln
                100                 105                 110

Ala
```

(2) INFORMATION FOR SEQ ID NO: 5:

(i) SEQUENCE CHARACTERISTICS:
        (A) LENGTH: 275 amino acids
        (B) TYPE: amino acid
        (C) STRANDEDNESS: not relevant
        (D) TOPOLOGY: linear (ii) MOLECULE TYPE: peptide (vi) ORIGINAL SOURCE:
        (A) ORGANISM: Synechocystus sp (xi) SEQUENCE DESCRIPTION: SEQ ID NO: 5:

```
Met Ala Asn Gln Asp Leu Ile Pro Val Val Val Asn Gly Ala Ala Gly
1               5                   10                  15

Lys Met Gly Arg Glu Val Ile Lys Ala Val Ala Gln Ala Pro Asp Leu
                20                  25                  30

Gln Leu Val Gly Ala Val Asp His Asn Pro Ser Leu Gln Gly Gln Asp
            35                  40                  45

Ile Gly Glu Val Val Gly Ile Ala Pro Leu Glu Val Pro Val Leu Ala
50                  55                  60

Asp Leu Gln Ser Val Leu Val Leu Ala Thr Gln Glu Lys Ile Gln Gly
65                  70                  75                  80

Val Met Val Asp Phe Thr His Pro Ser Gly Val Tyr Asp Asn Val Arg
                85                  90                  95

Ser Ala Ile Ala Tyr Gly Val Arg Pro Val Val Gly Thr Thr Gly Leu
                100                 105                 110

Ser Glu Gln Gln Ile Gln Asp Leu Gly Asp Phe Ala Glu Lys Ala Ser
            115                 120                 125

Thr Gly Cys Leu Ile Ala Pro Asn Phe Ala Ile Gly Val Leu Leu Met
            130                 135                 140

Gln Gln Ala Ala Val Gln Ala Cys Gln Tyr Phe Asp His Val Glu Ile
145                 150                 155                 160

Ile Glu Leu His His Asn Gln Lys Ala Asp Ala Pro Ser Gly Thr Ala
                165                 170                 175
```

```
Ile Lys Thr Ala Gln Met Leu Ala Glu Met Gly Lys Thr Phe Asn Pro
            180                 185                 190

Pro Ala Val Glu Glu Lys Glu Thr Ile Ala Gly Ala Lys Gly Gly Leu
        195                 200                 205

Gly Pro Gly Gln Ile Pro Ile His Ser Ile Arg Leu Pro Gly Leu Ile
    210                 215                 220

Ala His Gln Glu Val Leu Phe Gly Ser Pro Gly Gln Leu Tyr Thr Ile
225                 230                 235                 240

Arg His Asp Thr Thr Asp Arg Ala Cys Tyr Met Pro Gly Val Leu Leu
                245                 250                 255

Gly Ile Arg Lys Val Val Glu Leu Lys Gly Leu Val Tyr Gly Leu Glu
            260                 265                 270

Lys Leu Leu
        275

(2) INFORMATION FOR SEQ ID NO: 6:

(i) SEQUENCE CHARACTERISTICS:
        (A) LENGTH: 1012 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: chp2.pk0008.h4

(xi) SEQUENCE DESCRIPTION: SEQ ID NO: 6:

TATTGCCAGA GATGTGTGGT AATGGAGTCC GTTGCTTCGC TCGGTTTATA GCCGAGATTG       60

AAAATCTGCA GGGGACAAAT AGATTCACTA TTCATACTGG TGCTGGAAAG ATCGTTCCT       120

AAATACAAAG TGATGGGCAG GTAAAGGTTG ATATGGGCGA GCCTATCCTT TCTGGACTA      180

ACATCCCCAC AAAACTGCTA GCTACCAAGA ACAAAGCTGT TGTTCAAGCT GAATTGGCA      240

TTGAGGGCTT AACATGGCAT GTCACATGTG TTAGCATGGG AAACCCTCAC TGTGTCACA      300

TTGGTGCAAA TGAGTTAAAG GTATTGCAGG TCGACGATTT AAAACTTAGC GAAATTGGG      360

CTAAATTTGA GCATCATGAA ATGTTTCCTG CTCGCACAAA CACAGAATTC GTACAGGTT      420

TGTCTCGCTC ACACCTCAAA ATGCGGGTCT GGGAACGTGG TGCTGGAGCA ACTCTTGCC      480

GTGGTACTGG TGCTTGTGCA GTGGTTGTTG CAGCTGTTCT TGAGGGTCGA GCTGAGCGG      540

AATGTGTAGT TGATTTGCCT GGCGGGCCAT TGGAAATTGA GTGGAGGGAG GATGACAAT      600

ATGTTTACAT GACTGGTCCT GCAGAGGTCG TCTTTTATGG ATCTGTTGTT CACTAGGTA      660

TGGGGACCAA GATAGAAGGG TTGGCTGCCA CTCAGAGCTT GTGAGATTGG TTATAGTAT      720

CATGAAACAG AGTGTTCTGG TACCAGTACA CTTGTTCAGA TATTCTTAAT TATGATTGC      780

TGATTTGGGT AGCMGTAGAG GCTTCCTTTT GAAGCATTCT AGTGTTCMCC TTTTGTACT      840

CTTTAGTTTG TCAGGTTTGA ACACTACATG GGTAACATGT CYTTCCCACC ATTTTCYGT      900

TCTTTTCTTT GTAAGTGAAC GCCAATGCAG TTTTAGTATT GTTTTCTATA GATTTGTCT      960

GATGCACTGG GCTTACTACT TATTTTCTGG TATGAATGCT GCCTATTTCC TG           1012

(2) INFORMATION FOR SEQ ID NO: 7:

(i) SEQUENCE CHARACTERISTICS:
        (A) LENGTH: 217 amino acids
        (B) TYPE: amino acid
        (C) STRANDEDNESS: not relevant
```

```
        (D) TOPOLOGY: linear (ii) MOLECULE TYPE: peptide (vii) IMMEDIATE SOURCE:
         (B) CLONE: chp2.pk0008.h4

(xi) SEQUENCE DESCRIPTION: SEQ ID NO: 7:

Leu Pro Glu Met Cys Gly Asn Gly Val Arg Cys Phe Ala Arg Phe Ile
1               5                   10                  15

Ala Glu Ile Glu Asn Leu Gln Gly Thr Asn Arg Phe Thr Ile His Thr
            20                  25                  30

Gly Ala Gly Lys Ile Val Pro Glu Ile Gln Ser Asp Gly Gln Val Lys
        35                  40                  45

Val Asp Met Gly Glu Pro Ile Leu Ser Gly Leu Asp Ile Pro Thr Lys
    50                  55                  60

Leu Leu Ala Thr Lys Asn Lys Ala Val Val Gln Ala Glu Leu Ala Val
65                  70                  75                  80

Glu Gly Leu Thr Trp His Val Thr Cys Val Ser Met Gly Asn Pro His
                85                  90                  95

Cys Val Thr Phe Gly Ala Asn Glu Leu Lys Val Leu Gln Val Asp Asp
            100                 105                 110

Leu Lys Leu Ser Glu Ile Gly Pro Lys Phe Glu His His Glu Met Phe
        115                 120                 125

Pro Ala Arg Thr Asn Thr Glu Phe Val Gln Val Leu Ser Arg Ser His
    130                 135                 140

Leu Lys Met Arg Val Trp Glu Arg Gly Ala Gly Ala Thr Leu Ala Cys
145                 150                 155                 160

Gly Thr Gly Ala Cys Ala Val Val Ala Ala Val Leu Glu Gly Arg
                165                 170                 175

Ala Glu Arg Lys Cys Val Val Asp Leu Pro Gly Gly Pro Leu Glu Ile
            180                 185                 190

Glu Trp Arg Glu Asp Asp Asn His Val Tyr Met Thr Gly Pro Ala Glu
        195                 200                 205

Val Val Phe Tyr Gly Ser Val Val His
    210                 215

(2) INFORMATION FOR SEQ ID NO: 8:

(i) SEQUENCE CHARACTERISTICS:
        (A) LENGTH: 481 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
         (B) CLONE: rls48.pk0036.h10

(xi) SEQUENCE DESCRIPTION: SEQ ID NO: 8:

TGTATCCGGC GCCGACGGTG TGATCTTCGT CATGCCGGGG GTCAATGGCG CGGACTACAC    60

CATGAGGATC TTCAACTCGG ACGGCAGTGA GCCGGAGATG TGTGGCAATG GAGTCCGTT    120

CTTTGCCCGG TTTATAGCTG AGCTTGAAAA CCTACAGGGA ACACATAGCT TCAAAATTC    180

CACTGGCGCT GGGCTAATCA TTCCTGAAAT ACAAAATGAT GGCAAGGTAA AGGTTGATA    240

GGGCCAGCCC ATTCTCTCTG GACCAGATAT TCCAACAAAA CTGCCATCCA CCAAGAATG    300

AGCCGTTGTC CAAGCTGATT TGGGCAGTTG ATGGCTCAAC ATGGCAAGTA ACCTGTGTT    360
```

```
GCATGGGCAA TCCACATTGT GTCACATTTG GCACAAAGGA GCTCAAGGTT TTGCATGTT        420

ATGATTAAAG CTTAATGATA TTGGGGCCTA AATTCAGCAT CATGAAATGT TCCTGCCCC        480

C                                                                      481
```

(2) INFORMATION FOR SEQ ID NO: 9:

(i) SEQUENCE CHARACTERISTICS:
        (A) LENGTH: 85 amino acids
        (B) TYPE: amino acid
        (C) STRANDEDNESS: not relevant
        (D) TOPOLOGY: linear (ii) MOLECULE TYPE: peptide (vii) IMMEDIATE SOURCE:
        (B) CLONE: rls48.pk0036.h10

(xi) SEQUENCE DESCRIPTION: SEQ ID NO: 9:

```
Val Ser Gly Ala Asp Gly Val Ile Phe Val Met Pro Gly Val Asn Gly
1               5                   10                  15

Ala Asp Tyr Thr Met Arg Ile Phe Asn Ser Asp Gly Ser Glu Pro Glu
                20                  25                  30

Met Cys Gly Asn Gly Val Arg Cys Phe Ala Arg Phe Ile Ala Glu Leu
            35                  40                  45

Glu Asn Leu Gln Gly Thr His Ser Phe Lys Ile His Thr Gly Ala Gly
        50                  55                  60

Leu Ile Ile Pro Glu Ile Gln Asn Asp Gly Lys Val Lys Val Asp Met
65                  70                  75                  80

Gly Gln Pro Ile Leu
                85
```

(2) INFORMATION FOR SEQ ID NO: 10:

(i) SEQUENCE CHARACTERISTICS:
        (A) LENGTH: 1301 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

```
ATCCCTTATT AAGCAGGGGT TTCGCGGCGC GAGACGGTGA CACTGGCAGA GTGGAATTTC        60

CGCCGCCATT CGAAGCTACA GCGATGGCCA TAACCGCCAC CATTTCCGTT CCCCTCACA        120

CCCCCAGTCG CCGCACTCTC ACCTCCGTCA ATAGCCTCTC TCCCCTTTCT ACCCGATCC        180

CTTTGCCCAC ACCGCAACGC ACTTTCAAAT ACCCTAATTC GCGCCTCGTC GTGTCTTCC        240

TGAGCACCGA AACAGCCGTC AAAACTTCAT CCGCCTCCTT CCTCAACCGC AAGGAGTCC        300

GCTTCCTCCA TTTCGCCAAG TACCACGGCC TCGGAAACGA CTTCGTTTTG ATTGACAAT        360

GAGACTCCTC CGAGCCCAAG ATCAGTGCTG AGAAAGCGGT GCAACTGTGT GATCGGAAC        420

TCGGCGTTGG AGCTGACGGA GTTATCTTTG TCTTGCCTGG CATCAGTGGC ACCGATTAT        480

CCATGAGGAT TTTTAACTCT GATGGTAGTG AGCCTGAGAT GTGTGGCAAT GGAGTTCGA        540

GCTTTGCCAA ATTTGTTTCT CAGCTTGAGA ATTTACATGG GAGGCATAGT TTTACCATT        600

ATACTGGTGC TGGTCTGATT ATTCCTGAAG TCTTGGAGGA TGGAAATGTC AGAGTTGAT        660

TGGGGGAGCC AGTTCTTAAA GCCTTGGATG TGCCTACTAA ATTACCTGCA AATAAGGAT        720

ATGCTGTTGT TAAATCACAG CTAGTTGTAG ATGGAGTTAT TTGGCATGTG ACCTGTGTT        780
```

-continued

```
GCATGGGGAA TCCACACTGT GTAACTTTCA GTAGAGAAGG AAGCCAGAAT TTGCTTGTT       840

ATGAATTGAA GCTAGCAGAA ATTGGGCCAA AATTTGAACA TCATGAGGTG TTCCCTGCA       900

GAACTAACAC AGAGTTTGTG CAAGTATTAT CTAACTCTCA CTTGAAAATG CGTGTTTGG       960

AGCGGGGAGC AGGAGCAACC CTAGCCTGTG AACTGGAGC TTGTGCTACT GTTGTTGC       1020

CAGTTCTTGA GGGTCGTGCT GGGAGGAATT GCACGGTTGA TCTACCTGGA GGGCCTCT       1080

AGATTGAGTG GAGGGAGGAA GATAATCATG TTTATATGAC AGGCTCAGCC GATGTAGT       1140

ATTATGGTTC TTTGCCCCTT TGATATGTTG CCCCCATTGT TAAACCCAAT ATGGAATT       1200

GAATTGGTGA ATAATATTTG TATGAGAGGT GGACTTTCTG CTTGTTCCTA ATATTTTG       1260

ACGTCTTTAT AAAAAAAAAA AAAAAAAAAA AAAAAAAAA A                         1301
```

(2) INFORMATION FOR SEQ ID NO: 11:

(i) SEQUENCE CHARACTERISTICS:
        (A) LENGTH: 359 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 11:

```
Met Ala Ile Thr Ala Thr Ile Ser Val Pro Leu Thr Ser Pro Ser Arg
 1               5                   10                  15

Arg Thr Leu Thr Ser Val Asn Ser Leu Ser Pro Leu Ser Thr Arg Ser
            20                  25                  30

Thr Leu Pro Thr Pro Gln Arg Thr Phe Lys Tyr Pro Asn Ser Arg Leu
        35                  40                  45

Val Val Ser Ser Met Ser Thr Glu Thr Ala Val Lys Thr Ser Ser Ala
    50                  55                  60

Ser Phe Leu Asn Arg Lys Glu Ser Gly Phe Leu His Phe Ala Lys Tyr
65                  70                  75                  80

His Gly Leu Gly Asn Asp Phe Val Leu Ile Asp Asn Arg Asp Ser Ser
                85                  90                  95

Glu Pro Lys Ile Ser Ala Glu Lys Ala Val Gln Leu Cys Asp Arg Asn
            100                 105                 110

Phe Gly Val Gly Ala Asp Gly Val Ile Phe Val Leu Pro Gly Ile Ser
        115                 120                 125

Gly Thr Asp Tyr Thr Met Arg Ile Phe Asn Ser Asp Gly Ser Glu Pro
    130                 135                 140

Glu Met Cys Gly Asn Gly Val Arg Cys Phe Ala Lys Phe Val Ser Gln
145                 150                 155                 160

Leu Glu Asn Leu His Gly Arg His Ser Phe Thr Ile His Thr Gly Ala
                165                 170                 175

Gly Leu Ile Ile Pro Glu Val Leu Glu Asp Gly Asn Val Arg Val Asp
            180                 185                 190

Met Gly Glu Pro Val Leu Lys Ala Leu Asp Val Pro Thr Lys Leu Pro
        195                 200                 205

Ala Asn Lys Asp Asn Ala Val Val Lys Ser Gln Leu Val Val Asp Gly
    210                 215                 220

Val Ile Trp His Val Thr Cys Val Ser Met Gly Asn Pro His Cys Val
225                 230                 235                 240

Thr Phe Ser Arg Glu Gly Ser Gln Asn Leu Leu Val Asp Glu Leu Lys
                245                 250                 255
```

```
Leu Ala Glu Ile Gly Pro Lys Phe Glu His His Glu Val Phe Pro Ala
            260                 265                 270

Arg Thr Asn Thr Glu Phe Val Gln Val Leu Ser Asn Ser His Leu Lys
            275                 280                 285

Met Arg Val Trp Glu Arg Gly Ala Gly Ala Thr Leu Ala Cys Gly Thr
            290                 295                 300

Gly Ala Cys Ala Thr Val Val Ala Ala Val Leu Glu Gly Arg Ala Gly
305                 310                 315                 320

Arg Asn Cys Thr Val Asp Leu Pro Gly Gly Pro Leu Gln Ile Glu Trp
                325                 330                 335

Arg Glu Glu Asp Asn His Val Tyr Met Thr Gly Ser Ala Asp Val Val
            340                 345                 350

Tyr Tyr Gly Ser Leu Pro Leu
            355
```

(2) INFORMATION FOR SEQ ID NO: 12:

(i) SEQUENCE CHARACTERISTICS:
        (A) LENGTH: 602 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: wlm24.pk0030.g4

(xi) SEQUENCE DESCRIPTION: SEQ ID NO: 12:

```
CTCCACCGCC CCCTCCTCGG GCGGTCGCCT CCTCCGTCCG TTCTGTGGGA ATCCGCGCCC    60
CCGCCGCGCC GTCGCCTCGA TGGCCGTGTC CGCTCCCAAG TCGCCAGCCG CCGCCTCGT   120
CCTCGAGCGC CGCGAGTCCG AGCGCGCGCT CCACTTCGTG AAGTACCAGG GCCTCGGCA   180
CGACTTCATA ATGGTCGACA ACAGGGATTC GGCCGTACCG AAGGTGACAC CGGAGGAGG   240
GGCGAAGCTA TGCGACCGAA ACTTTGGGTA TTGGGTGCTG ATGGCGTCAT CTTCGTCCT   300
CCGGGGGTCA ACGGCGCGGA CTACACTATG AGGATATTCA ACTCCGATGG CAGCAACCG   360
AATGTNTGGN ATGGATTCGT TGCTTGCTCG CTTTATACGG AGTTGAAATC TACANGGAA   420
CATACTTCAA ACAANAGGG GGCTGGATTA ATATCCTGAA ATANANACAT GNAAGTTAN   480
TNATATGGGC AACAATCTTA TGGCANATTT CANAAAATGC ATCACAAGAT AACTTNTAA   540
ACGATTGAAT TAGGCAANAG AANTACCGTT ATAGGAACCC ATGAANCTTG TNAAATTAA   600
GT                                                                602
```

(2) INFORMATION FOR SEQ ID NO: 13:

(i) SEQUENCE CHARACTERISTICS:
        (A) LENGTH: 80 amino acids
        (B) TYPE: amino acid
        (C) STRANDEDNESS: not relevant
        (D) TOPOLOGY: linear (ii) MOLECULE TYPE: peptide (vii) IMMEDIATE SOURCE:
        (B) CLONE: wlm24.pk0030.g4

(xi) SEQUENCE DESCRIPTION: SEQ ID NO: 13:

```
Ala Leu His Phe Val Lys Tyr Gln Gly Leu Gly Asn Asp Phe Ile Met
1               5                   10                  15

Val Asp Asn Arg Asp Ser Ala Val Pro Lys Val Thr Pro Glu Glu Ala
```

```
              20                  25                  30
Ala Lys Leu Cys Asp Arg Asn Phe Gly Xaa Gly Ala Asp Gly Val Ile
         35                  40                  45
Phe Val Leu Pro Gly Val Asn Gly Ala Asp Tyr Thr Met Arg Ile Phe
     50                  55                  60
Asn Ser Asp Gly Ser Asn Arg Asn Val Trp Xaa Gly Phe Val Ala Cys
 65                  70                  75                  80
```

(2) INFORMATION FOR SEQ ID NO: 14:

(i) SEQUENCE CHARACTERISTICS:
        (A) LENGTH: 279 amino acids
        (B) TYPE: amino acid
        (C) STRANDEDNESS: not relevant
        (D) TOPOLOGY: linear (ii) MOLECULE TYPE: peptide (vi) ORIGINAL SOURCE:
        (A) ORGANISM: Synechocystus sp (xi) SEQUENCE DESCRIPTION: SEQ ID NO: 14:

```
Met Ala Leu Ser Phe Ser Lys Tyr His Gly Leu Gly Asn Asp Phe Ile
 1               5                  10                  15
Leu Val Asp Asn Arg Gln Ser Thr Glu Pro Cys Leu Thr Pro Asp Gln
             20                  25                  30
Ala Gln Gln Leu Cys Asp Arg His Phe Gly Ile Gly Ala Asp Gly Val
         35                  40                  45
Ile Phe Ala Leu Pro Gly Gln Gly Gly Thr Asp Tyr Thr Met Arg Ile
     50                  55                  60
Phe Asn Ser Asp Gly Ser Glu Pro Glu Met Cys Gly Asn Gly Ile Arg
 65                  70                  75                  80
Cys Leu Ala Lys Phe Leu Ala Asp Leu Glu Gly Val Glu Glu Lys Thr
                 85                  90                  95
Tyr Arg Ile His Thr Leu Ala Gly Val Ile Thr Pro Gln Leu Leu Ala
             100                 105                 110
Asp Gly Gln Val Lys Val Asp Met Gly Glu Pro Gln Leu Leu Ala Glu
         115                 120                 125
Leu Ile Pro Thr Thr Leu Ala Pro Ala Gly Glu Lys Val Val Asp Leu
     130                 135                 140
Pro Leu Ala Val Ala Gly Gln Thr Trp Ala Val Thr Cys Val Ser Met
145                 150                 155                 160
Gly Asn Pro His Cys Leu Thr Phe Val Asp Val Asp Ser Leu Asn
                 165                 170                 175
Leu Thr Glu Ile Gly Pro Leu Phe Glu His His Pro Gln Phe Ser Gln
             180                 185                 190
Arg Thr Asn Thr Glu Phe Ile Gln Val Leu Gly Ser Asp Arg Leu Lys
         195                 200                 205
Met Arg Val Trp Glu Arg Gly Ala Gly Ile Thr Leu Ala Cys Gly Thr
     210                 215                 220
Gly Ala Cys Ala Thr Val Ala Ala Val Leu Thr Gly Arg Gly Asp
225                 230                 235                 240
Arg Arg Cys Thr Val Glu Leu Pro Gly Gly Asn Leu Glu Ile Glu Trp
                 245                 250                 255
Ser Ala Gln Asp Asn Arg Leu Tyr Met Thr Gly Pro Ala Gln Arg Val
             260                 265                 270
Phe Ser Gly Gln Ala Glu Ile
```

(2) INFORMATION FOR SEQ ID NO: 15:

(i) SEQUENCE CHARACTERISTICS:
        (A) LENGTH: 1160 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: cc2.pk0031.c9

(xi) SEQUENCE DESCRIPTION: SEQ ID NO: 15:

```
GTCGGCTGCG CGTCCACGGG AGACACCTCC GCCGCGCTCT CGGCCTACTG CGCAGCCGCG      60
GGAATCCCCG CCATCGTGTT CCTGCCAGCG GACCGCATCT CGCTGCAGCA GCTCATCCA      120
CCGATCGCCA ACGGCGCCAC CGTGCTCTCT CTAGACACTG ATTTTGATGG CTGCATGCG      180
CTCATTCGCG AGGTCACTGC AGAGCTGCCA ATCTACCTTG CCAATTCGCT CAACCCGCT      240
CGCCTTGAGG GGCAGAAGAC AGCGGCCATC GAGATATTGC AGCAGTTCAA TTGGCAGGT      300
CCAGATTGGG TCATTGTTCC AGGAGGCAAT CTTGGGAATA TCTATGCATT CTACAAGGG      360
TTTGAGATGT GCCGCGTTCT TGGACTTGTT GATCGCGTGC CACGGCTTGT CTGCGCACA      420
GCTGCAAATG CAAATCCATT GTACCGGTAC TACAAGTCAG GTTGGACTGA GTTTGAGCC      480
CAAACTGCCG AGACTACATT TGCATCTGCG ATACAGATTG GTGATCCTGT ATCTGTTGA      540
CGTGCGGTGG TCGCGCTGAA GGCCACTGAC GGTATTGTGG AGGAGGCTAC AGAGGAGGA      600
CTAATGGATG CAACGGCGCT TGCTGACCGC ACTGGGATGT TGCTTGCCC ACATACTGG       660
GTTGCACTTG CTGCTTTGTT TAAGCTTCAG GGTCAGCGTA TAATTGGCCC TAATGACCG      720
ACTGTGGTTG TTAGCACAGC TCATGGGCTG AAGTTCACGC AGTCAAAGAT TGACTACCA      780
GACAAAAACA TCAAAGACAT GGTTTGCCAG TATGCTAATC CACCGATCAG TGTGAAGGC      840
GACTTTGGTT CTGTGATGGA TGTTCTCCAG AAAAATCTCA ATGGTAAGAT ATAAAGTTA      900
ATGATTAATT AACCCTCCAA ACTGTTTTTT TTTGTTTTTT CGTTCCAGGA ATTTTATTC      960
TGAGTCTTTC AACTTTGTTT GGTGAACATG GTATGGTGCT AAAATCTAGA CCTAATAC      1020
TGTAGTACTA GTTCTGGAGG CTCTTTTGGT TGTAGGTCGA AGTGGATAGA GCTGTTCC      1080
GTACTTTATC TGTTTCATGT AATATGAATA ATAAATTATG GTCTAAATAT TTGAATAA      1140
AATCGTTTGG AATGACCCAC                                                 1160
```

(2) INFORMATION FOR SEQ ID NO: 16:

(i) SEQUENCE CHARACTERISTICS:
        (A) LENGTH: 297 amino acids
        (B) TYPE: amino acid
        (C) STRANDEDNESS: not relevant
        (D) TOPOLOGY: linear (ii) MOLECULE TYPE: peptide (vii) IMMEDIATE SOURCE:
        (B) CLONE: cc2.pk0031.c9

(xi) SEQUENCE DESCRIPTION: SEQ ID NO: 16:

```
Val Gly Cys Ala Ser Thr Gly Asp Thr Ser Ala Ala Leu Ser Ala Tyr
 1               5                  10                  15
Cys Ala Ala Ala Gly Ile Pro Ala Ile Val Phe Leu Pro Ala Asp Arg
             20                  25                  30
```

```
Ile Ser Leu Gln Gln Leu Ile Gln Pro Ile Ala Asn Gly Ala Thr Val
        35                  40                  45

Leu Ser Leu Asp Thr Asp Phe Asp Gly Cys Met Arg Leu Ile Arg Glu
 50                  55                  60

Val Thr Ala Glu Leu Pro Ile Tyr Leu Ala Asn Ser Leu Asn Pro Leu
 65                  70                  75                  80

Arg Leu Glu Gly Gln Lys Thr Ala Ala Ile Glu Ile Leu Gln Gln Phe
                 85                  90                  95

Asn Trp Gln Val Pro Asp Trp Val Ile Val Pro Gly Gly Asn Leu Gly
            100                 105                 110

Asn Ile Tyr Ala Phe Tyr Lys Gly Phe Glu Met Cys Arg Val Leu Gly
            115                 120                 125

Leu Val Asp Arg Val Pro Arg Leu Val Cys Ala Gln Ala Ala Asn Ala
130                 135                 140

Asn Pro Leu Tyr Arg Tyr Tyr Lys Ser Gly Trp Thr Glu Phe Glu Pro
145                 150                 155                 160

Gln Thr Ala Glu Thr Thr Phe Ala Ser Ala Ile Gln Ile Gly Asp Pro
                165                 170                 175

Val Ser Val Asp Arg Ala Val Val Ala Leu Lys Ala Thr Asp Gly Ile
            180                 185                 190

Val Glu Glu Ala Thr Glu Glu Leu Met Asp Ala Thr Ala Leu Ala
            195                 200                 205

Asp Arg Thr Gly Met Phe Ala Cys Pro His Thr Gly Val Ala Leu Ala
210                 215                 220

Ala Leu Phe Lys Leu Gln Gly Gln Arg Ile Ile Gly Pro Asn Asp Arg
225                 230                 235                 240

Thr Val Val Val Ser Thr Ala His Gly Leu Lys Phe Thr Gln Ser Lys
                245                 250                 255

Ile Asp Tyr His Asp Lys Asn Ile Lys Asp Met Val Cys Gln Tyr Ala
            260                 265                 270

Asn Pro Pro Ile Ser Val Lys Ala Asp Phe Gly Ser Val Met Asp Val
275                 280                 285

Leu Gln Lys Asn Leu Asn Gly Lys Ile
290                 295
```

(2) INFORMATION FOR SEQ ID NO: 17:

(i) SEQUENCE CHARACTERISTICS:
        (A) LENGTH: 325 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: cs1.pk0058.g5

(xi) SEQUENCE DESCRIPTION: SEQ ID NO: 17:

```
ATGGCTTGCA AGTACTCCAA CCCGCCTGTG AGCGTGAAGG CTGACTTTGG CGCCGTGATG    60

GATGTGCTGA AGAAGAGGCT CAAGGGCAAG CTCTGAGCGC CTGTGCCTGG CTAATGCAA    120

CAACTGATTG GAATGCAGTG GTTTCGTCGG TATCGGGGGG TCTTTTAGGC TTCAGAAAT    180

CTGTCTGGGT TAGACTATTT GTTTGTGGAG TTTAGCAGGA GAATGGCTAT CTCTCCTGC    240

AGACTGGCGC TCTTTCTTGT GCTACGAATG TGTTACCATG GATAATAAGT GTAGTCGCT    300

TCGGATTGAA TAATCAAAAA AAAAN                                         325
```

(2) INFORMATION FOR SEQ ID NO: 18:

(i) SEQUENCE CHARACTERISTICS:
       (A) LENGTH: 31 amino acids
       (B) TYPE: amino acid
       (C) STRANDEDNESS: not relevant
       (D) TOPOLOGY: linear (ii) MOLECULE TYPE: peptide (vii) IMMEDIATE SOURCE:
       (B) CLONE: cs1,pk0058.g5

(xi) SEQUENCE DESCRIPTION: SEQ ID NO: 18:

```
Met Ala Cys Lys Tyr Ser Asn Pro Pro Val Ser Val Lys Ala Asp Phe
1               5                   10                  15

Gly Ala Val Met Asp Val Leu Lys Lys Arg Leu Lys Gly Lys Leu
            20                  25                  30
```

(2) INFORMATION FOR SEQ ID NO: 19:

(i) SEQUENCE CHARACTERISTICS:
       (A) LENGTH: 528 base pairs
       (B) TYPE: nucleic acid
       (C) STRANDEDNESS: single
       (D) TOPOLOGY: linear (ii) MOLECULE TYPE: cDNA (vii) IMMEDIATE SOURCE:
       (B) CLONE: rls72.pk0018.e7

(xi) SEQUENCE DESCRIPTION: SEQ ID NO: 19:

```
ACACCCAACA CGCAGACTTG ACAGATTCTG CTACTACAAA TCCTGCATAT TTAACAGCGC      60
TGCAACTCGA CGATGGAGAA CGGTGCTGCA ACCAACGGGG CGTCGGAGAA GTCGCACTC      120
CCTTCACAGA CCTACCTCTC CACAAGGGGA GACGATTATG GCTCTCATT CGAGACCGT       180
GTCCTCAAAG TCTTGCGGC TGACGGGGGT CTTTTCCTGC CCGAGGAAGT GCCCGCGGC       240
ACCGAGTGGC AAAGCTGGAA AGACCTGCCC TACACCGAGC TTGCCGTCAA GGTTCTCAG      300
TTGTACATCT CCCCCGCCGA GGTGCCGACG GAAGACCTCA GGGCGCTCGT CGAGCGCAG      360
TACTCGACCT TCCGATCCAA GGAGGTTGTG CCGCTGGTGA AGCTGGAGGA CAACCTTCA      420
CTGCTGGAGC TATTCCACGG CCCCAACTAC TCGTTCAAGG ACTGCGCGCT GCAATTCCT      480
GGTAACCTCN TCGAGTACTT TTGACTCNCA AGAACAAGGG AAAGGAGG                 528
```

(2) INFORMATION FOR SEQ ID NO: 20:

(i) SEQUENCE CHARACTERISTICS:
       (A) LENGTH: 143 amino acids
       (B) TYPE: amino acid
       (C) STRANDEDNESS: not relevant
       (D) TOPOLOGY: linear (ii) MOLECULE TYPE: peptide (vii) IMMEDIATE SOURCE:
       (B) CLONE: rls72.pk0018.e7

(xi) SEQUENCE DESCRIPTION: SEQ ID NO: 20:

```
Met Glu Asn Gly Ala Ala Thr Asn Gly Ala Ser Glu Lys Ser His Ser
1               5                   10                  15

Pro Ser Gln Thr Tyr Leu Ser Thr Arg Gly Asp Asp Tyr Gly Leu Ser
            20                  25                  30
```

```
Phe Glu Thr Val Val Leu Lys Gly Leu Ala Ala Asp Gly Gly Leu Phe
        35                  40                  45

Leu Pro Glu Glu Val Pro Ala Ala Thr Glu Trp Gln Ser Trp Lys Asp
 50                  55                  60

Leu Pro Tyr Thr Glu Leu Ala Val Lys Val Leu Ser Leu Tyr Ile Ser
 65                  70                  75                  80

Pro Ala Glu Val Pro Thr Glu Asp Leu Arg Ala Leu Val Glu Arg Ser
                85                  90                  95

Tyr Ser Thr Phe Arg Ser Lys Glu Val Val Pro Leu Val Lys Leu Glu
                100                 105                 110

Asp Asn Leu His Leu Glu Leu Phe His Gly Pro Asn Tyr Ser Phe
                115                 120                 125

Lys Asp Cys Ala Leu Gln Phe Leu Gly Asn Leu Xaa Glu Tyr Phe
    130                 135                 140
```

(2) INFORMATION FOR SEQ ID NO: 21:

(i) SEQUENCE CHARACTERISTICS:
        (A) LENGTH: 571 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: se1.06a03

(xi) SEQUENCE DESCRIPTION: SEQ ID NO: 21:

```
GGATGCAATG GTGCAGGCTG ATTCCACTGG AATGTTCATA TGTCCACACA CTGGGGTGGC      60
TCTGGCGGCG CTTATTAAGC TGAGGAATCG TGGGGTTATC GGTGCCGGTG AGAGGGTTG      120
GGTGGTGAGC ACTGCACATG GATTGAAGTT TGCACAGAGC AAGATTGATT ATCATTCTG      180
GCTCATTCCT GGAATGGGCC GCTATGCTAA CCCGCTGGTT TCGGTTAAGG CGGATTTTG      240
ATCGGTCATG GATGTTCTCA AGGATTCTTG CACAACAAGT CCCCCGACTT AACAAGTC       300
TGACGTTGCC AAGTAAGTTT TAGTTCGGGG TTTTTTCTGA TTAAAGATGT TTTTAAACA      360
GTTTGTGTNC ACTTTCGGTC GTTATTATGG ATTTGTAAGA TTGGGCCCAA GTATTCGAG      420
GTTTGATTTC AAACAACATG CTTCTGGTGA CGCAATGCAA ATTTCGGNGC ATAACATCA      480
TGTCGAAGAT GGATCNCGAC CGATGAAACT GTGTGGCAAG TAATGAGAAG AAAATAGGG      540
ACTTGTACAG AGATTTNAAA GNTTAATTTC N                                    571
```

(2) INFORMATION FOR SEQ ID NO: 22:

(i) SEQUENCE CHARACTERISTICS:
        (A) LENGTH: 104 amino acids
        (B) TYPE: amino acid
        (C) STRANDEDNESS: not relevant
        (D) TOPOLOGY: linear (ii) MOLECULE TYPE: peptide (vii) IMMEDIATE SOURCE:
        (B) CLONE: se1.06a03

(xi) SEQUENCE DESCRIPTION: SEQ ID NO: 22:

```
Asp Ala Met Val Gln Ala Asp Ser Thr Gly Met Phe Ile Cys Pro His
 1               5                  10                  15

Thr Gly Val Ala Leu Ala Ala Leu Ile Lys Leu Arg Asn Arg Gly Val
                20                  25                  30
```

```
Ile Gly Ala Gly Glu Arg Val Val Val Ser Thr Ala His Gly Leu
        35                  40                  45

Lys Phe Ala Gln Ser Lys Ile Asp Tyr His Ser Gly Leu Ile Pro Gly
        50                  55                  60

Met Gly Arg Tyr Ala Asn Pro Leu Val Ser Val Lys Ala Asp Phe Gly
65                  70                  75                  80

Ser Val Met Asp Val Leu Lys Asp Ser Cys Thr Thr Ser Pro Pro Thr
                85                  90                  95

Leu Thr Ser Leu Asp Val Ala Lys
            100
```

(2) INFORMATION FOR SEQ ID NO: 23:

(i) SEQUENCE CHARACTERISTICS:
        (A) LENGTH: 2191 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: sr1.pk0003.f6

(xi) SEQUENCE DESCRIPTION: SEQ ID NO: 23:

```
GCTTCCTCTT CTCTGTTTCA GTCTCTCCCT TTCTCTCTCC AAACCTCTAA ACCCTACGCG      60

CCTCCCAAAC CCGCCGCCCA CTTCGTTGTC CGCGCCCAAT CCCCCCTCAC TCAGAACAA      120

AACTCCTCCT CCAAGCATCG CCGCCCCGCC GACGAGAACA TCCGCGACGA GGCCCGCCG      180

ATCAATGCGC CCCACGACCA CCACCTCTTC TCGGCCAAGT ACGTCCCCTT CAACGCCGA      240

TCCTCCTCCT CCTCCTCCAC GGAGTCCTAC TCGCTCGACG AGATCGTCTA CCGCTCCCA      300

TCCGGCGGCC TCCTGGACGT CCAGCACGAC ATGGATGCCC TCAAGCGTTT CGACGGCGA      360

TACTGGCGCA ACCTCTTCGA CTCGCGCGTG GGCAAAACCA CCTGGCCTTA CGGCTCCGG      420

GTCTGGAGCA AAAAGAATG GGTCCTCCCC GAGATCCACG ACGACGATAT CGTCTCCGC      480

TTCGAGGGTA ACTCCAACCT CTTCTGGGCC GAGCGTTTCG GCAAACAGTT CCTCGGCAT      540

AACGATTTGT GGGTCAAACA CTGCGGAATC AGCCACACGG GCAGCTTCAA GGATCTCGG      600

ATGACCGTCC TCGTCAGCCA GGTCAATCGC TTGAGAAAAA TGAACCGCCC CGTCGTCGG      660

GTTGGTTGCG CCTCCACCGG TGACACATCG GCCGCTTTAT CCGCCTATTG CGCTTCCGC      720

GCCATTCCTT CCATTGTGTT TTTGCCTGCT AATAAAATCT CTCTTGCCCA ACTTGTTCA      780

CCTATTGCCA ATGGAGCCTT TGTGTTGAGT ATCGACACTG ATTTTGATGG TTGCATGCA      840

TTGATCAGAG AAGTCACTGC TGAATTGCCT ATTTATTTGG CTAACTCTCT CAACAGTTT      900

AAGTTGGAAG GCAGAAAAC TGCTGCTATT GAGATTCTGC AGCAGTTTGA TTGGCAGGT      960

CCTGATTGGG TCATTGTGCC TGGAAGCAAC CTTGGCAACA TTTATGCCTT TTACAAAG     1020

TTTAAGATGT TCAAGAGCT TGGGCTTGTG GATAAGATTC CAAGGCTTGT TTGTGCTC     1080

GCTGCCAATG CTGATCCTTT GTATTTGTAC TTTAAATCCG GGTGGAAGGA GTTTAAGC     1140

GTGAAGTCGA GCACTACATT TGCTTCTGCC ATTCAAATTG GTGATCCTGT TTCCATTG     1200

AGGGCGGTTC ACGCGCTAAA GAGTTGCGAT GGGATTGTGG AGGAGGCCAC GGAGGAGG     1260

TTGATGGATG CTACAGCGCA GGCGGATTCT ACTGGGATGT TTATTTGCCC CCACACCG     1320

GTTGCTTTAA CTGCATTGTT TAAGCTCAGG AACAGCGGGG TTATTAAGGC CACTGATA     1380

ACTGTGGTGG TTAGCACTGC TCATGGCTTG AAGTTCACTC AGTCCAAGAT TGATTACC     1440
```

```
TCTAAGGACA TCAAGGACAT GGCTTGCCGC TATGCTAACC CGCCCATGCA AGTGAAGG      1500

GACTTTGGCT CGGTTATGGA TGTTTTGAAG ACGTATTTGC AGAGTAAGGC TCATTAGG      1560

AGCATTGCAA GTTTTGCTCC TCCTGAGTTT GCTCATTATT TACTTACTTT TAGGCACT      1620

TGCTGTATTG TCTTTTCTAT GAGCTAGGTT TGAGTGTTGT AATAATTTGC TTGCTGCA      1680

ATGTATGCCG TCTAGTGTTC CATATTGGGC ATCATCCTTA GTATTTGTTG TAGATTTT      1740

TTGCTGAGCA TTTGATATAA TAGCTCAAGT AGGAAAATGA ATTGGGTACT ATGAGGAA      1800

CATATCATTG GCTTGTTATT ACTGGATTCC AGACCACCCC AAAAGAAAAT AATTCCAA      1860

AATATAATTA GAACAAATTT CGTCCTTGTT ATGCTGTTGG CATTAAGCTC AGTGTGGG      1920

TTACCAAGCA ACTCGAAATC AAGAGAAAAA AAAATTGACA GCAAAGGAGC TGCATTGT      1980

GACTGAGTCA CATCACTTCA TTGCTATGTC GTCATATTTC GTTGAATTAC GGGAAGGC      2040

CATGCACAGC AATATGCAGC GATTAACTGA AGCCACACCG CACACATTGA AGTAGTAG      2100

AATTTAGACA CTCCATCTTG TACTTTCTAC AAAAATGAAT TTTTCTTAGC CATTAAGT      2160

AATATTTTAT TCTAAAAAAA AAAAAAAAA A                                    2191
```

(2) INFORMATION FOR SEQ ID NO: 24:

(i) SEQUENCE CHARACTERISTICS:
        (A) LENGTH: 518 amino acids
        (B) TYPE: amino acid
        (C) STRANDEDNESS: not relevant
        (D) TOPOLOGY: linear (ii) MOLECULE TYPE: peptide (vii) IMMEDIATE SOURCE:
        (B) CLONE: sr1.pk0003.f6

(xi) SEQUENCE DESCRIPTION: SEQ ID NO: 24:

```
Ala Ser Ser Ser Leu Phe Gln Ser Leu Pro Phe Ser Leu Gln Thr Ser
  1               5                  10                  15

Lys Pro Tyr Ala Pro Pro Lys Pro Ala His Phe Val Val Arg Ala
             20                  25                  30

Gln Ser Pro Leu Thr Gln Asn Asn Asn Ser Ser Lys His Arg Arg
         35                  40                  45

Pro Ala Asp Glu Asn Ile Arg Asp Glu Ala Arg Arg Ile Asn Ala Pro
 50                  55                  60

His Asp His His Leu Phe Ser Ala Lys Tyr Val Pro Phe Asn Ala Asp
 65                  70                  75                  80

Ser Ser Ser Ser Ser Thr Glu Ser Tyr Ser Leu Asp Glu Ile Val
             85                  90                  95

Tyr Arg Ser Gln Ser Gly Gly Leu Leu Asp Val Gln His Asp Met Asp
            100                 105                 110

Ala Leu Lys Arg Phe Asp Gly Glu Tyr Trp Arg Asn Leu Phe Asp Ser
            115                 120                 125

Arg Val Gly Lys Thr Thr Trp Pro Tyr Gly Ser Gly Val Trp Ser Lys
        130                 135                 140

Lys Glu Trp Val Leu Pro Glu Ile His Asp Asp Ile Val Ser Ala
145                 150                 155                 160

Phe Glu Gly Asn Ser Asn Leu Phe Trp Ala Glu Arg Phe Gly Lys Gln
                165                 170                 175

Phe Leu Gly Met Asn Asp Leu Trp Val Lys His Cys Gly Ile Ser His
            180                 185                 190

Thr Gly Ser Phe Lys Asp Leu Gly Met Thr Val Leu Val Ser Gln Val
```

```
                195                 200                 205
Asn Arg Leu Arg Lys Met Asn Arg Pro Val Val Gly Val Gly Cys Ala
    210                 215                 220
Ser Thr Gly Asp Thr Ser Ala Ala Leu Ser Ala Tyr Cys Ala Ser Ala
225                 230                 235                 240
Ala Ile Pro Ser Ile Val Phe Leu Pro Ala Asn Lys Ile Ser Leu Ala
                245                 250                 255
Gln Leu Val Gln Pro Ile Ala Asn Gly Ala Phe Val Leu Ser Ile Asp
                260                 265                 270
Thr Asp Phe Asp Gly Cys Met Gln Leu Ile Arg Glu Val Thr Ala Glu
                275                 280                 285
Leu Pro Ile Tyr Leu Ala Asn Ser Leu Asn Ser Leu Lys Leu Glu Gly
    290                 295                 300
Gln Lys Thr Ala Ala Ile Glu Ile Leu Gln Gln Phe Asp Trp Gln Val
305                 310                 315                 320
Pro Asp Trp Val Ile Val Pro Gly Ser Asn Leu Gly Asn Ile Tyr Ala
                325                 330                 335
Phe Tyr Lys Gly Phe Lys Met Phe Gln Glu Leu Gly Leu Val Asp Lys
                340                 345                 350
Ile Pro Arg Leu Val Cys Ala Gln Ala Ala Asn Ala Asp Pro Leu Tyr
                355                 360                 365
Leu Tyr Phe Lys Ser Gly Trp Lys Glu Phe Lys Pro Val Lys Ser Ser
    370                 375                 380
Thr Thr Phe Ala Ser Ala Ile Gln Ile Gly Asp Pro Val Ser Ile Asp
385                 390                 395                 400
Arg Ala Val His Ala Leu Lys Ser Cys Asp Gly Ile Val Glu Glu Ala
                405                 410                 415
Thr Glu Glu Glu Leu Met Asp Ala Thr Ala Gln Ala Asp Ser Thr Gly
                420                 425                 430
Met Phe Ile Cys Pro His Thr Gly Val Ala Leu Thr Ala Leu Phe Lys
                435                 440                 445
Leu Arg Asn Ser Gly Val Ile Lys Ala Thr Asp Arg Thr Val Val Val
    450                 455                 460
Ser Thr Ala His Gly Leu Lys Phe Thr Gln Ser Lys Ile Asp Tyr His
465                 470                 475                 480
Ser Lys Asp Ile Lys Asp Met Ala Cys Arg Tyr Ala Asn Pro Pro Met
                485                 490                 495
Gln Val Lys Ala Asp Phe Gly Ser Val Met Asp Val Leu Lys Thr Tyr
                500                 505                 510
Leu Gln Ser Lys Ala His
        515

(2) INFORMATION FOR SEQ ID NO: 25:

(i) SEQUENCE CHARACTERISTICS:
        (A) LENGTH: 643 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: wr1.pk0085.h2

(xi) SEQUENCE DESCRIPTION: SEQ ID NO: 25:

GCTCATCCAG CCCATCGCCA ACGGCGCCAC GGTGCTCTCG CTTGACACGG ATTTCGACGG      60
```

-continued

```
ATGCATGCGG CTTATCAGGG AGGTGACAGC TGAGCTGCCC ATATACCTCG CAAACTCAC      120

CAACTCGCTT CCGGCTGGAG GGGCAGAAGA CTGCAGCCAT CCGAGATATT GCAACANTC      180

ATTGGCAGGT GCCCGGACTG GGTCACATCC CAAGGAGGCA ATCTGGGGGA ACATTTTAT      240

CTTTCCTACA AGGATTTNAA TTTCCGTGTC CTTNGCTAGT TGATTNCCTT CCNACTCCT      300

GTTANTNCAA NAGGCCGCCA ACGCAAACCC ACTGTACCCG TACTACAATC CTGGGGTGA      360

TGATTTCCAT CCACTTGNTT GCCGGGACAA TTTNCATCCN GCAACAATTT GGGGATTCC      420

TATCNATTAC CNTCGGTTTT TTCNCCCTNA AAGGACNNAT GATTNTCCNA GGAACTCCN      480

AGGNGGATCA AGGATCCAAA GGCTTTCTAC TCACTGGAAN TTGCTTCCCA ANACGGGGT      540

CACTNCCGCC CGTTAAACCC NTGACAAGTA TAATGGACAA CACNCCGGGG TNTATNACA      600

CGGCAANTTN AAANCAAGTT NATCATTAGA ACNGGAANTT NCC                       643
```

(2) INFORMATION FOR SEQ ID NO: 26:

(i) SEQUENCE CHARACTERISTICS:
        (A) LENGTH: 84 amino acids
        (B) TYPE: amino acid
        (C) STRANDEDNESS: not relevant
        (D) TOPOLOGY: linear (ii) MOLECULE TYPE: peptide (vii) IMMEDIATE SOURCE:
        (B) CLONE: wr1.pk0085.h2

(xi) SEQUENCE DESCRIPTION: SEQ ID NO: 26:

```
Leu Ile Gln Pro Ile Ala Asn Gly Ala Thr Val Leu Ser Leu Asp Thr
1               5                   10                  15

Asp Phe Asp Gly Cys Met Arg Leu Ile Arg Glu Val Thr Ala Glu Leu
                20                  25                  30

Pro Ile Tyr Leu Ala Asn Ser Leu Asn Ser Leu Xaa Leu Glu Gly Gln
            35                  40                  45

Lys Thr Ala Ala Ile Arg Asp Ile Ala Thr Xaa Asn Trp Gln Val Pro
        50                  55                  60

Gly Leu Gly His Ile Pro Arg Arg Gln Ser Xaa Thr Phe Tyr Ala Phe
65                  70                  75                  80

Leu Gln Gly Phe
```

(2) INFORMATION FOR SEQ ID NO: 27:

(i) SEQUENCE CHARACTERISTICS:
        (A) LENGTH: 525 amino acids
        (B) TYPE: amino acid
        (C) STRANDEDNESS: not relevant
        (D) TOPOLOGY: linear (ii) MOLECULE TYPE: peptide (vi) ORIGINAL SOURCE:
        (A) ORGANISM: Arabidopsis thaliana (xi) SEQUENCE DESCRIPTION: SEQ ID NO: 27:

```
Leu Ser Ser Cys Leu Phe Asn Ala Ser Val Ser Ser Leu Asn Pro Lys
1               5                   10                  15

Gln Asp Pro Ile Arg Arg His Arg Ser Thr Ser Leu Leu Arg His Arg
                20                  25                  30

Pro Val Val Ile Ser Cys Thr Ala Asp Gly Asn Asn Ile Lys Ala Pro
            35                  40                  45
```

-continued

```
Ile Glu Thr Ala Val Lys Pro Pro His Arg Thr Glu Asp Asn Ile Arg
 50                  55                  60

Asp Glu Ala Arg Arg Asn Arg Ser Asn Ala Val Asn Pro Phe Ser Ala
 65                  70                  75                  80

Lys Tyr Val Pro Phe Asn Ala Ala Pro Gly Ser Thr Glu Ser Tyr Ser
                 85                  90                  95

Leu Asp Glu Ile Val Tyr Arg Ser Arg Ser Gly Gly Leu Leu Asp Val
            100                 105                 110

Glu His Asp Met Glu Ala Leu Lys Arg Phe Asp Gly Ala Tyr Trp Arg
        115                 120                 125

Asp Leu Phe Asp Ser Arg Val Gly Lys Ser Thr Trp Pro Tyr Gly Ser
130                 135                 140

Gly Val Trp Ser Lys Lys Glu Trp Val Leu Pro Glu Ile Asp Asp Asp
145                 150                 155                 160

Asp Ile Val Ser Ala Phe Glu Gly Asn Ser Asn Leu Phe Trp Ala Glu
                165                 170                 175

Arg Phe Gly Lys Gln Phe Leu Gly Met Asn Asp Leu Trp Val Lys His
            180                 185                 190

Cys Gly Ile Ser His Thr Gly Ser Phe Lys Asp Leu Gly Met Thr Val
        195                 200                 205

Leu Val Ser Gln Val Asn Arg Leu Arg Lys Met Lys Arg Pro Val Val
210                 215                 220

Gly Val Gly Cys Ala Ser Thr Gly Asp Thr Ser Ala Ala Leu Ser Ala
225                 230                 235                 240

Tyr Cys Ala Ser Ala Gly Ile Pro Ser Ile Val Phe Leu Pro Ala Asn
                245                 250                 255

Lys Ile Ser Met Ala Gln Leu Val Gln Pro Ile Ala Asn Gly Ala Phe
            260                 265                 270

Val Leu Ser Ile Asp Thr Asp Phe Asp Gly Cys Met Lys Leu Ile Arg
        275                 280                 285

Glu Ile Thr Ala Glu Leu Pro Ile Tyr Leu Ala Asn Ser Leu Asn Ser
290                 295                 300

Leu Arg Leu Glu Gly Gln Lys Thr Ala Ala Ile Glu Ile Leu Gln Gln
305                 310                 315                 320

Phe Asp Trp Gln Val Pro Asp Trp Val Ile Val Pro Gly Gly Asn Leu
                325                 330                 335

Gly Asn Ile Tyr Ala Phe Tyr Lys Gly Phe Lys Met Cys Gln Glu Leu
            340                 345                 350

Gly Leu Val Asp Arg Ile Pro Arg Met Val Cys Ala Gln Ala Ala Asn
        355                 360                 365

Ala Asn Pro Leu Tyr Leu His Tyr Lys Ser Gly Trp Lys Asp Phe Lys
370                 375                 380

Pro Met Thr Ala Ser Thr Thr Phe Ala Ser Ala Ile Gln Ile Gly Asp
385                 390                 395                 400

Pro Val Ser Ile Asp Arg Ala Val Tyr Ala Leu Lys Lys Cys Asn Gly
                405                 410                 415

Ile Val Glu Glu Ala Thr Glu Glu Leu Met Asp Ala Met Ala Gln
            420                 425                 430

Ala Asp Ser Thr Gly Met Phe Ile Cys Pro His Thr Gly Val Ala Leu
        435                 440                 445

Thr Ala Leu Phe Lys Leu Arg Asn Gln Gly Val Ile Ala Pro Thr Asp
450                 455                 460

Arg Thr Val Val Val Ser Thr Ala His Gly Leu Lys Phe Thr Gln Ser
```

```
                465                  470                  475                  480
           Lys Ile Asp Tyr His Ser Asn Ala Ile Pro Asp Met Ala Cys Arg Phe
                                485                  490                  495

Ser Asn Pro Pro Val Asp Val Lys Ala Asp Phe Gly Ala Val Met Asp
                       500                  505                  510

Val Leu Lys Ser Tyr Leu Gly Ser Asn Thr Leu Thr Ser
                       515                  520                  525
```

(2) INFORMATION FOR SEQ ID NO: 28:

(i) SEQUENCE CHARACTERISTICS:
        (A) LENGTH: 1478 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: cen1.pk0064.f4

(xi) SEQUENCE DESCRIPTION: SEQ ID NO: 28:

```
CAACAGTGGT CCTTGAGGGG GACTCATATG ATGAAGCTCA GTCATATGCA AAATTGCGTT      60
GCCAGCAGGA AGGCCGCACA TTTGTACCTC CTTTTGACCA TCCTGATGTC ATCACTGGA      120
AAGGAACTAT CGGCATGGAA ATTGTTAGGC AGCTGCAAGG TCCACTGCAT GCAATATTT      180
TACCTGTTGG AGGTGGTGGA TTAATTGCTG GAATTGCTGC CTATGTAAAA CGGGTTCGC      240
CAGAGGTGAA AATAATTGGA GTGGAACCCT CAGATGCAAA TGCAATGGCA TTATCCTTG      300
GTCATGGTAA GAGGGTCATG TTGGAGCATG TTGGTGGGTT TGCTGATGGT GTAGCTGTC      360
AAGCTGTTGG GGAAGAAACA TTTCGCCTGT GCAGAGAGCT AGTAGATGGC ATTGTTATG      420
TCAGTCGAGA TGCTATTTGT GCTTCAATAA AGGATATGTT TGAGGAGAAA AGAAGTATC      480
TTGAACCTGC TGGTGCCCTT GCATTGGCTG GGCTGAAGC CTACTGCAAA TACTATAAC       540
TGAAAGGAGA AACTGTGGTT GCAATAACTA GTGGGGCAAA TATGAACTTT GATCGACTT      600
GACTAGTAAC CGAGCTAGCT GATGTTGGCC GAAAACGGGA AGCAGTGTTA GCTACATTT      660
TGCCAGAGCG GCAGGGAAGC TTCAAAAAAT TCACAGAATT GGTTGGCAGG ATGAATATT      720
CTGAATTCAA ATACAGATAC GATTCTAATG CAAAAGATGC CCTTGTTCTT TACAGTGTT      780
GCATCTACAC TGACAATGAG CTTGGAGCAA TGATGGATCG CATGGAATCT GCGAAACTG      840
GGACTGTTAA CCTTACTGAC AATGATTTGG CAAAGGACCA CCTTAGATAC TTTATTGGA      900
GAAGATCAGA ATAAAAGAT GAACTGGTTT ACCGGTTCAT TTTCCCGGAA AGGCCTGGG       960
CCCTTATGAA ATTTTTGGAC ACGTTTAGTC CTCGTTGGAA CATCAGCCTT TTCCATTA       1020
GTGCACAGGG TGAAGCTGGA GCAAATGTAT TAGTTGGTAT ACAAGTGCCG CCAGCAGA       1080
TTGATGAATT CAAGAGTCAT GCCAACAATC TTGGGTACGA GTACATGTCA GAGCACAA       1140
ATGAGATATA CCGGTTGCTG TTGCGTGACC CAAAGGTCTA ATGTATATGC CTTTGCTC       1200
ATAATAAGTT GGTGACACTT TTCAAGGAAG ATTTTGCTCC AAGGTAGAAG TTGCGAGT       1260
CTTCAAGTTG AAATGAAGCC ATCACCAAAT GTAGCTTCGG TGTGCCATCT GTTTACTC       1320
TTAGATCATG TAGTGTATCA GTTGTGTATC TTTGTTGTTG TGCTTCGTGA TCTCAATT       1380
TTGCTTTGTG CACCTAGAGG TTGTCAAATA ATGATAACCG ATATGTTATC TAAATATC      1440
ATAATGATTA TGTGATTGTG ATTAAAAAGG GGGGGCCC                             1478
```

(2) INFORMATION FOR SEQ ID NO: 29:

(i) SEQUENCE CHARACTERISTICS:
    (A) LENGTH: 392 amino acids
    (B) TYPE: amino acid
    (C) STRANDEDNESS: not relevant
    (D) TOPOLOGY: linear (ii) MOLECULE TYPE: peptide (vii) IMMEDIATE SOURCE:
    (B) CLONE: cen1.pk0064.f4

(xi) SEQUENCE DESCRIPTION: SEQ ID NO: 29:

```
Thr Val Val Leu Glu Gly Asp Ser Tyr Asp Glu Ala Gln Ser Tyr Ala
1               5                   10                  15

Lys Leu Arg Cys Gln Gln Glu Gly Arg Thr Phe Val Pro Pro Phe Asp
            20                  25                  30

His Pro Asp Val Ile Thr Gly Gln Gly Thr Ile Gly Met Glu Ile Val
                35                  40                  45

Arg Gln Leu Gln Gly Pro Leu His Ala Ile Phe Val Pro Val Gly Gly
        50                  55                  60

Gly Gly Leu Ile Ala Gly Ile Ala Ala Tyr Val Lys Arg Val Arg Pro
65                  70                  75                  80

Glu Val Lys Ile Ile Gly Val Glu Pro Ser Asp Ala Asn Ala Met Ala
                85                  90                  95

Leu Ser Leu Cys His Gly Lys Arg Val Met Leu Glu His Val Gly Gly
                100                 105                 110

Phe Ala Asp Gly Val Ala Val Lys Ala Val Gly Glu Glu Thr Phe Arg
            115                 120                 125

Leu Cys Arg Glu Leu Val Asp Gly Ile Val Met Val Ser Arg Asp Ala
        130                 135                 140

Ile Cys Ala Ser Ile Lys Asp Met Phe Glu Glu Lys Arg Ser Ile Leu
145                 150                 155                 160

Glu Pro Ala Gly Ala Leu Ala Leu Ala Gly Ala Glu Ala Tyr Cys Lys
                165                 170                 175

Tyr Tyr Asn Leu Lys Gly Glu Thr Val Val Ala Ile Thr Ser Gly Ala
            180                 185                 190

Asn Met Asn Phe Asp Arg Leu Arg Leu Val Thr Glu Leu Ala Asp Val
        195                 200                 205

Gly Arg Lys Arg Glu Ala Val Leu Ala Thr Phe Leu Pro Glu Arg Gln
210                 215                 220

Gly Ser Phe Lys Lys Phe Thr Glu Leu Val Gly Arg Met Asn Ile Thr
225                 230                 235                 240

Glu Phe Lys Tyr Arg Tyr Asp Ser Asn Ala Lys Asp Ala Leu Val Leu
            245                 250                 255

Tyr Ser Val Gly Ile Tyr Thr Asp Asn Glu Leu Gly Ala Met Met Asp
                260                 265                 270

Arg Met Glu Ser Ala Lys Leu Arg Thr Val Asn Leu Thr Asp Asn Asp
        275                 280                 285

Leu Ala Lys Asp His Leu Arg Tyr Phe Ile Gly Arg Ser Glu Ile
290                 295                 300

Lys Asp Glu Leu Val Tyr Arg Phe Ile Phe Pro Glu Arg Pro Gly Ala
305                 310                 315                 320

Leu Met Lys Phe Leu Asp Thr Phe Ser Pro Arg Trp Asn Ile Ser Leu
            325                 330                 335

Phe His Tyr Arg Ala Gln Gly Glu Ala Gly Ala Asn Val Leu Val Gly
                340                 345                 350
```

```
Ile Gln Val Pro Pro Ala Glu Phe Asp Glu Phe Lys Ser His Ala Asn
        355                 360                 365

Asn Leu Gly Tyr Glu Tyr Met Ser Glu His Asn Asn Glu Ile Tyr Arg
        370                 375                 380

Leu Leu Leu Arg Asp Pro Lys Val
385                 390

(2) INFORMATION FOR SEQ ID NO: 30:

(i) SEQUENCE CHARACTERISTICS:
        (A) LENGTH: 728 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: sfl1.pk0055.h7

(xi) SEQUENCE DESCRIPTION: SEQ ID NO: 30:
```

| | | | | | |
|---|---|---|---|---|---|
| AAAATATTGT | AGCAATAACC | AGTGGAGCAA | ACATGAATTT | TGATAAACTT | CGGGTTGTAA | 60 |
| CTGAACTTGC | TAATGTTGGT | CGTAAACAAG | AGGCTGTGCT | GGCAACTGTT | ATGGCAGAG | 120 |
| AGCCTGGCAG | TTTCAAACAA | TTTTGTGAAT | TGGTGGGGCA | GATGAACATA | ACAGAATTC | 180 |
| AATACAGATA | TAACTCAAAT | GAGAAGGCAG | TTGTCCTTTA | CAGTGTTGGG | GTTCACACA | 240 |
| TCTCCGAACT | AAGAGCAATG | CAGGAGAGGA | TGGAATCTTC | TCAGCTCAAA | ACTTACAAT | 300 |
| TCACAGAAAG | TGACTTGGTG | AAAGACCACT | TGCGTTACTT | GATGGGAGGC | CGATCAAAC | 360 |
| TTCAGAATGA | GGTCTTTGTC | GTCTCACCTT | TCCAAGAAAG | ACTGGTGCTT | TGATGAAAT | 420 |
| TTTGGACCCT | TCAGTCCACG | TTGGGATATT | AGTTTATCCA | TTACCGAGGG | GAGGTGAAA | 480 |
| TGGAGCAAAC | TGCTAGTTGG | NTACAGGTAC | CAAAATGAGA | TAGATGAGTC | CATGATCGT | 540 |
| CTAACAAACT | GGATATGATT | ATAAGTGGNA | ATATGTGATG | NCTCAGCTCA | ATCNCGATG | 600 |
| GGNTTAAGCA | CTGCATATGG | GNATTAGGGG | NAGNTACANT | TAAATTCACG | GCCTCAAGN | 660 |
| AAGCATANTN | TAGGAACTAG | CTTTACAGGG | GGCTACNANT | TAACCGNGTA | TTTTTTTTG | 720 |
| GATGANNG | | | | | | 728 |

```
(2) INFORMATION FOR SEQ ID NO: 31:

(i) SEQUENCE CHARACTERISTICS:
        (A) LENGTH: 152 amino acids
        (B) TYPE: amino acid
        (C) STRANDEDNESS: not relevant
        (D) TOPOLOGY: linear (ii) MOLECULE TYPE: peptide (vii) IMMEDIATE SOURCE:
        (B) CLONE: sfl1.pk0055.h7

(xi) SEQUENCE DESCRIPTION: SEQ ID NO: 31:

Asn Ile Val Ala Ile Thr Ser Gly Ala Asn Met Asn Phe Asp Lys Leu
1               5                   10                  15

Arg Val Val Thr Glu Leu Ala Asn Val Gly Arg Lys Gln Glu Ala Val
            20                  25                  30

Leu Ala Thr Val Met Ala Glu Glu Pro Gly Ser Phe Lys Gln Phe Cys
        35                  40                  45

Glu Leu Val Gly Gln Met Asn Ile Thr Glu Phe Lys Tyr Arg Tyr Asn
    50                  55                  60
```

```
Ser Asn Glu Lys Ala Val Val Leu Tyr Ser Val Gly Val His Thr Ile
 65                  70                  75                  80

Ser Glu Leu Arg Ala Met Gln Glu Arg Met Glu Ser Ser Gln Leu Lys
                 85                  90                  95

Thr Tyr Asn Leu Thr Glu Ser Asp Leu Val Lys Asp His Leu Arg Tyr
            100                 105                 110

Leu Met Gly Gly Arg Ser Asn Val Gln Asn Glu Val Phe Val Val Ser
            115                 120                 125

Pro Xaa Pro Arg Lys Thr Gly Ala Leu Met Lys Phe Leu Asp Xaa Phe
    130                 135                 140

Ser Pro Arg Trp Asp Ile Ser Leu
145                 150
```

(2) INFORMATION FOR SEQ ID NO: 32:

(i) SEQUENCE CHARACTERISTICS:
        (A) LENGTH: 572 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: sre.pk0044.f3

(xi) SEQUENCE DESCRIPTION: SEQ ID NO: 32:

```
AAAGACCTGG TGCTTTGATG AAATTTTTGG ACCCCTTCAG TCCACGTTGG AATATCAGTT      60

TATTCCATTA CCGAGGGGAG GGTGAAACTG GAGCAAATGT GCTAGTTGGA ATACAGGTA     120

CCAAAAGTGA GATGGATGAG TTCCACGATC GTGCCAACAA ACTTGGATAT GATTATAAA     180

TGGTGAATAA TGATGATGAC TTCCAGCTTC TAATGCACTG ATGATGGTTT TAGGCACTT     240

CCATTATTGT GTATTTTAGT CAACAAGTTT GCCATATTTA ATATTCCAC GGTCGTTTC      300

AAAAGTTGGA TGGGGAAAAA AGGTGGAAAG GAAGTGGCCT TCAGACATGT CATTAGTTG     360

TTAGAGGAAC AACTAGTTCT TTTTACCTAA TGCGGCGTCT TATTACATTT TTTATAATC     420

GTAATTTATG TTTTTTTGTT GTTGTTAACA TTGGAATCTT ATAATGTTGT TGCCTGGTC     480

TTTGTGTCTG TAATATAAGT GTCTTCAAAA GGTTGTTTGC TAAATTTCAG CAGCCTAAA     540

AAAAAAAAAA AAAAAAAAAA AAAAAAAAAA AA                                 572
```

(2) INFORMATION FOR SEQ ID NO: 33:

(i) SEQUENCE CHARACTERISTICS:
        (A) LENGTH: 72 amino acids
        (B) TYPE: amino acid
        (C) STRANDEDNESS: not relevant
        (D) TOPOLOGY: linear (ii) MOLECULE TYPE: peptide (vii) IMMEDIATE SOURCE:
        (B) CLONE: sre.pk0044.f3

(xi) SEQUENCE DESCRIPTION: SEQ ID NO: 33:

```
Arg Pro Gly Ala Leu Met Lys Phe Leu Asp Pro Phe Ser Pro Arg Trp
  1               5                  10                  15

Asn Ile Ser Leu Phe His Tyr Arg Gly Glu Gly Glu Thr Gly Ala Asn
             20                  25                  30

Val Leu Val Gly Ile Gln Val Pro Lys Ser Glu Met Asp Glu Phe His
             35                  40                  45
```

-continued

```
Asp Arg Ala Asn Lys Leu Gly Tyr Asp Tyr Lys Val Val Asn Asn Asp
    50                  55                  60

Asp Asp Phe Gln Leu Leu Met His
65                  70
```

(2) INFORMATION FOR SEQ ID NO: 34:

(i) SEQUENCE CHARACTERISTICS:
(A) LENGTH: 507 amino acids
(B) TYPE: amino acid
(C) STRANDEDNESS: not relevant
(D) TOPOLOGY: linear (ii) MOLECULE TYPE: peptide (vi) ORIGINAL SOURCE:
(A) ORGANISM: Burkholderia capacia (xi) SEQUENCE DESCRIPTION: SEQ ID NO: 34:

```
Met Ala Ser His Asp Tyr Leu Lys Lys Ile Leu Thr Ala Arg Val Tyr
1               5                   10                  15

Asp Val Ala Phe Glu Thr Glu Leu Glu Pro Ala Arg Asn Leu Ser Ala
            20                  25                  30

Arg Leu Arg Asn Pro Val Tyr Leu Lys Arg Glu Asp Asn Gln Pro Val
        35                  40                  45

Phe Ser Phe Lys Leu Arg Gly Ala Tyr Asn Lys Met Ala His Ile Pro
    50                  55                  60

Ala Asp Ala Leu Ala Arg Gly Val Ile Thr Ala Ser Ala Gly Asn His
65                  70                  75                  80

Ala Gln Gly Val Ala Phe Ser Ala Ala Arg Met Gly Val Lys Ala Val
                85                  90                  95

Ile Val Val Pro Val Thr Thr Pro Gln Val Lys Val Asp Ala Val Arg
            100                 105                 110

Ala His Gly Gly Pro Gly Val Glu Val Ile Gln Ala Gly Glu Ser Tyr
        115                 120                 125

Ser Asp Ala Tyr Ala His Ala Leu Lys Val Gln Glu Glu Arg Gly Leu
    130                 135                 140

Thr Phe Val His Pro Phe Asp Asp Pro Tyr Val Ile Ala Gly Gln Gly
145                 150                 155                 160

Thr Ile Ala Met Glu Ile Leu Arg Gln His Gln Gly Pro Ile His Ala
                165                 170                 175

Ile Phe Val Pro Ile Gly Gly Gly Gly Leu Ala Ala Gly Val Ala Ala
            180                 185                 190

Tyr Val Lys Ala Val Arg Pro Glu Ile Lys Val Ile Gly Val Gln Ala
        195                 200                 205

Glu Asp Ser Cys Ala Met Ala Gln Ser Leu Gln Ala Gly Lys Arg Val
    210                 215                 220

Glu Leu Ala Glu Val Gly Leu Phe Ala Asp Gly Thr Ala Val Lys Leu
225                 230                 235                 240

Val Gly Glu Glu Thr Phe Arg Leu Cys Lys Glu Tyr Leu Asp Gly Val
                245                 250                 255

Val Thr Val Asp Thr Asp Ala Leu Cys Ala Ala Ile Lys Asp Val Phe
            260                 265                 270

Gln Asp Thr Arg Ser Val Leu Glu Pro Ser Gly Ala Leu Ala Val Ala
        275                 280                 285

Gly Ala Lys Leu Tyr Ala Glu Arg Glu Gly Ile Glu Asn Gln Thr Leu
    290                 295                 300
```

```
Val Ala Val Thr Ser Gly Ala Asn Met Asn Phe Asp Arg Met Arg Phe
305                 310                 315                 320

Val Ala Glu Arg Ala Glu Val Gly Glu Ala Arg Glu Ala Val Phe Ala
                325                 330                 335

Val Thr Ile Pro Glu Glu Arg Gly Ser Phe Lys Arg Phe Cys Ser Leu
            340                 345                 350

Val Gly Asp Arg Asn Val Thr Glu Phe Asn Tyr Arg Ile Ala Asp Ala
        355                 360                 365

Gln Ser Ala His Ile Phe Val Gly Val Gln Ile Arg Arg Arg Gly Glu
370                 375                 380

Ser Ala Asp Ile Ala Ala Asn Phe Glu Ser His Gly Phe Lys Thr Ala
385                 390                 395                 400

Asp Leu Thr His Asp Glu Leu Ser Lys Glu His Ile Arg Tyr Met Val
                405                 410                 415

Gly Gly Arg Ser Pro Leu Ala Leu Asp Glu Arg Leu Phe Arg Phe Glu
            420                 425                 430

Phe Pro Glu Arg Pro Gly Ala Leu Met Lys Phe Leu Ser Ser Met Ala
        435                 440                 445

Pro Asp Trp Asn Ile Ser Leu Phe His Tyr Arg Asn Gln Gly Ala Asp
450                 455                 460

Tyr Ser Ser Ile Leu Val Gly Leu Gln Val Pro Gln Ala Asp His Ala
465                 470                 475                 480

Glu Phe Glu Arg Phe Leu Ala Ala Leu Gly Tyr Pro Tyr Val Glu Glu
                485                 490                 495

Ser Ala Asn Pro Ala Tyr Arg Leu Phe Leu Ser
            500                 505
```

(2) INFORMATION FOR SEQ ID NO: 35:

(i) SEQUENCE CHARACTERISTICS:
        (A) LENGTH: 1582 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: cc3.mn0002d2

(xi) SEQUENCE DESCRIPTION: SEQ ID NO: 35:

```
ACGAGACGAG TCCCCTCCCC CCACCTCGCC TCACCCAACC GGAACGAACA AGTTACCATC        60

TCATCCCAAC CCCGCCTCGA CCGGATCTCG TCGGACTCGG ATCCGCCCGA CCACCCCGC        120

CCGCCGCAGA TCAAAGAAGA TGGCAGCTCT CGACACCTTC CTCTTCACCT CGGAGTCTG        180

GAACGAGGGA CACCCTGACA AGCTCTGCGA CCAGGTCTCA GATGCCGTTC TTGACGCTT        240

CCTTGCTGAG GACCCTGACA GCAAGGTTGC TTGTGAGACC TGCACCAAGA CCAACATGG        300

CATGGTCTTT GGTGAGATCA CCACCAAGGC CAATGTCGAC TACGAAGAGA TTGTCAGGG        360

GACCTGCCGC AACATTGGTT TTGTGTCAAA CGATGTCGGG CTTGACGCTG ACCACTGCA        420

GGTGCTCGTG AACATTGAGC AGCAGTCCCC TGATATTGCT CAGGGTGTGC ATGGCCACT        480

CACCAAGCGC CCCGAGGAGA TTGGAGCTGG TGACCAGGGA CACATGTTCG GTATGCGCA        540

CGATGAGACC CCTGAGTTGA TGCCCCTCAG CCATGTCCTT GCCACCAAGC TAGGTGCTC        600

TCTCACCGAG GTCCGCAAGA ACGGAACCTG CCCCTGGCTC AGGCCTGATG GGAAGACCC        660

GGTGACAGTC GAGTACCGCA ATGAGGGTGG TGCCATGGTC CCCATCCGTG TCCACACCG        720
```

```
CCTCATCTCC ACCCAGCACG ACGAGACAGT GACCAATGAT GAGATCGCTG CTGACCTGA      780

GGAGCATGTC ATCAAGCCTA TCATCCCTGA GCAGTACCTT GACGAGAAGA CCATCTTCC      840

CCTTAACCCA TCCGGCCGCT TTGTCATTGG TGGACCTCAC GGCGATGCTG GCCTCACTG      900

CCGCAAGATC ATCATTGACA CCTACGGTGG CTGGGGAGCC CATGGCGGTG GCGCTTTCT      960

CGGCAAGGAC CCAACCAAGG TTGACCGCAG CGGAGCCTAT GTCGCGAGGC AGGCTGCC     1020

GAGCATCGTC GCCAGCGGCC TTGCTCGCCG CGCCATCGTC CAGGTGTCCT ACGCCATC     1080

CGTGCCCGAG CCTCTCTCCG TGTTTGTCGA CACGTACGGC ACCGGCGCGA TCCCCGAC     1140

GGAGATCCTC AAGATTGTCA AGGAGAACTT CGATTTCAGG CCTGGCATGA TTATCATC     1200

CCTTGACCTC AAGAAAGGCG GCAACGGGCG CTACCTCAAG ACGGCAGCCT ACGGCCAC     1260

CGGAAGGGAC GACCCTGACT TCACCTGGGA GGTGGTGAAG CCACTCAAGT CGGAGAAA     1320

TTCTGCCTAA GGCGGCCTTT TTTTCAGTAA GAAGCTTTTG GTGGTCTGCT GTGCTTAA     1380

ATGCTTTTAT ATGGCTTCTA CATGTTGTGG TTCTTTCTTG ATCTGCACCG CGCTTATC     1440

TTGTGTTGTA CTGCCCTAAT AAGTGGTGCT TATGAGGACT GTTTCTGGTT TTGCTGCT     1500

TGTTGTAATG CTTTGAAACA ATGAAAGAAG CTACAGGCCA CAGCTATTTT GAGAAGTA     1560

GGAACCTCGT GCCGTTTTGA TT                                              1582

(2) INFORMATION FOR SEQ ID NO: 36:

(i) SEQUENCE CHARACTERISTICS:
        (A) LENGTH: 396 amino acids
        (B) TYPE: amino acid
        (C) STRANDEDNESS: not relevant
        (D) TOPOLOGY: linear (ii) MOLECULE TYPE: peptide (vii) IMMEDIATE SOURCE:
        (B) CLONE: cc3.mn0002.d2

(xi) SEQUENCE DESCRIPTION: SEQ ID NO: 36:

Met Ala Ala Leu Asp Thr Phe Leu Phe Thr Ser Glu Ser Val Asn Glu
1               5                   10                  15

Gly His Pro Asp Lys Leu Cys Asp Gln Val Ser Asp Ala Val Leu Asp
                20                  25                  30

Ala Cys Leu Ala Glu Asp Pro Asp Ser Lys Val Ala Cys Glu Thr Cys
            35                  40                  45

Thr Lys Thr Asn Met Val Met Val Phe Gly Glu Ile Thr Thr Lys Ala
        50                  55                  60

Asn Val Asp Tyr Glu Lys Ile Val Arg Glu Thr Cys Arg Asn Ile Gly
65                  70                  75                  80

Phe Val Ser Asn Asp Val Gly Leu Asp Ala Asp His Cys Lys Val Leu
                85                  90                  95

Val Asn Ile Glu Gln Gln Ser Pro Asp Ile Ala Gln Gly Val His Gly
            100                 105                 110

His Phe Thr Lys Arg Pro Glu Glu Ile Gly Ala Gly Asp Gln Gly His
        115                 120                 125

Met Phe Gly Tyr Ala Thr Asp Glu Thr Pro Glu Leu Met Pro Leu Ser
    130                 135                 140

His Val Leu Ala Thr Lys Leu Gly Ala Arg Leu Thr Glu Val Arg Lys
145                 150                 155                 160

Asn Gly Thr Cys Pro Trp Leu Arg Pro Asp Gly Lys Thr Gln Val Thr
                165                 170                 175
```

```
Val Glu Tyr Arg Asn Glu Gly Gly Ala Met Val Pro Ile Arg Val His
                180                 185                 190

Thr Val Leu Ile Ser Thr Gln His Asp Glu Thr Val Thr Asn Asp Glu
            195                 200                 205

Ile Ala Ala Asp Leu Lys Glu His Val Ile Lys Pro Ile Pro Glu
        210                 215                 220

Gln Tyr Leu Asp Glu Lys Thr Ile Phe His Leu Asn Pro Ser Gly Arg
225                 230                 235                 240

Phe Val Ile Gly Gly Pro His Gly Asp Ala Gly Leu Thr Gly Arg Lys
                245                 250                 255

Ile Ile Ile Asp Thr Tyr Gly Gly Trp Gly Ala His Gly Gly Gly Ala
                260                 265                 270

Phe Ser Gly Lys Asp Pro Thr Lys Val Asp Arg Ser Gly Ala Tyr Val
            275                 280                 285

Ala Arg Gln Ala Ala Lys Ser Ile Val Ala Ser Gly Leu Ala Arg Arg
        290                 295                 300

Ala Ile Val Gln Val Ser Tyr Ala Ile Gly Val Pro Glu Pro Leu Ser
305                 310                 315                 320

Val Phe Val Asp Thr Tyr Gly Thr Gly Ala Ile Pro Asp Lys Glu Ile
                325                 330                 335

Leu Lys Ile Val Lys Glu Asn Phe Asp Phe Arg Pro Gly Met Ile Ile
            340                 345                 350

Ile Asn Leu Asp Leu Lys Lys Gly Gly Asn Gly Arg Tyr Leu Lys Thr
        355                 360                 365

Ala Ala Tyr Gly His Phe Gly Arg Asp Asp Pro Asp Phe Thr Trp Glu
        370                 375                 380

Val Val Lys Pro Leu Lys Ser Glu Lys Pro Ser Ala
385                 390                 395

(2) INFORMATION FOR SEQ ID NO: 37:

(i) SEQUENCE CHARACTERISTICS:
        (A) LENGTH: 2183 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Oryza sativa (xi) SEQUENCE DESCRIPTION: SEQ ID NO: 37:

GAATTCTTAT AAATGAACGG AAAATGGAAA AAAAAATTGA TTGGTGCCAC TTCAAAGTTA      60

AATATGCCAA GACGAATTGA TATGTTTCTG CTGTTGTTTT ATGCTCTTGA TTAGTTGAT     120

CGCATGTTCA ATGATTTATG ATGTTTGTCT TTGTGGAAAG ATTACATGTA AAGAGTATA     180

TAGAACCCCT AAAAGCTAGC CAGCGATTTC GCTCTTTTTT TCCAGGTCTC CATGATATG     240

TTACCCCTAA AAGTGGTATA TTTATGTGAT AGTTACAATA CATAGTGGAC CACGATTGA     300

TATGCGTTTA TGCTGATTCC GGCAGAAAAT TGTTAGATTC CTTGTGCTCT ATACCTGCT     360

GTTGCGCTTG TAGAGAATAT TACAAATACC TAACACTTGC CCAAGGAACT TAGGAACTT     420

GTCAACTCTT TGTAGGGACA ACTATTTTAG CCCAAAATTG TGGTCTTGTC AGGTGCCAA     480

AAAACAGCAT CTTGGCGTAC ATAAGCTATA TAGAGGATTA AAAGGAATGT TTGTTCCT     540

GCTACTGTTT TTTAACCTG TTACTCAGG ACAAATTTTG TTGCATAAAC CATTTGTTC     600
```

```
AGGGATCAGT ATTGTCCTCT CAGTGTGTTA TGTAAGCATT TCCAGAAATC AATTGTCGC      660

ATCAGCTTCC CTCACATTAG CTATCACTTA TACCCCTTTT TTTCTCATAG GCTCACCAT      720

TCCATTTTAT TCATGATATT TCTTTGTCTA AAGTATGTGA AATACCATTT TATGCAGAT      780

GGAGAAGATG GCCGCACTTG ATACCTTCCT CTTTACCTCG GAGTCTGTGA ACGAGGGCC      840

CCCTGACAAG CTCTGCGACC AAGTCTCAGA TGCTGTGCTT GATGCCTGCC TCGCCGAGG      900

CCCTGACAGC AAGGTCGCTT GTGAGACCTG CACCAAGACA AACATGGTCA TGGTCTTTG      960

TGAGATCACC ACCAAGGCTA ACGTTGACTA TGAGAAGATT GTCAGGGAGA CATGCCGT     1020

CATCGGTTTT GTGTCAGCTG ATGTCGGTCT CGATGCTGAC CACTGCAAGG TGCTTGTG     1080

CATCGAGCAG CAGTCCCCTG ACATTGCACA GGGTGTGCAC GGGCACTTCA CCAAGCGC     1140

TGAGGAGATT GGTGCTGGTG ACCAGGGACA CATGTTTGGA TATGCAACTG ATGAGACC     1200

TGAGTTGATG CCCCTCAGCC ATGTCCTTGC TACCAAGCTT GGCGCTCGTC TTACGGAG     1260

TCGCAAGAAT GGGACCTGCG CATGGCTCAG GCCTGACGGG AAGACCCAAG TGACTGTT     1320

GTACCGCAAT GAGAGCGGTG CCAGGGTCCC TGTCCGTGTC CACACCGTCC TCATCTCT     1380

CCAGCATGAT GAGACAGTCA CCAACGATGA GATTGCTGCT GACCTGAAGG AGCATGTC     1440

CAAGCCTGTC ATTCCCGAGC AGTACCTTGA TGAGAAGACA ATCTTCCATC TTAACCCA     1500

TGGTCGCTTC GTCATTGGCG GACCTCATGG TGATGCTGGT CTCACTGGCC GGAAGATC     1560

CATTGACACT TATGGTGGCT GGGGAGCTCA CGGTGGTGGT GCCTTCTCTG GCAAGGAC     1620

AACCAAGGTT GACCGCAGTG GAGCATACGT CGCAAGGCAA GCTGCCAAGA GCATTGTT     1680

TAGTGGCCTT GCTCGCCGCT GCATTGTCCA AGTATCATAC GCCATCGGTG TCCCAGAG     1740

ACTGTCCGTA TTCGTCGACA CATACGGCAC TGGCAGGATC CCTGACAAGG AGATCCTC     1800

GATTGTGAAG GAGAACTTCG ACTTCAGGCC TGGCATGATC ATCATCAACC TTGACCTC     1860

GAAAGGCGGC AACGGACGCT ACCTCAAGAC GGCGGCTTAC GGTCACTTCG AAGGGAC      1920

CCCAGACTTC ACCTGGGAGG TGGTGAAGCC CCTCAAGTGG GAGAAGCCTT CTGCCTAA     1980

GCTCCCTTTC GGAGGCTTTT GCTCTGTCCC ATTATGGTGT TTTGTTTCCT CGCTGCTC     2040

CATTGTGATT CTTAACCTGC CCCCGCTGC  CATTTATGCC CATGCACGCT ACTTTCCT     2100

TAATAAGTAC TTATAAGGGT ATTGTGTTTG AATATTTTAC CTAGAGGAGG AGGAGGAT     2160

GTTATCTGTT ATTGCTTAAG CTT                                            2183
```

(2) INFORMATION FOR SEQ ID NO: 38:

(i) SEQUENCE CHARACTERISTICS:
        (A) LENGTH: 1485 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: s2.12b06

(xi) SEQUENCE DESCRIPTION: SEQ ID NO: 38:

```
AGCCAAGCCC CACTCAACCA CCACACCACT CTCTCTGCTC TTCTTCTACC TTTCAAGTTT      60

TTAAAGTATT AAGATGGCAG AGACATTCCT ATTTACCTCA GAGTCAGTGA ACGAGGGAC      120

CCCTGACAAG CTCTGCGACC AAATCTCCGA TGCTGTCCTC GACGCTTGCC TTGAACAGG      180

CCCAGACAGC AAGGTTGCCT GCGAAACATG CACCAAGACC AACTTGGTCA TGGTCTTCG      240

AGAGATCACC ACCAAGGCCA ACGTTGACTA CGAGAAGATC GTGCGTGACA CCTGCAGGA      300
```

```
CATCGGCTTC GTCTCAAACG ATGTGGGACT TGATGCTGAC AACTGCAAGG TCCTTGTAA      360

CATTGAGCAG CAGAGCCCTG ATATTGCCCA GGGTGTGCAC GGCCACCTTA CCAAAAGAC      420

CGAGGAAATC GGTGCTGGAG ACCAGGGTCA CATGTTTGGC TATGCCACGG ACGAAACCC      480

AGAATTGATG CCATTGAGTC ATGTTCTTGC AACTAAACTC GGTGCTCGTC TCACCGAGG      540

TCGCAAGAAC GGAACCTGCC CATGGTTGAG GCCTGATGGG AAAACCCAAG TGACTGTTG      600

GTATTACAAT GACAACGGTG CCATGGTTCC AGTTCGTGTC CACACTGTGC TTATCTCCA      660

CCAACATGAT GAGACTGTGA CCAACGACGA AATTGCAGCT GACCTCAAGG AGCATGTGA      720

CAAGCCGGTG ATCCCGGAGA AGTACCTTGA TGAGAAGACC ATTTTCCACT TGAACCCCT      780

TGGCCGTTTT GTCATTGGAG GTCCTCACGG TGATGCTGGT CTCACCGGCC GCAAGATCA      840

CATCGATACT TACGGAGGAT GGGGTGCTCA TGGTGGTGGT GCTTTCTCCG GAAGGATC       900

CACCAAGGTT GATAGGAGTG GTGCTTACAT TGTGAGACAG GCTGCTAAGA GCATTGTGG      960

AAGTGGACTA GCCAGAAGGT GCATTGTGCA AGTGTCTTAT GCCATTGGTG TGCCCGAG      1020

TTTGTCTGTC TTTGTTGACA CCTATGGCAC CGGGAAGATC CATGATAAGG AGATTCTC     1080

CATTGTGAAG GAGAACTTTG ATTTCAGGCC CGGTATGATC TCCATCAACC TTGATCTC     1140

GAGGGGTGGG AATAACAGGT TCTTGAAGAC TGCTGCATAT GGACACTTCG GCAGAGAG     1200

CCCTGACTTC ACATGGGAAG TGGTCAAGCC CCTCAAGTGG GAGAAGGCCT AAGGCCAT     1260

ATTCCACTGC AATGTGCTGG GAGTTTTTTA GCGTTGCCCT TATAATGTCT ATTATCCA     1320

ACTTTCCACG TCCCTTGCTC TGTGTTTTTC TCTCGTCGTC CTCCTCCTAT TTTGTTTC     1380

CTGCCTTTCA TTTGTAATTT TTTACATGAT CAACTAAAAA ATGTACTCTC TGTTTTCC     1440

CCATTGTGTC TCTTAATATC AGTATCAAAA AGAATGTTCC AAGTT                   1485

(2) INFORMATION FOR SEQ ID NO: 39:

(i) SEQUENCE CHARACTERISTICS:
        (A) LENGTH: 392 amino acids
        (B) TYPE: amino acid
        (C) STRANDEDNESS: not relevant
        (D) TOPOLOGY: linear (ii) MOLECULE TYPE: peptide (vii) IMMEDIATE SOURCE:
         (B) CLONE: s2.12b06

(xi) SEQUENCE DESCRIPTION: SEQ ID NO: 39:

Met Ala Glu Thr Phe Leu Phe Thr Ser Glu Ser Val Asn Glu Gly His
1               5                   10                  15

Pro Asp Lys Leu Cys Asp Gln Ile Ser Asp Ala Val Leu Asp Ala Cys
            20                  25                  30

Leu Glu Gln Asp Pro Asp Ser Lys Val Ala Cys Glu Thr Cys Thr Lys
        35                  40                  45

Thr Asn Leu Val Met Val Phe Gly Glu Ile Thr Thr Lys Ala Asn Val
    50                  55                  60

Asp Tyr Glu Lys Ile Val Arg Asp Thr Cys Arg Asn Ile Gly Phe Val
65                  70                  75                  80

Ser Asn Asp Val Gly Leu Asp Ala Asp Asn Cys Lys Val Leu Val Asn
                85                  90                  95

Ile Glu Gln Gln Ser Pro Asp Ile Ala Gln Gly Val His Gly His Leu
            100                 105                 110

Thr Lys Arg Pro Glu Glu Ile Gly Ala Gly Asp Gln Gly His Met Phe
```

```
              115                 120                 125
Gly Tyr Ala Thr Asp Glu Thr Pro Glu Leu Met Pro Leu Ser His Val
    130                 135                 140

Leu Ala Thr Lys Leu Gly Ala Arg Leu Thr Glu Val Arg Lys Asn Gly
145                 150                 155                 160

Thr Cys Pro Trp Leu Arg Pro Asp Gly Lys Thr Gln Val Thr Val Glu
                165                 170                 175

Tyr Tyr Asn Asp Asn Gly Ala Met Val Pro Val Arg Val His Thr Val
            180                 185                 190

Leu Ile Ser Thr Gln His Asp Glu Thr Val Thr Asn Asp Glu Ile Ala
        195                 200                 205

Ala Asp Leu Lys Glu His Val Ile Lys Pro Val Ile Pro Glu Lys Tyr
    210                 215                 220

Leu Asp Glu Lys Thr Ile Phe His Leu Asn Pro Ser Gly Arg Phe Val
225                 230                 235                 240

Ile Gly Gly Pro His Gly Asp Ala Gly Leu Thr Gly Arg Lys Ile Ile
                245                 250                 255

Ile Asp Thr Tyr Gly Gly Trp Gly Ala His Gly Gly Gly Ala Phe Ser
            260                 265                 270

Gly Lys Asp Pro Thr Lys Val Asp Arg Ser Gly Ala Tyr Ile Val Arg
        275                 280                 285

Gln Ala Ala Lys Ser Ile Val Ala Ser Gly Leu Ala Arg Arg Cys Ile
    290                 295                 300

Val Gln Val Ser Tyr Ala Ile Gly Val Pro Glu Pro Leu Ser Val Phe
305                 310                 315                 320

Val Asp Thr Tyr Gly Thr Gly Lys Ile His Asp Lys Glu Ile Leu Asn
                325                 330                 335

Ile Val Lys Glu Asn Phe Asp Phe Arg Pro Gly Met Ile Ser Ile Asn
            340                 345                 350

Leu Asp Leu Lys Arg Gly Gly Asn Asn Arg Phe Leu Lys Thr Ala Ala
        355                 360                 365

Tyr Gly His Phe Gly Arg Glu Asp Pro Asp Phe Thr Trp Glu Val Val
    370                 375                 380

Lys Pro Leu Lys Trp Glu Lys Ala
385                 390

(2) INFORMATION FOR SEQ ID NO: 40:

(i) SEQUENCE CHARACTERISTICS:
        (A) LENGTH: 1479 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
         (A) ORGANISM: Lycopersicon esculentum (xi) SEQUENCE DESCRIPTION: SEQ ID NO: 40:

GAATTCCTAC AAAGAGGTTA TTTCTCTCAA GGGGTAAAAA GATTGCCCCT TTTCGACATT      60

TATAATCCTC TTTTTCTCTT TGTTCGCCGT TGGGTTCTTC ACTTTCCTGT TTCTTGAGA     120

TGGAAACTTT CTTATTCACC TCCGAGTCTG TGAACGAGGG TCACCCAGAC AAGCTCTGT     180

ATCAGATCTC TGATGCAGTT CTTGATGCCT GCCTTGAGCA AGATCCCGAG AGCAAAGTT     240

CATGTGAAAC TTGCACCAAG ACCAACTTGG TCATGGTCTT TGGTGAGATC ACAACCAAG     300
```

-continued

```
CTATTGTAGA CTATGAGAAG ATTGTGCGTG ACACATGCCG TAATATTGGA TTTGTTTCT    360
ATGATGTTGG TCTTGATGCT GACAACTGCA AGGTCCTTGT TTACATTGAG CAGCAAAGT    420
CTGATATTGC TCAAGGTGTC CACGGCCATC TGACCAAACG CCCCGAGGAG ATTGGTGCT    480
GTGACCAGGG CCACATGTTT GGCTATGCAA CAGATGAGAC CCCTGAATTA ATGCCTCTC    540
GTCACGTGCT TGCAACTAAA CTTGGTGCCC GTCTTACAGA AGTCCGCAAG AATGGCACC    600
GCGCCTGGTT GAGGCCTGAT GGCAAGACCC AAGTTACTGT TGAGTATAGC AATGACAAT    660
GTGCCATGGT TCCAATTAGG GTACACACTG TTCTTATCTC CACCCAACAC GATGAGACC    720
TTACCAATGA TGAGATTGCC CGCGACCTTA AGGAGCATGT CATCAAACCA GTCATCCCA    780
AGAAGTACCT TGATGAGAAT ACTATTTTCC ACCTTAACCC ATCTGGCCGA TTCGTTATT    840
GTGGACCTCA TGGTGATGCT GGTCTCACTG GTCGTAAAAT CATCATCGAC ACTTATGGT    900
GTTGGGGTGC TCATGGTGGT GGTGCTTTCT CGGGCAAAGA CCCAACCAAG GTCGACAGG    960
GTGGTGCATA CATTGTAAGG CAGGCTGCAA AGAGTATCGT AGCTAGTGGA CTTGCTCG   1020
GATGCATCGT GCAGGTATCT TATGCCATCG GTGTGCCTGA GCCATTGTCT GTATTCGT   1080
ACACCTATGG CACTGGAAAG ATCCCTGACA GGGAAATTTT GAAGATCGTT AAGGAGAA   1140
TTGACTTCAG ACCTGGAATG ATGTCCATTA ACTTGGATTT GAAGAGGGGT GGCAATAG   1200
GATTCTTGAA AACTGCTGCC TATGGTCACT TTGGACGTGA TGACCCCGAT TTCACATG   1260
AAGTTGTCAA GCCCCTCAAG TGGGAAAAGC CCCAAGACTA ATAAGTGCTT GCCTATGT   1320
TTGTTCTTTG TTGTTTGCTT GTGGCTTTAG AATCTCCCCC GTGTTTGCTT GTTTGTCT   1380
GTATTTTCTC TTTTGACCCT TTATTTTGTT ATTGTCCTGT TTCCATTGTG TTGGATGG   1440
ATCTTAGGCC TTGGAATATT AAGGAAAGAA AAGGAATTC                        1479
```

(2) INFORMATION FOR SEQ ID NO: 41:

(i) SEQUENCE CHARACTERISTICS:
        (A) LENGTH: 1380 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 41:

```
CCCTCCCTTC GGTTCATCGG CCTCCCGATC GAGCAGTAGA AGCAGCGCAA GGGCATCGCT     60
AGCACTAAAG AAATGGCAGC CGAGACGTTC CTCTTCACGT CCGAGTCTGT GAACGAGGG    120
CATCCCGACA AGCTCTGTGA CCAAGTCTCC GACGCCGTCT GGATGCCTG CTTGGCCCA     180
GATGCCGACA GCAAGGTCGC CTGCGAGACC GTCACCAAGA CCAACATGGT CATGGTCTT    240
GGCGAGATCA CCACCAAGGC CACCGTCGAC TATGAGAAGA TCGTGCGTGA CACCTGCCG    300
AACATCGGTT TCATCTCTGA TGACGTTGGT CTCGACGCCG ACCGTTGCAA RGTGCTCGT    360
AACATCGAGC AGCAGTCCCC TGACATTGCC CAGGGTGTTC ATGGACACTT CACCAAGCG    420
CCCGAAGAAG TCGCGCCGG TGACCAGGGC ATCATGTTCG GCTATGCCAC CGATGAGAC    480
CCTGAGCTGA TGCCCCTCAA GCACGTGCTT GCCACCAAGC TYGGAGCTCG CCTCACSGA    540
GTCCGCAAGA ATGGCACCTG CGCCTGGGTC AGGCCTGACG GAAAGACCCA GGTCACAGT    600
GAGTACCTAA ACGAGGATGG TGCCATGGTA CCTGTTCGTG TGCACACCGT CCTCATCTC    660
ACCCAGCACG ACGAGACCGT CACCAACGAC GAGATTGCTG CGGACCTCAA GGAGCATGT    720
ATCAAGCCGG TGATCCCCGC AAAGTACCTC GATGAGAACA CCATCTTCCA CCTGAACCC    780
```

```
TCTGGCCGCT TCGTCATCGG CGGCCCCCAC GGTGACGCCG GTCTCACCGG CCGCAAGAT        840

ATCATCGACA CCTATGGTGG CTGGGGAGCC CACGGCGGCG GTGCCTTCTC TGGCAAGGA        900

CCAACCAAGG TCGACCGYAG TGGCGCCTAC ATTGCCAGGC ARGCCGCCAA GAGCATCAT        960

GCCAGCGGCC TCGCACGCCG CTGCATTGTG CAGATCTCAT ACGCCATCGG TGTGCCTG       1020

CCTTTGTCTG TGTTCGTCGA CTCCTACGGC ACCGGCAAGA TCCCCGACAG GGAGATCC       1080

AAGCTCGTGA AGGAGAACTT TGACTTCAGG CCCGGGATGA TCAGCATCAA CCTGGACT       1140

AAGAAAGGTG AAACAGGTT CATCAAGACC GCTGCTTACG GTCACTTTGG CCGTGATG       1200

GCCGACTTCA CCTGGGAGGT GGTGAAGCCC CTCAAGTTCG ACAAGGCATC TGCCTAAG       1260

CATGGCATTC TCTTGGTCTG CCGCCTCTCA AGTTCGTCAA GACGGGATCA TGTTGCTC       1320

GGGAAGTGGG AAGAAGCATT AGACATTGAA GCGACGCTCT ACACTGGTCT TGTTGTAT       1380
```

(2) INFORMATION FOR SEQ ID NO: 42:

(i) SEQUENCE CHARACTERISTICS:
        (A) LENGTH: 394 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 42:

```
Met Ala Ala Glu Thr Phe Leu Phe Thr Ser Glu Ser Val Asn Glu Gly
 1               5                  10                  15

His Pro Asp Lys Leu Cys Asp Gln Val Ser Asp Ala Val Leu Asp Ala
            20                  25                  30

Cys Leu Ala Gln Asp Ala Asp Ser Lys Val Ala Cys Glu Thr Val Thr
        35                  40                  45

Lys Thr Asn Met Val Met Val Leu Gly Glu Ile Thr Thr Lys Ala Thr
    50                  55                  60

Val Asp Tyr Glu Lys Ile Val Arg Asp Thr Cys Arg Asn Ile Gly Phe
65                  70                  75                  80

Ile Ser Asp Asp Val Gly Leu Asp Ala Asp Arg Cys Lys Val Leu Val
                85                  90                  95

Asn Ile Glu Gln Gln Ser Pro Asp Ile Ala Gln Gly Val His Gly His
            100                 105                 110

Phe Thr Lys Arg Pro Glu Glu Val Gly Ala Gly Asp Gln Gly Ile Met
        115                 120                 125

Phe Gly Tyr Ala Thr Asp Glu Thr Pro Glu Leu Met Pro Leu Lys His
    130                 135                 140

Val Leu Ala Thr Lys Leu Gly Ala Arg Leu Thr Glu Val Arg Lys Asn
145                 150                 155                 160

Gly Thr Cys Ala Trp Val Arg Pro Asp Gly Lys Thr Gln Val Thr Val
                165                 170                 175

Glu Tyr Leu Asn Glu Asp Gly Ala Met Val Pro Val Arg Val His Thr
            180                 185                 190

Val Leu Ile Ser Thr Gln His Asp Glu Thr Val Thr Asn Asp Glu Ile
        195                 200                 205

Ala Ala Asp Leu Lys Glu His Val Ile Lys Pro Val Ile Pro Ala Lys
    210                 215                 220

Tyr Leu Asp Glu Asn Thr Ile Phe His Leu Asn Pro Ser Gly Arg Phe
225                 230                 235                 240

Val Ile Gly Gly Pro His Gly Asp Ala Gly Leu Thr Gly Arg Lys Ile
```

```
                     245                 250                 255
Ile Ile Asp Thr Tyr Gly Gly Trp Gly Ala His Gly Gly Ala Phe
                260                 265                 270

Ser Gly Lys Asp Pro Thr Lys Val Asp Arg Ser Gly Ala Tyr Ile Ala
            275                 280                 285

Arg Gln Ala Ala Lys Ser Ile Ile Ala Ser Gly Leu Ala Arg Arg Cys
        290                 295                 300

Ile Val Gln Ile Ser Tyr Ala Ile Gly Val Pro Glu Pro Leu Ser Val
305                 310                 315                 320

Phe Val Asp Ser Tyr Gly Thr Gly Lys Ile Pro Asp Arg Glu Ile Leu
                325                 330                 335

Lys Leu Val Lys Glu Asn Phe Asp Phe Arg Pro Gly Met Ile Ser Ile
            340                 345                 350

Asn Leu Asp Leu Lys Lys Gly Gly Asn Arg Phe Ile Lys Thr Ala Ala
        355                 360                 365

Tyr Gly His Phe Gly Arg Asp Asp Ala Asp Phe Thr Trp Glu Val Val
    370                 375                 380

Lys Pro Leu Lys Phe Asp Lys Ala Ser Ala
385                 390
```

(2) INFORMATION FOR SEQ ID NO: 43:

(i) SEQUENCE CHARACTERISTICS:
        (A) LENGTH: 1353 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Hordeum vulgare (xi) SEQUENCE DESCRIPTION: SEQ ID NO: 43:

```
GAATTCCGGA TAGCATCAGC ACAACTGCAC GAGAGCATCT CTACCACCAA AGAAATGGCG      60
GCCGAGACGT TCCTCTTCAC GTCCGAGTCC GTGAACGAGG CCATCCCGA CAAGCTGTG      120
GACCAGGTCT CTGACGCCGT CTTGGACGCC TGCTTGGCCC AGGATCCTGA CAGCAAGGT      180
GCTTGCGAGA CCTGCACCAA GACCAACATG GTCATGGTCT TCGGCGAGAT CACCACCAA      240
GCCACCGTTG ACTATGAGAA GATTGTGCGC GACACCTGCC GTGACATCGG CTTCATCTC      300
GACGACGTCG GTCTCGATGC CGACCATTGC AAGGTGCTCG TCAACATCGA GCAGCAATC      360
CCTGACATTG CCCAGGGTGT TCACGGACAC TTCACCAAGC GTCCAGAAGA GGTCGGCGC      420
GGTGACCAGG GCATCATGTT TGGCTACGCC ACTGATGAGA CCCCTGAGCT GATGCCCCT      480
ACCCACATGC TTGCCACCAA GCTCGGAGCT CGCCTCACCG AGGTCCGCAA GAATGGCAC      540
TGCGCCTGGC TCAGGCCTGA TGGAAAGACC CAGGTCACCA TTGAGTACCT AAACGAGGG      600
GGTGCCATGG TGCCCGTTCG TGTGCACACC GTCCTCATCT CCACCCAGCA TGATGAGAC      660
GTCACCAACG ATGAGATCGC TGCAGACCTC AAGGAGCATG TCATCAAGCC GGTGATTCC      720
GGGAAGTACC TCGATGAGAA CACCATCTTC CACCTGAACC CATCGGGCCG CTTTGTCAT      780
GGTGGCCCTC ACGGCGATGC CGGTCTCACC GCCCGCAAGA TCATCATCGA CACCTATGG      840
GGCTGGGGAG CCCACGGCGG CGGTGCCTTC TCTGGCAAGG ACCCTACCAA GGTCGACCG      900
AGTGGCGCCT ACATTGCCAG GCAGGCTGCC AAGAGCATCA TCGCCAGCGG CCTCGCACG      960
CGGTGCATTG TGCAGATCTC ATATGCCATC GGTGTACCTG AGCCTTTGTC TGTGTTCG     1020
```

```
GACTCCTACG GCACTGGCAA GATCCCTGAC AGGGAGATCC TCAAGCTCGT GAAGGAGA      1080

TTTGACTTCA GACCCGGGAT GATCACGATC AACCTCGACT TGAAGAAAGG TGGAAACA      1140

TTCATCAAGA CAGCTGCTTA CGGTCACTTT GGCCGCGATG ATGCTGACTT CACCTGGG      1200

GTGGTGAAGC CCCTCAAGTT CGACAAGGCA TCTGCTTAAG AAGAAGACAT CACATTGA      1260

GTTCTTCTTG GTCTGATGCC TCTCAAGTTC GGCAAGGCGG GATCCTTTTG CTCCTCGG      1320

GTAAGAAGAA GCATTCAACA TCGCCCGGAA TTC                                 1353
```